United States Patent [19]

Miyake et al.

[11] Patent Number: 5,409,919
[45] Date of Patent: * Apr. 25, 1995

[54] PHARMACEUTICALLY ACCEPTABLE SALT OF 7B-[2-(5-AMINO-1,2,4-THIO-DIAZOL-3-YL)-2(Z)-METHO-XYIMINOACETAMIDO]-3-[(IMIDAZO[1,2-B]PYRIDAZINIUM-1-YL)METHYL]-3-CEPHEM-4-CARBOXYLATE AND COMPOSITION COMPRISING SAME

[75] Inventors: Akio Miyake; Masahiro Kondo, both of Osaka; Masahiko Fujino, Hyogo, all of Japan

[73] Assignee: Takeda Chemical Industries, Ltd., Osaka, Japan

[*] Notice: The portion of the term of this patent subsequent to Sep. 5, 2006 has been disclaimed.

[21] Appl. No.: 41,849

[22] Filed: Apr. 2, 1993

Related U.S. Application Data

[63] Continuation of Ser. No. 899,173, Jun. 15, 1992, abandoned, which is a continuation of Ser. No. 552,006, Jul. 13, 1990, abandoned, which is a continuation of Ser. No. 331,192, Mar. 28, 1989, Pat. No. 4,962,100, which is a continuation of Ser. No. 834,969, Feb. 28, 1986, Pat. No. 4,864,022.

[30] Foreign Application Priority Data

Apr. 17, 1985 [NO] Norway ................. 851538
Sep. 20, 1985 [JP] Japan ................. 60-209320

[51] Int. Cl.⁶ ................. C07D 501/46; A61K 31/545
[52] U.S. Cl. ................. 514/202; 540/222
[58] Field of Search ................. 540/222, 225, 226; 514/202

[56] References Cited

U.S. PATENT DOCUMENTS

| | | | |
|---|---|---|---|
| 4,665,065 | 5/1987 | Miyake et al. | 514/202 |
| 4,788,185 | 11/1988 | Miyake et al. | 540/227 |
| 4,826,834 | 5/1989 | Yoshimura et al. | 540/225 |
| 4,864,022 | 9/1989 | Miyake et al. | 540/222 |
| 4,921,851 | 5/1990 | Kishimoto et al. | 540/222 |
| 4,962,100 | 10/1990 | Miyake et al. | 514/202 |
| 4,978,752 | 12/1990 | Maeda et al. | 540/222 |

*Primary Examiner*—Nicholas Rizzo
*Attorney, Agent, or Firm*—Foley & Lardner

[57] ABSTRACT

A compound of the formula:

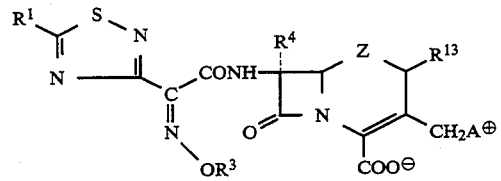

wherein $R^1$ is an amino group which may be protected, $R^3$ is a hydrogen atom or an optionally substituted hydrocarbon residue; Z is S, S→O, O or $CH_2$, $R^4$ is a hydrogen atom, methoxy group or formamido group, $R^{13}$ is a hydrogen atom, methyl group, hydroxyl group or halogen atom and $A^{\oplus}$ is an optionally substituted imidazolium-1-yl group forming a condensed ring at the 2,3- or 3,4-position or a pharmaceutically acceptable salt or ester thereof is novel and has excellent antibacterial activity.

4 Claims, No Drawings

PHARMACEUTICALLY ACCEPTABLE SALT OF 7B-[2-(5-AMINO-1,2,4-THIO-DIAZOL-3-YL)-2(Z)-METHO-XYIMINOACETAMIDO]-3-[(IMIDAZO[1,2-B]PYRIDAZINIUM-1-YL)METHYL]-3-CEPHEM-4-CARBOXYLATE AND COMPOSITION COMPRISING SAME

This application is a continuation of Ser. No. 07/899,173, filed Jun. 15, 1992, now abandoned; which is a continuation of Ser. No. 07/552,006 filed Jul. 13, 1990, now abandoned; which is a continuation of 07/331,192, filed Mar. 28, 1989, now U.S. Pat. No. 4,962,100, which is a continuation of Ser. No. 07/834,969, filed Feb. 28, 1986, now U.S. Pat. No. 4,864,022.

This invention relates to novel antibacterial compounds having excellent antibacterial action, a method of preparing the same and a pharmaceutical composition containing the same.

A variety of cephem compounds having a quaternary ammoniomethyl group at the 3-position and 2-(2-aminothiazol-4-yl)-2-hydroxy(or substituted hydroxy)iminoacetamido group at the 7-position simultaneously have so far been synthesized, and patent applications [for instance Japanese Publication of Unexamined Application (Kokai) No. Sho-53-34795, No. Sho-54-9296, No. Sho-54-135792, No. Sho-54-154786, No. Sho-55-149289, No. Sho-57-56485, No. Sho-57-192394, No. Sho-58-159498, etc. the United States or other Western equivalents of which are, respectively, DE-OLS No. 2,715,385, U.S. Pat. Nos. 4,278,793, 3,932,385, 4,258,041, 4,098,888, U.K. Pat. No. 2,098,216, U.S. Pat. No. 4,278,793] concerning those compounds have been published. However, most of the compounds, whose quaternary ammoniomethyl group at the 3-position has a nitrogen-containing aromatic heterocyclic ring, are those having a monocyclic pyridinium group with or without a substituent or substituents on the ring thereof, and the compounds of the present invention having an imidazolium-1-yl group which forms a condensed ring at the 2,3-position or the 3,4-position have never been disclosed in the specification of an patent application, not to speak of a report of the synthesis thereof.

Cephem-type antibiotics have been widely used for the therapy of diseases of human beings and animals caused by pathogenic bacteria. These compounds are especially useful for the therapy of diseases caused by bacteria resistant to penicillin-type antibiotics as well as for the therapy of penicillin-sensitive patients. In these cases, it is desirable to use cephem-type antibiotics showing activity against both gram-positive and gram-negative bacteria. For this reason, expensive studies on cephem-type antibiotics having a wide antibacterial spectrum have been carried out. As a result of research work covering a long period of time, it has been found that introduction of 2-(2-aminothiazol-4-yl)-2-hydroxy (or substituted hydroxy)iminoacetamido group or nitrogen-containing heterocycle-amino group at the 7-position of cephem ring renders the cephem compound active against both gram-positive and gram-negative bacteria which has led to the exploitation and development of what is called "the third generation cephalosporin". At present, several types of the third generation cephalosporin compounds have already been put on the market. Another characteristic feature of these third generation cephalosporin antibiotics lies in that these substances are active against the so-called cephalosporin-resistant bacteria, which penicillins have also encountered. More specifically, cephem compounds of the third generation showed antibacterial action to such an extent as to make them clinically usable against some strains of Escherichia coli, some of the bacteria belonging to the genus Citrobacter and most of the bacteria belonging to the genus Proteus that are positive to indole reactions as well as against most of the phathogenic bacteria classified into the genus Enterobacter, Serratia or Pseudomonas.

However, the third generation cephalosporin compounds are not always satisfactory. Their antibacterial activities for example against Pseudomonas are not satisfactorily strong.

More concretely, the present invention relates to a compound of the formula:

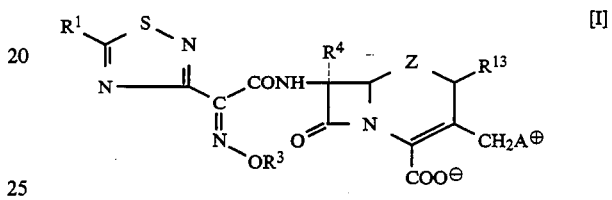

wherein $R^1$ is an amino group which may be protected, $R^3$ is a hydrogen atom or an optionally substituted hydrocarbon residue; Z is S, S→O, O or $CH_2$, $R^4$ is a hydrogen atom, methoxy group or formamido group, $R^{13}$ is a hydrogen atom, methyl group, hydroxyl group or halogen atom and $A^\oplus$ is an optionally substituted imidazolium-1-yl group forming a condensed ring at the 2,3- or 3,4-position or a pharmaceutically acceptable salt or ester thereof (the compound [I], and pharmaceutically acceptable salt and ester thereof may simply be abbreviated hereinafter as the compound [I] or the antibacterial compound [I]).

More specifically, the antibacterial compounds of the present invention are cephem compounds represented by the formula [I] (Z=S, S→O) as well as oxa-(Z=O) or carba-(Z=$CH_2$) derivatives thereof.

The cephem compounds in the present specification are a group of compounds named on the basis of "cepham" disclosed in the "The Journal of the American Chemical Society" Vol. 84, p. 3400 (1962), and mean, among the cepham compounds, those having a double bond at the 3,4-position.

As stated hereinbefore, it has gradually become apparent that a cephem compound as well as oxa- or carba-derivatives thereof having a quaternary ammoniomethyl group at the 3-position and an aminothiazolyloxyiminoacetamido group or nitrogen-containing heterocycle-amino group at the 7-position simultaneously has especially excellent antibacterial activity and specific antibacterial spectrum. A number of compounds having a nitrogen-containing aromatic heterocyclic ring as the quaternary ammoniomethyl group at the 3-position have already been synthesized and corresponding patent applications have been published. Most of those heterocyclic rings are monocyclic pyridinium groups or those having a substituent on the ring thereof, and compounds of this invention having an imidazolium-1-yl group which forms a condensed ring at the 2,3-position or the 3,4-position have not been synthesized at all. The present inventors succeeded in synthesizing the compounds represented by the formula [I] having such structural features, and examined the antibacterial activities and antibacterial spectrum, resulting in the findings that the compounds [I] or their pharmaceutically acceptable salts or esters have strong antibacterial action against various bacteria, especially against cephalosporin-resistant bacteria, and that they show specific antibacterial action against bacteria belonging to the genus Pseudomonas, and completed the present invention.

Reference is made as follows to the group names and symbols used in the present specification. Unless otherwise specifically defined, those groups and symbols are of the following meanings respectively.

"Alkyl group" is preferably a straight-chain or branched lower alkyl group having 1–6 carbon atoms (hereinafter sometimes mentioned briefly as "$C_{1-6}$ alkyl group"), which is exemplified by methyl, ethyl, n-propyl, isopropyl, n-butyl, isobutyl, sec-butyl, tert-butyl, n-pentyl or n-hexyl.

"Alkenyl group" is preferably a straight-chain or branched lower alkenyl group having 2–6 carbon atoms (hereinafter sometimes mentioned briefly as "$C_{2-6}$ alkenyl group"), which is exemplified by vinyl, allyl, 1-propenyl, isopropenyl, 1-butenyl, 2-butenyl, 3-butenyl, methallyl, or 1,1-dimethylallyl.

"Alkynyl group" is preferably a straight-chain or branched lower alkynyl group having 2–6 carbon atoms (hereinafter sometimes mentioned briefly as "$C_{2-6}$ alkynyl group"), which is exemplified by ethynyl, 1-propynyl or propargyl.

"Cycloalkyl group" is preferably a 3–7 membered alicyclic hydrocarbon group having 3–10 carbon atoms (hereinafter sometimes mentioned briefly as "$C_{3-10}$ cycloalkyl group"), which is exemplified by cyclopropyl, cyclobutyl, cyclopentyl, cyclohexyl, cycloheptyl, norbornyl or adamantyl.

"Cycloalkenyl group" is preferably a 5–6 membered alicyclic hydrocarbon group having one or two double bonds (hereinafter sometimes mentioned briefly as "$C_{5-6}$ cycloalkenyl group"), which is exemplified by cyclopentenyl, cyclopentadienyl, cyclohexenyl or cyclohexadienyl.

"Aryl group" is preferably an aromatic hydrocarbon group having 6–10 carbon atoms (hereinafter sometimes mentioned briefly as "$C_{6-10}$ aryl group"), which is exemplified by phenyl, α-naphthyl, β-naphthyl or biphenylyl.

"Aralkyl group" is preferably an aromatically substituted alkyl group having 7–12 carbon atoms (hereinafter sometimes mentioned briefly as "$C_{7-12}$ aralkyl group"), which is exemplified by benzyl, 1-phenylethyl, 2-phenylethyl, phenylpropyl or naphthylmethyl. Incidentally, the $C_{7-12}$ aralkyl group, in combination with the di-$C_{6-10}$ aryl-methyl group and tri-$C_{6-10}$ aryl-methyl group, is sometimes stated as "$C_{7-19}$ aralkyl group".

"Diarylmethyl group" means methyl group substituted with two $C_{6-10}$ aryl groups mentioned above (hereinafter sometimes mentioned briefly as "di-$C_{6-10}$ aryl-methyl group"), which is exemplified by benzhydryl.

"Triarylmethyl group" means methyl group substituted with three $C_{6-10}$ aryl groups mentioned above (hereinafter sometimes mentioned briefly as "tri-$C_{6-10}$ arylmethyl group"), which is exemplified by trityl.

The aryl group of the "arylmethylene group" is preferably a $C_{6-10}$ aryl group mentioned above; hence the "arylmethylene group" is hereinafter sometimes called a "$C_{6-10}$ arylmethylene group", which is exemplified by benzylidene ($C_6H_5CH=$).

The alkyl group of the "alkoxy group" is preferably a $C_{1-6}$ alkyl group mentioned above; hence the "alkoxy group" is hereinafter sometimes called a "$C_{1-6}$ alkoxy group", which is exemplified by methoxy, ethoxy, n-propoxy, isopropoxy, n-butoxy, tert-butoxy, amyloxy or hexyloxy.

The cycloalkyl group of the "cycloalkyloxy group" is preferably a $C_{3-10}$ cycloalkyl group mentioned above; hence the "cycloalkyloxy group" is hereinafter sometimes called a "$C_{3-10}$ cycloalkyloxy group", which is exemplified by cyproyloxy, cyclopentyloxy, cyclohexyloxy or norbornyloxy.

The aryl group of the "aryloxy group" is preferably a $C_{6-10}$ aryl group mentioned above; hence the "aryloxy group" is hereinafter sometimes called a "$C_{6-10}$ aryoxy group", which is exemplified by phenoxy or naphthyloxy.

The aralkyl group of the "aralkyloxy group" is preferably a $C_{7-19}$ aralkyl group mentioned above; hence the "aralkyloxy group" is hereinafter sometimes called a "$C_{7-19}$ aralkyloxy group", which is exemplified by benzyloxy, 1-phenylethyloxy, 2-phenylethyloxy, naphtylmethyloxy, benzhydryloxy or trityloxy.

The alkyl group of the "alkylthio group" is preferably a $C_{1-6}$ alkyl group mentioned above; hence the "alkylthio group" is hereinafter sometimes called a "$C_{1-6}$ alkylthio group", which is exemplified by methylthio, ethylthio, n-propylthio or n-butylthio.

The alkylthio group of the "aminoalkylthio group" is preferably a $C_{1-6}$ alkylthio group mentioned above; hence the "aminoalkylthio group" is hereinafter called an "amino $C_{1-6}$ alkylthio group", which is exemplified by aminomethylthio, 2-aminoethylthio or 3-aminopropylthio.

The alkenyl group of the "alkenylthio group" is preferably a $C_{2-6}$ alkenyl group mentioned above; hence the "alkenylthio group" is hereinafter sometimes called a "$C_{2-6}$ alkenylthio group", which is exemplified by vinylthio, allylthio, 1-propenylthio or isopropenylthio.

The cycloalkyl group of the "cycloalkylthio group" is preferably a $C_{3-10}$ cycloalkyl group mentioned above; hence the "cycloalkylthio group" is hereinafter sometimes called a "$C_{3-10}$ cycloalkylthio group, which is exemplified by cyclopropylthio or cyclohexylthio.

The aryl group of the "arylthio group" is preferably a $C_{6-10}$ aryl group mentioned above; hence the "arylthio group" is hereinafter sometimes called a "$C_{6-10}$ arylthio group", which is exemplified by phenylthio or naphthylthio.

The aralkyl group of the "aralkylthio group" is preferably a $C_{7-19}$ aralkyl mentioned above, hence the "aralkylthio group" is hereinafter sometimes called a "$C_{7-19}$ aralkylthio group", which is exemplified by benzylthio, phenylethylthio, benzhydrylthio or tritylthio.

The alkyl group of the "monoalkylamino group" is preferably a $C_{1-6}$ alkyl group mentioned above; hence the "monoalkylamino group" is hereinafter sometimes called a "mono-$C_{1-6}$ alkylamino group", which is exemplified by methylamino, ethylamino, n-propylamino, n-butylamino, tert-butylamino, n-pentylamino or n-hexylamino.

the alkyl group of the "dialkylamino group" is preferably a $C_{1-6}$ alkyl group mentioned above hence the "dialkylamino group" is hereinafter sometimes called a "di-$C_{1-6}$ alkyloamino group", which is exemplified by dimethylamino, diethylamino, methylethylamino, di-(n-propyl)amino or di-(n-butyl)amino.

The alkyl group of the "trialkylammonium group" is preferably a $C_{1-6}$ alkyl group mentioned above; hence "trialkylammonium group" is hereinafter sometimes called a "tri-$C_{1-6}$alkylammonium group", which is exemplified by trimethylammonium [$(CH_3)_3N^{\oplus}$-] or triethylammonium. The trialkyloammonium group is usually accompanied by a corresponding anion exemplified by a halogenide ion (chloride ion, bromide ion, iodide ion, etc.), sulfate ion, nitrate ion, carbonate ion, organic carboxylate ion (e.g. oxaloate ion or trifluoroacetate ion), organic sulfonate ion (e.g. methanesulfonate ion or p-toluenesulfonate ion). The organic carboxylate ion and the organic sulfonate ion may sometimes by intramolecular ones.

The cycloalkyl group of the "cycloalkylamino group" is preferably a $C_{3-10}$cycloalkyl group mentioned above; hence the "cycloalkylamino group" is hereinafter sometimes called a "$C_{3-10}$cycloalkyloamino", which is exemplified by cyclopropylamino, cyclopentylamino or cyclohexylamino.

The aryl group of the "arylamino group" is preferably a $C_{6-10}$ aryl group mentioned above; hence "arylamino group" is hereinafter sometimes called a "$C_{6-10}$ arylamino group", which is exemplified by anilino or N-methylanilino.

The aralkyl group of the "aralkylamino group" is preferably a $C_{7-19}$aralkyl group mentioned above; hence "aralkylamino group" is hereinafter sometimes called a "$C_{7-19}$aralkylamino group", which is exemplified by benzylamino, 1-phenylethylamino, 2-phenylethylamino, benzhydrylamino or tritylamino.

"Cyclic amino group" means a group formed by removing one of the hydrogen atoms attached to the ring-constituting nitrogen atom or a nitrogen-containing heterocyclic ring as described hereafter, which is exemplified by 1H-tetrazol-1-yl, 1H-pyrrol-1-yl, pyrrolino, pyrrolidino, 1H-imidazol-1-yl, imidazolino, imidazolidino, 1H-pyrazol-1-yl, pyrazolino, pyrazolidino, piperidino, piperazino or morpholino.

The alkyl group of the "hydroxyalkyl group" is preferably a $C_{1-6}$alkyl group mentioned above; hence the "hydroxyalkyl group" is hereinafter sometimes called a "hydroxy $C_{1-6}$ alkyl group", which is exemplified by hydroxymethyl, 1-hydroxyethyl, 2-hydroxyethyl or 3-hydroxypropyl.

The alkyl group of the "mercaptoalkyl group" is preferably a $C_{1-6}$alkyl group mentioned above; hence the "mercaptoalkyl group" is hereinafter sometimes called a "mercapto $C_{1-6}$alkyl group", which is exemplified by mercaptomethyl, 1-mercaptoethyl or 2-mercaptoethyl.

The alkoxy group of the "alkoxyalkyl group" is preferably a $C_{1-6}$ alkoxy group mentioned above and the alkyl group of the "alkoxyalkyl group" is preferably a $C_{1-6}$alkyl group mentioned above; hence the "alkoxyalkyl group" is hereinafter sometimes called a "$C_{1-6}$alkoxy $C_{1-6}$alkyl group", which is exemplified by methoxymethyl, ethoxymethyl or 2-methoxyethyl.

The alkylthio group of the "alkylthio group" is preferably a $C_{1-6}$alkylthio group mentioned above and the alkyl group of the "alkylthioalkyl group" is preferably a $C_{1-6}$alkyl group mentioned above; hence the "alkylthioalkyl group" is hereinafter sometimes called a "$C_{1-6}$alkylthio $C_{1-6}$alkyl group", which is exemplified by methylthiomethyl or 2-methylthioethyl.

The alkyl group of the "aminoalkyl group" is preferably a $C_{1-6}$alkyl group mentioned above; hence the "aminoalkyl group" is hereinafter sometimes called an "amino $C_{1-6}$ alkyl group", which is exemplified by aminomethyl, 2-aminoethyl or 3-aminopropyl.

"Monoalkylaminoalkyl group" is preferably a "mono-$C_{1-6}$alkyl amino $C_{1-6}$alkyl group", which is exemplified by methylaminomethyl, ethylaminomethyl, 2-(N-methylamino) ethyl or 3-(N-methylamino)propyl.

"Dialkylaminoalkyl group" is preferably a "di-$C_{1-6}$alkylamino $C_{1-6}$alkyl group", which is exemplified by N,N-dimethylaminomethyl, N,N-diethylaminomethyl, 2-(N,N-dimethylamino)ethyl, 2-(N,N-diethylamino)ethyl or 3-(N,N-diethylamino)propyl.

The cyclic amino group of the "cyclic aminoalkyl group" is preferably the one mentioned above and the alkyl group of the "cyclic aminoalkyl group" is preferably a $C_{1-6}$alkyl group mentioned above; hence hereinafter the "cyclic aminoalkyl group" is sometimes called a "cyclic amino $C_{1-6}$ alkyl group", which is exemplified by pyrrolidinomethyl, piperidinomethyl piperazinomethyl, morpholinomethyl or 2-(morpholino)ethyl.

The cyclic aminoalkyl group of the "cyclic aminoalkylamino group" is preferably cyclic amino $C_{1-6}$alkyl group mentioned above; hence hereinafter the "cyclic aminoalkylamino group" is sometimes called a "cyclic amino $C_{1-6}$alkylamino group", which is exemplified by pyrrolidinomethylamino, piperizinomethylamino, piperazinomethylamino or morpholinomethylamino.

The alkyl group of the "halogenoalkyl group" is preferably a $C_{1-6}$ alkyl group mentioned above; hence hereinafter the "halogenoalkyl group" is sometimes called a "halogeno $C_{1-6}$ alkyl group", which is exemplified by fluoromethyl, difluoromethyl, trifluoromethyl, chloromethyl, dichloromethyl, trichloromethyl, 2-fluoroethyl, 2,2-difluoroethyl, 2,2,2-trifluoroethyl, 2-chloroethyl, 2,2-dichloroethyl, 2,2,2-trichloroethyl, 2-bromoethyl or 2-iodoethyl.

The alkyl group of the "cyanoalkyl group" is preferably a $C_{1-6}$alkyl group mentioned above; hence hereinafter the "cyanoalkyl group" is sometimes called a "cyano $C_{1-6}$alkyl group", which is exemplified by cyanomethyl or 2-cyanoethyl.

The alkyl group of the "carboxyalkyl group" is preferably a $C_{1-6}$alkyl group mentioned above; hence hereinafter the "carboxyalkyl group" is called sometimes a "carboxy $C_{1-6}$alkyl group", which is exemplified by carboxymethyl, 1-carboxyethyl or 2-carboxyethyl.

The alkyl group of the "sulfoalkyl group" is preferably a $C_{1-6}$alkyl group mentioned above; hence hereinafter the "sulfoalkyl group" is called sometimes a "sulfo $C_{1-6}$alkyl group", which is exemplified by sulfomethyl or 2-sulfoethyl.

The alkanoyl group of the "alkanoylalkyl group" is preferably a $C_{2-6}$alkanoyl group mentioned hereafter and the alkyl group of the "alkanoylalkyl group" is preferably a $C_{1-6}$alkyl group mentioned above; hence hereinafter the "alkanoylalkyl group" is sometimes called a "$C_{2-6}$alkanoyl $C_{1-6}$alkyl group", which is exemplified by acetylmethyl, 1-acetylethyl or 2-acetylethyl.

The alkanoyloxy group of the "alkanoyloxyalkyl group" is preferably a $C_{2-6}$alkanoyloxy group to be described hereafter and the alkyl group of the "alkanoyloxyalkyl group" is preferably a $C_{1-6}$alkyl group mentioned above; hence hereinafter the "alkanoyloxyalkyl group" is sometimes called a "$C_{2-6}$alkanoyloxy $C_{1-6}$alkyl group", which is exemplified by acetoxymethyl, 1-acetoxyethyl or 2-acetoxyethyl.

The alkoxycarbonyl group of the "alkoxycarbonylalkyl group" is preferably a $C_{1-10}$alkoxy-carbonyl group to be described hereafter and the alkyl group of the "alkoxycarbonylalkyl group" is preferably a $C_{1-6}$alkyl group mentioned above; hence hereinafter the "alkoxycarbonylalkyl group" is sometimes called a "$C_{1-10}$alkoxy-carbonyl $C_{1-6}$alkyl group", which is exemplified by methoxycarbonylmethyl, ethoxycarbonylmethyl or tert-butoxycarbonylmethyl.

The alkyl group of the "carbamoylalkyl group" is preferably a $C_{1-6}$alkyl group; hence hereinafter the "carbamoyalkyl-group" is sometimes called a "carbamoyl $C_{1-6}$alkyl group", which is exemplified by carbamoylmethyl.

The alkyl group of the "carbamoyloxyalkyl group" is preferably a $C_{1-6}$alkyl group; hence hereinafter the "carbamoylalkyl group" is called sometimes a "carbamoyloxy $C_{1-6}$ alkyl group", which is exemplified by carbamoyloxymethyl.

"Halogen atom" is exemplified by fluorine, chlorine, bromine or iodine.

"Alkanoyl group" is preferably an aliphatic acyl group having 1-6 carbon atoms (hereinafter sometimes called simply "$C_{1-6}$alkanoyl group", which is exemplified by formyl acetyl, propionyl, butyryl, isobutyryl, valeryl, isovaleryl or pivaloyl. These alkanoyl groups, except formyl, are sometimes called a "$C_{2-6}$alkanoyl group".

"Alkenoyl group" is preferably one having 3 to 5 carbon atoms (hereinafter sometimes simply called "$C_{3-5}$ alkenoyl group"), which is exemplified by acryloyl, crotonoyl or maleoyl.

The cycloalkyl group of the "cycloalkylcarbonyl group" is preferably a $C_{3-10}$cycloalkyl group mentioned above; hence hereinafter the "cycloalkylcarbonyl group" is sometimes called a "$C_{3-10}$cycloalkyl-carbonyl group", which is exemplified by cyclopropylcarbonyl, cyclobutylcarbonyl, cyclopentylcarbonyl, cyclohexylcarbonyl, cycloheptylcarbonyl or adamantylcarbonyl.

The cycloalkenyl group of the "cycloalkenylcarbonyl group" is preferably a $C_{5-6}$cycloalkenyl group; hence hereinafter the "cycloalkenylcarbonyl group" is called sometimes a "$C_{5-6}$cycloalkenyl-carbonyl group", which is exemplified by cyclopentenylcarbonyl, cyclopentadienylcarbonyl, cyclohexenylcarbonyl or cyclohexadienylcarbonyl.

The aryl group of the "arylcarbonyl group" is preferably a $C_{6-10}$aryl group mentioned above; hence hereinafter the "arylcarbonyl group" is called sometimes a '$C_{6-10}$arylcarbonyl group", which is exemplified by benzoyl or naphthoyl.

The aralkyl group of the "aralkylcarbonyl group" is preferably a $C_{7-9}$aralkyl group; hence hereinafter the "aralkylcarbonyl group" is sometimes called a "$C_{7-19}$aralkylcarbonyl group", which is exemplified by phenylacetyl, phenylpropionyl, $\alpha,\alpha$-diphenylacetyl or $\alpha,\alpha,\alpha$-triphenylacetyl.

The alkyl group of the "alkoxycarbonyl group" includes, in this specification, a $C_{3-10}$cycloalkyl group mentioned above, besides lower alkyl groups having 1-8 carbon atoms; hence hereinafter the "alkoxycarbonyl group" is sometimes called a "$C_{1-10}$alkoxy-carbonyl group", which exemplified by methoxycarbonyl, ethoxycarbonyl, n-propoxycarbonyl, isopropoxycarbonyl, n-butoxycarbonyl, isobutoxycarbonyl, tert-butoxycarbonyl cyclopentyloxycarbonyl, cyclohexyloxycarbonyl or norbornyloxycarbonyl.

The aryloxy group of the "aryloxycarbonyl group" is preferably a $C_{6-10}$aryloxy group mentioned above; hence hereinafter the "aryloxycarbonyl group" is sometimes called a "$C_{6-10}$aryloxy-carbonyl group", which is exemplified by phenoxycarbonyl or naphthyloxycarbonyl.

The aralkyloxy group of the "aralkyloxycarbonyl group" is preferably a $C_{7-19}$aralkyloxy group mentioned above, which is exemplified by benzyloxycarbonyl, benzhydryloxycarbonyl or trityloxycarbonyl.

"Substituted oxycarbonl group" means the above-mentioned $C_{1-10}$alkoxy-carbonyl group, $C_{6-10}$aryloxycarbonyl group or $C_{7-19}$aralkyloxy-carbonyl group.

The alkylthio group of the "alkylthiocarbonyl group" is preferably a $C_{1-6}$alkylthio group mentioned above, hence the "alkylthiocarbonyl group" is hereinafter called sometimes a "$C_{1-6}$alkylthio-carbonyl group", which is exemplified by methylothiocarbonyl, ethylthiocarbonyl, n-propylthiocarbonyl or n-butylthiocarbonyl.

The alkanoyl group of the "alkanoyloxy group" is preferably a $C_{1-6}$alkanoyl group mentioned above; hence the "alkanoyloxy group" is hereinafter called a "$C_{1-6}$alkanoyloxy group, which is exemplified by formyloxy, acetoxy, propionyloxy, butyryloxy, valeryloxy or pivaloyloxy. These alkanoyloxy groups, except formyloxy, are sometimes called a "$C_{2-6}$alkenoyloxy group".

The alkenoyl group of the "alkanoyloxy group" is preferably a $C_{3-5}$alkenoyl group mentioned above; hence the "alkenoyloxy group" is hereinafter called sometimes a "$C_{3-5}$alkenoyloxy group", which is exemplified by acryloyloxy or crotonoyloxy.

The alkyl group of the "monoalkylcarbamoyl group" is preferably a $C_{1-6}$alkyl group mentioned above; hence the "monoalkylcarbamoyl group" is hereinafter sometimes called a "mono-$C_{1-6}$alkylcarbamoyl group", which is exemplified by N-methylcarbamoyl or N-ethylcarbamoyl.

The alkyl group of the "dialkylcarbamoyl group" is preferably a $C_{1-6}$alkyl group; hence the "dialkylcarbamoyl group" is hereinafter sometimes called a "di-$C_{1-6}$ alkylcarbamoyl group", which is exemplified by N,N-dimethylcarbamoyl or N,N-diethylcarbamoyl or N,N-diethylcarbamoyl.

The monoalkylcarbamoyl group of the "monoalkylcarbamoyloxy group" is preferably a mono-$C_{1-6}$alkylcarbamoyl group mentioned above; hence the "monoalkylcarbamoyloxy group" is hereinafter sometimes called a "mono-$C_{1-6}$alkylcarbamoyloxy group", which is exemplified by N-methylcarbamoyloxy or N-ethylcarbamoyloxy.

The dialkylcarbamoyl group of the "dialkylcarbamoyloxy group" is preferably a di-$C_{1-6}$alkylcarbamoyl group mentioned above; hence the "dialkylcarbamoyloxy group" is hereinafter sometimes called a "di-$C_{1-6}$alkylcarbamoyloxy group", which is exemplified by N,N-dimethylcarbamoyloxy or N,N-diethylcarbamoyloxy.

The alkyl group of the "alkylsulfonyl group" is preferably a $C_{1-6}$alkyl group mentioned above; hence the "alkylsulfonyl group" is hereinafter sometimes called a "$C_{1-6}$alkylsulfonyl group", which is exemplified by methanesulfonyl or ethanesulfonyl.

The aryl group of the "arylsulfonyl group" is preferably a $C_{6-10}$aryl group mentioned above; hence the "arylsulfonyl group" is hereinafter sometimes called a "$C_{6-10}$arylsulfonyl group", which is exemplified by, among others, benzenesulfonyl.

The aralkyl group of the "aralkylsulfonyl group" is preferably a $C_{7-19}$aralkyl group mentioned above; hence the "aralkylsulfonyl group" is hereinafter sometimes called a "$C_{7-19}$aralkylsulfonyl group", which is exemplified by phenylmethanesulfonyl or diphenylomethanesulfonyl.

The alkylsulfonyl group of the "alkylsulfonyloxy group" is preferably a $C_{1-6}$alkylsulfonyl group mentioned above; hence the "alkylsulfonyloxy group" is hereinafter sometimes called a "$C_{1-6}$alkylsulfonyloxy group", which is exemplified by methanesulfonyloxy or ethanesulfonyloxy.

The arylsulfonyl group of the "arylsulfonyloxy group" is preferably a $C_{6-10}$arylsulfonyl group; hence the "arylsulfonyloxy group" is hereinafter sometimes called a "$C_{6-10}$arylsulfonyloxy group", which is exemplified by, among others, benzenesulfonyloxy.

The aralkylsulfonyl group of the "aralkylsulfonyloxy group" is preferably a $C_{7-19}$aralkylsulfonyl group mentioned above; hence the "aralkylsulfonyloxy group" is hereinafter sometimes called a "$C_{7-19}$arylsulfonyloxy group", which is exemplified by phenylmethanesulfonyloxy or diphenylmethanesulfonyloxy.

"Amino acid residue" means acyl groups formed by removing hydroxyl group of the carboxyl group of conventional amino acids, which is exemplified by glycyl, alanyl, valyl, leucyl, isoleucyl, seryl, threonyl, cysteinyl, cystinyl, methionyl, aspartyl, glutamyl, lysyl, arginyl, phenylglycyl, phenylalanyl, tyrosyl, histidyl, triptophanyl or prolyl.

"Nitrogen-containing heterocyclic ring" means a 5 to 8 membered ring containing one to several, preferably 1 to 4, nitrogen atoms (optionally oxidized) or condensed ring thereof, which may contain besides nitrogen atoms one to several, preferably 1 to 2 hetero atoms such as oxygen atom or sulfur atom. "Nitrogen-containing heterocyclic group" means a group formed by removing one hydrogen atom bonding to ring-forming carbon atom of the above nitrogen-containing heterocyclic ring.

"Heterocyclic group" means a group formed by removing one hydrogen atom bonding to a carbon atom of a heterocyclic ring, which means a 5 to 8 membered ring containing one to several, preferably 1 to 4 hetero atoms such as nitrogen atom (optionally oxidized), oxygen atom or sulfur atom, or condensed ring thereof, which is exemplified by 2- or 3-pyrrolyl, 3-, 4- or 5- pyrazolyl, 2-, 4- or 5-imidazolyl, 1,2,3- or 1,2,4-triazolyl, 1H- or 2H-tetrazolyl, 2- or 3-furyl, 2-or 3-thienyl, 2-, 4- or 5-oxazolyl, 3-, 4- or 5-isoxazolyl, 1,2,3-oxadiazol-4- or 5-yl, 1,2,4-oxadiazol-3- or 5-yl, 1,2,5- or 1,3,4-oxadiazolyl, 2-, 4- or 5-thiazolyl, 3-, 4- or 5-isothiazolyl, 1,2,3-thiadiazol-4-or 5-yl, 1,2,4-thiadiazol-3-or 5-yl, 1,2,5- or 1,3,4-thiadiazolyl, 2- or 3-pyrrolidinyl, 2-, 3- or 4-pyridyl, 2-, 3- or 4-pyridyl-N-oxide, 3- or 4-pyridazinyl, 3- or 4-pyridazinyl-N-oxide, 2-, 4- or 5-pyrimidinyl, 2-, 4- or 5-pyrimidinyl-N-oxide, pyrazinyl, 2- , 3- or 4-piperidinyl, piperazinyl, 3H -indol-2- or 3-yl, 2-, 3- or 4-pyranyl, 2-, 3- or 4-thiopyranyl, benzopyranyl, quinolyl, pyrido[2,3-d]pyrimidyl, 1,5-, 1,6-, 1,7-, 1,8-, 2,6- or 2,7-naphthylidyl, thieno[2,3-d]-pyridyl, pyrimidopyrimidyl, pyrazinoquinolyl, or benzopyranyl.

Heterocyclic groups of "heterocycle-oxy group", "heterocycle-thio group", "heterocycle-amino group", "heterocycle-carbonyl group", "heterocycle-acetyl group" and "heterocycle-carboxamido group" are all preferably "heterocyclic group" mentioned above.

"Quaternary ammonium group" means a group in which the bonding hand is the unpaired electron located on one of the tertiary nitrogen atoms of the above-mentioned nitrogen-containing heterocyclic rig, and per se quaternarized, necessarily being accompanied with corresponding anion. The quaternary ammonium group is exemplified by oxazolium, thiazolium, isoxazolium, isothiazolium, pyridinium or quinolinium. The anion is exemplified by hydroxide ion, halogenide ion (e.g. chloride ion, bromide ion or iodide ion), sulfate ion, nitrate ion, carbonate ion, organic carboxylate ion (e.g. oxalate ion or trifluoroacetate ion) or organic sulfonate ion (e.g. p-toluenesulfonate ion), the latter two being sometimes intramolecular ones.

The groups bearing asterisk * at the right shoulder are "optionally substituted groups". For example, alkyl* group means "optionally substituted alkyl group". The number of substituents is not restricted to one, two to four, preferably, 2 to 3, which may be the same or different.

"$C_{6-10}$aryl* group", "$C_{7-12}$aralkyl* group", "$C_{6-10}$aryl*oxy group" and "$C_{7-19}$aralkyl*oxy group" are preferably "phenyl* group", "benzyl* group", "phenoxy* group" and "benzyl*oxy group", respectively.

The substituents of "optionally substituted $C_{1-6}$ alkanoyl group" represented by $C_{1-6}$ alkanoyl* group are exemplified by (1) heterocycle*carbonyl group in case of $C_1$ alkanoyl (i.e. formyl) and (2) "substituent $S^1$" described below in case of $C_{2-6}$ alkanoyl group (i.e. acetyl, propionyl, butyryl, isobutyryl valeryl, isovaleryl, pivaloyl, etc.). The "substituent $S^1$" is exemplified by $C_{3-10}$ cycloalkyl* group $C_{5-6}$ cycloalkenyl* group, $C_{6-10}$ aryl* group, hydroxyl group, $C_{1-6}$ alkoxy group, $C_{3-10}$ cycloalkyloxy group, $C_{6-10}$ aryl*oxy group, $C_{7-19}$ aralkyl*oxy group, mercapto group, $C_{1-6}$ alkyl*thio group, amino $C_{1-6}$ alkylthio group, $C_{2-6}$ alkenyl*thio group, $C_{3-10}$ cycloalkylthio group, $C_{6-10}$ aryl*thio group, $C_{7-19}$ aralkyl*thio group, amino group, mono-$C_{1-6}$ alkylamino group, di-$C_{1-6}$ alkylamino group, $C_{3-10}$ cycloalkylamino group, $C_{6-10}$ aryl*amino group, $C_{7-19}$ aralkyl*amino group, cyclic amino* group, halogen atom, nitro group, azido group, cyano group, carboxyl group, acyl+ group, substituted oxycarbonyl group, $C_{1-6}$ alkylthio-carbonyl group, acyl+oxy group, acyl+amino group, acyl+aminoalkylthio group, carbamoyl group, mono-$C_{1-6}$ alkylcarbamoyl group, di-$C_{1-6}$ alkylcarbamoyl group, carbamoyloxy group, mono-$C_{1-6}$ alkoxycarbonyloxy group, di-$C_{1-6}$ alkylcarbamoyloxy group, sulfo group, hydroxysulfonyloxy group, $C_{1-6}$ alkylsulfonyl group, $C_{6-10}$ aryl*sulfonyl group, $C_{7-19}$ aralkyl*sulfonyl group, $C_{1-6}$ alkylsulfonyloxy group, $C_{6-10}$ aryl*sulfonyloxy group, $C_{7-19}$ aralkyl*sulfonyloxy group, ureido* group, sulfamoyl* group, heterocyclic* group, heterocycle*oxy group, heterocycle*thio group, heterocycle*amino-group heterocycle*carbonyl group, heterocycle* carboxamido group or quaternary ammonium* group. The number of these substituents is not restricted to one. But it is preferably one to four, In case there are two or more substituents, these substituents may be the same or different. To state further, two of these substituents may be combined to form C=C double bond or C=N double bond as described below.

The substituents (hereinafter referred to as "substituent $S^2$") of "optionally substituted $C_{3-5}$ alkenoyl group" are exemplified by $C_{3-10}$ cycloalkyl group, $C_{6-10}$ aryl* group, $C_{1-6}$ alkoxy group, $C_{6-10}$ aryl*oxy group, $C_{7-19}$ aralkyl*oxy group, halogen atom, cyano group, carboxyl group, acyl+ group, substituted oxycarbonyl group, acyl+oxy group, heterocyclic* group or quaternary ammonium* group.

The substituents of "optionally substituted $C_{6-10}$ aryl-carbonyl group" represented by $C_{6-10}$ aryl*-carbonyl group as well as "optionally substituted heterocyclic group" represented by heterocycle*-carbonyl group (hereinafter collectively referred to as "substituent $S^3$") are exemplified by $C_{1-6}$ alkyl group, $C_{2-6}$ alkenyl group, $C_{6-10}$ aryl group, $C_{7-12}$ aralkyl group, di-$C_{6-10}$ aryl-methyl group, tri-$C_{6-10}$ aryl-methyl group, hydroxyl group, $C_{1-6}$ alkoxy group, $C_{6-10}$ aryloxy group, $C_{7-19}$ aralkyloxy group, mercapto group, $C_{1-6}$ alkylthio group, $C_{6-10}$ arylthio group, $C_{7-19}$ aralkylthio group, amino group, mono-$C_{1-6}$ alkylamino group, di-$C_{1-6}$ alkylamino group, hydroxy $C_{1-6}$ alkyl group, mercapto $C_{1-6}$ alkyl group, halogen-$C_{1-6}$ alkyl group, carboxy $C_{1-6}$ alkyl group, halogen atom, nitro group, azido group, cyano group, carboxyl group, substituted oxycarbonyl group, acyl+ group, acyl+oxy group, acyl+amino group, carbamoyl group, thiocarbamoyl group, $C_{1-6}$ alkylsulfonyl group, $C_{6-10}$ arylsulfonyl group or $C_{7-19}$ aralkylsulfonyl group.

Among the above-mentioned substituents ($S^1$, $S^2$ and $S^3$) of $C_{1-6}$ alkanoyl group, $C_{3-5}$ alkenoyl group, $C_{6-10}$ aryl-carbonyl group and heterocycle*-carbonyl group, those which are not described below are of the same meaning as afore-mentioned.

The substitutents of the $C_{6-10}$ aryl group of $C_{6-10}$ aryl* group, pheyl group, $C_{6-10}$ aryl*oxy group, phenoxy* group, $C_{6-10}$ aryl*thio group, $C_{6-10}$ aryl*amino group, $C_{6-10}$ aryl*sulfonyl group and $C_{6-10}$ aryl*sulfonyloxy group are also named here by the above-mentioned substituents $S^3$.

The substitutents of the aromatic ring of the $C_{7-12}$ or $C_{7-19}$ aralkyl groups of $C_{7-12}$ aralkyl* group, benzyl* group, $C_{7-19}$ aralkyl*oxy group, benzyl*oxy group, $C_{7-19}$ aralkyl*thio group, $C_{7-19}$ aralkyl*amino group, $C_{7-19}$ aralkyl*sulfonyl group and $C_{7-19}$ aralkyl*sulfonyloxy group are also named here by the above-mentioned substituents $S^3$.

The substituents of the heterocyclic ring of the heterocyclic* group, heterocycle*oxy group, heterocycle*thio group, heterocycle*amino group, heterocycle*acetyl group and heterocycle*carboxamido group are also named here by the above-mentioned substituents $S^3$.

The substituents on the nitrogen-containing heterocyclic ring of quaternary ammonium* group are also named here by the above mentioned substituents $S^3$.

The substituents of the $C_{1-6}$ alkyl group of "optionally substituted $C_{1-6}$ alkyl group" represented by $C_{1-6}$ alkyl* group are also named here by the above-mentioned substituents $S^1$.

The substituents of the "optionally substituted $C_{3-10}$ cycloalkyl group" and "optionally substituted $C_{5-6}$ cycloalkenyl group" representable by $C_{3-10}$ cycloalkyl group and $C_{5-6}$ cycloalkenyl* group are also named here by the above-mentioned substituents $S^3$.

The substituents of the $C_{1-6}$ alkylthio groups of "optionally substituted $C_{1-6}$ alkylthio group" representable by $C_{1-6}$ alkyl*thio group (these substitutents are hereinafter referred to as "substituent $S^4$") are exemplified by hydroxyl group, $C_{1-6}$ alkoxy group, $C_{3-10}$ cycloalkyloxy group, $C_{6-10}$ aryl*oxy group, $C_{7-19}$ aralkyl*oxy group, mercaptos group, $C_{1-6}$ alkylthio group, $C_{3-10}$ cycloalkylthio group, $C_{6-10}$ aryl*thio group, $C_{7-19}$ aralkyl*thio group, amino group, mono-$C_{1-6}$ alkylamino group, di-$C_{1-6}$ alkylamino group, cyclic amino* group, halogen atom, cyano group, carboxyl group, carbamoyl group, acyl+oxy group, sulfo group, or quaternary ammonium*group.

The substituents of the $C_{2-6}$ alkenylthio group of "optionally substituted $C_{2-6}$ alkenylthio group" representable by $C_{2-6}$ alkenyl*thio group (these substituents are hereinafter referred to as "substituent $S^5$") are exemplified by halogen atom, cyano group, carboxy group, carbamoyl group, mono-$C_{1-6}$ alkylcarbamoyl group, di-$C_{1-6}$ alkylcarbamoyl group or thiocarbamoyl group.

"Acyl+group" means the above-mentioned $C_{1-6}$ alkanoyl group, $C_{6-10}$ aryl*carbonyl group, $C_{7-19}$ aralkyl*-carbonyl group, heterocycle*carbonyl group or heterocycle*acetyl group. Representable acyl+ groups are exemplified by formyl, acetyl, propionyl, n-butyryl, isobutyryl, valeryl, pivaloyl, n-hexanoyl, chloroacetyl, dichloroacetyl, trichloroacetyl, 3-oxobutyryl, 4-chloro-3-oxobutyryl, 3-carboxypropionyl, 4-carboxybutyryl, 3-ethoxycarbamoylpropionyl, benzoyl, naphthoyl, p-methylbenzoyl, p-hydroxybenzoyl, p-methoxybenzoyl, p-chlorobenzoyl, p-nitrobenzoyl, o-carboxybenzoyl, o-(ethoxycarbonylcarbamoyl)benzoyl, o-(ethoxycarbonylsulfamoyl)benzoyl, phenylacetyl, p-methylphenylacetyl, p-hydroxyphenylacetyl, p-methoxyphenylacetyl, 2,2-diphenylacetyl, 2-thienylcarbonyl, 2-furylcarbonyl, 2-, 4- or 5-thiazolylacetyl, 2- or 3-thienylacetyl, 2- or 3-furylacetyl, 2-amino-4- or 5-thiazolylacetyl or 5-amino-3-thiadiazolylacetyl.

The acyl+ group of "acyl+oxy group and "acyl+amino group" means the above-mentioned acyl+ group. Therefore, "acyl+oxy group" is exemplified by formyloxy, acetoxy, pripionyloxy, butyryloxy, valeryloxy, pivaloyloxy, chloroacetoxy, dichloroacetoxy, trichloroacetoxy, 3-oxobutyryloxy, 4-chloro-3-oxobutyryloxy, 3-carboxylpropionyloxy, 4-carboxybutyryloxy, 3-ethoxycarbamoylpropionyloxy, benzoyloxy, naphthoyloxy, p-methylbenzoyloxy, p-methoxybenzoyloxy, p-chlorobenzoyloxy, o-carboxybenzoyloxy, o-(ethoxycarbonylcarbamoyl)benzoyloxy, o-(ethoxycarbonylsulfamoyl)benzoyloxy, phenylacetyloxy, p-methylphenylacetyloxy, p-methoxyphenylacetyloxy, p-chlorophenylacetyloxy, 2,2-diphenylacetyloxy, thienylcarbonyloxy, furylcarbonyloxy, thiazolylacetyloxy, thienylacetyloxy or furylacetyloxy, and "acyl+amino group" is exemplified by acetamido ($CH_3CONH$-), benzamido ($C_6H_5CONH$-), phenylacetamido ($C_6H_5CH_2CONH$-) or 2-thienylacetamido

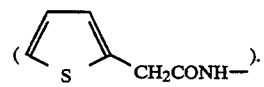

The acyl+amino group and alkylthio group of "acyl+aminoalkylthio group" mean respectively the above-mentioned acyl+amino group and $C_{1-6}$ alkylthio group, hence such "acyl+amino $C_{1-6}$ alkylthio group" being exemplified by acetamidomethylthio or 2-acetamidoethylthio.

"Arylacyl+ group" is preferably "$C_{6-10}$ aryl-acyl+ group", which is exemplified by benzoyl, phthaloyl, naphthoyl or phenylacetyl.

"Arylacyl+oxy group" is preferably "$C_{6-10}$ arylacyl+oxy group", as exemplified by benzoyloxy, naphthoyloxy or phenylacetyloxy.

The substituents of the ureido group of "optionally substituted ureido group" represented by "ureido* group" are exemplified by $C_{1-6}$ alkyl group, $C_{6-10}$ aryl* group, $C_{7-19}$ aralkyl* group, acyl+ group, carbamoyl group, sulfo group (which may form a salt with e.g. sodium or potassium), sulfamoyl group or amidino group.

The substituents of the sulfamoyl group of "optionally substituted sulfamoyl group" represented by "sulfamoyl* group" are exemplified by $C_{1-6}$ alkyl group or amidino group.

The substituents of "optionally substituted carbamoyl group" representable by "carbamoyl* group" and "carbamoyl*oxy group" are exemplified by $C_{1-6}$ alkyl group, $C_{6-10}$ aryl* group, $C_{7-12}$ aralkyl* group or acyl+ group, including the case where the nitrogen atom of carbamoyl group is the ring-forming nitrogen atom of the nitrogen-containing heterocyclic ring.

The substitutents of "optionally substituted thicarbamoyl group" represented by "thiocarbamoyl* group" are exemplified by $C_{1-6}$ alkyl group, $C_{6-10}$ aryl* group, $C_{7-12}$ aralkyl* group or acyl+ group, including the case where the nitrogen atom of a thiocarbamoyl group is the ring-forming nitrogen atom of the nitrogen-containing heterocyclic ring.

The substituents of the cyclic amino group of the "optionally substituted cyclic amino group" represented by "cyclic amino* group" (these substituents are hereinafter referred to as "substituent $S^6$") are exemplified by $C_{1-6}$ alkyl group, $C_{2-6}$ alkenyl group, $C_{3-10}$ cycloalkyl group, $C_{6-10}$ aryl* group, $C_{7-12}$ aralkyl* group, di-$C_{6-10}$ aryl-methyl group, tri-$C_{6-10}$ aryl-methyl group, hydroxyl group, $C_{1-6}$ alkoxy group, $C_{6-10}$ aryl*oxy group, $C_{7-19}$ aralkyl*oxy group, mercapto group, $C_{1-6}$ alkylthio group, $C_{6-10}$ aryl*thio group, $C_{7-19}$ aralkyl*thio group, amino group, mono-$C_{1-6}$ alkylamino group, di-$C_{1-6}$ alkylamino group, $C_{6-10}$ aryl*amino group, $C_{7-19}$ aralkyl*amino group, halogen atom, nitro group, azido group, oxo group, thioxo group, cyano group, carboxyl group, acyl+ group, substituted oxycarbonyl group, acyl+oxy group, acyl+amino group, carbamoyl group, carbamoyloxy group, thiocarbamoyl group or sulfo group.

The formyl group substituted with the heterocycle*-carbonyl group mentioned above as one of the $C_{1-6}$ alkanoyl* groups is an acyl group having a formula of heterocycle*—CO—CO—, and the heterocyclic* group is also mentioned here as one exemplified above, but preferably, an optionally substituted oxazolyl group, thiazolyl group, oxadiazolyl group or thiadiazolyl group, for example. These heterocycle*—CO—CO— groups are exemplified by 2-(2-, 4- or 5-oxazolyl)-2-(2-, 4- or 5-thiazolyl)-2-oxoacetyl, 2-(2-amino-4-thiazolyl)-2-oxoacetyl, 2-(1,2,4-oxadiazol-3- or 5-yl)-2-oxoacetyl, 2-(1,2,4-thiadiazol-3- or 5-yl)-2-oxoacetyl or 2-(5-amino-1,2,4-thiadiazol-3-yl)-2-oxoacetyl.

The $C_{2-6}$ alkanoyl* group is most preferably a substituted acetyl group. The number of substituents of the substituted acetyl group is 1–3, and, as these substituents, "substituent $S^1$" mentioned above as substituents of $C_{1-6}$ alkanoyl groups are also mentioned here. When the number of substituents is 2–3, these substituents may be the same or different, and two of them may be combined to form a double bond.

A detailed description about the substituents $R^1$, and $R^3$ follows.

$R^1$ stands for an optionally protected amino group. In the field of synthesis of β-lactam and peptide, protecting groups of amino group have been sufficiently studied, and the methods of protection and deprotection have already been established. In the present invention as well, any of those known amino-protecting groups may suitably be employed. As such amino-protecting groups, there may be mentioned for example $C_{1-6}$ alkanoyl* group, $C_{3-5}$ alkenoyl* group, $C_{6-10}$ aryl*carbonyl group, phthaloyl group, heterocycle*carbonyl group, $C_{1-6}$ alkyl*sulfonyl group, camphorsulfonyl group, $C_{6-10}$ aryl*sulfonyl group, substituted oxycarbonyl group, carbamoyl* group, carbamoyloxy* group, thiocarbamoyl* group, $C_{6-10}$ aryl*methyl group, di-$C_{6-10}$ aryl*methyl group, tri-$C_{6-10}$ aryl*methyl group, $C_{6-10}$ aryl*methylene group, $C_{6-10}$ aryl*thio group, substituted silyl group or 2-$C_{1-10}$ alkoxy-carbonyl-1-methyl-1-ethenyl group.

As "$C_{1-6}$ alkanoyl* group", there may concretely be mentioned here formyl, acetyl, propionyl, butyryl, valeryl, pivaloyl, succinyl, glutaryl, monochloroacetyl, dichloroacetyl, trichloroacetyl, monobromoacetyl, monofluoroacetyl, difluoroacetyl, trifluoroacetyl, monoiodoacetyl, 3-oxobutyryl, 4-chloro-3-oxobutyryl, phenylacetyl, p-chlorophenylacetyl, phenoxyacetyl or p-chlorophenoxyacetyl. As "$C_{3-5}$ alkenoyl* group", there may concretely be mentioned here acryloyl, crotonoyl, maleoyl, cinnamoyl, p-chlorocinnamoyl or β-phenylcinnamoyl.

As "$C_{6-10}$ aryl*carbonyl group", there may be mentioned, for example, benzoyl, naphthoyl, p-toluoyl, p-tert-butylbenzoyl, p-hydroxybenzoyl, p-methoxybenzoyl, p-tert-butoxybenzoyl, p-chlorobenzoyl or p-nitrobenzoyl.

As the heterocycle*carbonyl group, there may be mentioned those as described hereinafter.

As "$C_{1-6}$ alkyl*sulfonyl group", there may be mentioned, for example, methanesulfonyl or ethanesulfonyl.

As "$C_{6-10}$ aryl*sulfonyl group", there may be mentioned here benzenesulfonyl, naphthalenesulfonyl, p-toluenesulfonyl, p-tert-butylbenzenesulfonyl, p-methoxybenzenesulfonyl, p-chlorobenzenesulfonyl or p-nitrobenzenesulfonyl, for example.

"Substituted oxycarbonyl group" means not only the above-mentioned one, i.e. $C_{1-10}$ alkoxy-carbonyl group, $C_{6-10}$ aryloxy-carbonyl group or $C_{7-19}$ aralkyloxycarbonyl group, but includes here one having substituents, and therefore there may be mentioned here methoxycarbonyl, ethoxycarbonyl, n-propoxycarbonyl, isopropoxycarbonyl, n-butoxycarbonyl, tert-butoxycarbonyl, cyclohexyloxycarbonyl, norbornyloxycarbonyl, phenoxycarbonyl, naphthyloxycarbonyl, benzyloxycarbonyl, methoxymethyloxycarbonyl, acetylmethyloxycarbonyl, 2-trimethylsilylethoxycarbonyl, 2-methanesulfonylethoxycarbonyl, 2,2,2-trichloroethoxycarbonyl, 2-cyanoethoxycarbonyl, p-methylphenoxycarbonyl, p-methoxyphenoxycarbonyl, p-chlorophenoxycarbonyl, p-methylbenzyloxycarbonyl, p-methoxybenzyloxycarbonyl, p-chlorobenzyloxycarbonyl, p-nitrobenzyloxycarbonyl, benzhydryloxycarbonyl, cyclopropyloxycarbonyl, cyclopentyloxycarbonyl or cyclohexyloxycarbonyl, for example.

"Carbamoyl* group" is exemplified here by carbamoyl, N-methylcarbamoyl, N-ethylcarbamoyl, N,N-dimethylcarbamoyl, N,N-diethylcarbamoyl, N-phenylcarbamoyl, N-acetylcarbamoyl, N-benzoylcarbamonyl or N-(p-methoxyphenyl)carbamoyl.

"Carbamoyl*oxy group" is exemplified here by carbamoyloxy, N-methylcarbamoyloxy, N,N-dimethylcarbamoyloxy, N-ethylcarbamoyloxy or N-phenylcarbamoyloxy.

"Thiocarbamoyl* group" is exemplified here by thiocarbamoyl, N-methylthiocarbamoyl or N-phenylthiocarbamoyl, for example.

"$C_{6-10}$ aryl*methyl group" is exemplified by benzyl, naphthylmethyl, p-methylbenzyl, p-methoxybenzyl, p-chlorobenzyl or p-nitrobenzyl.

"Di-$C_{6-10}$ aryl*methyl group" is exemplified by benzyhydryl or di-(p-tolyl)methyl.

"Tri-$C_{6-10}$ aryl*methyl group" is exemplified by trityl or tri-(p-tolyl)methyl.

"$C_{6-10}$ aryl*methylene group" is exemplified by benzylidene, p-methylbenzylidene or p-chlorobenzylidene.

"$C_{6-10}$ aryl*thio group" is exemplified by o-nitrophenylthio.

"Substituted silyl group" means a silyl group, together with the amino group to be protected, representable by the general formula; $R^6R^7R^8SiNH$, $(R^6R^7R^8Si)_2N$ or

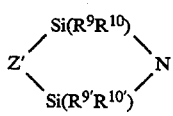

[wherein $R^6$, $R^7$, $R^8$, $R^9$, $R^{10}$, $R^{9'}$ and $R^{10'}$ are the same or different and stand for $C_{1-6}$ alkyl group or $C_{6-10}$ aryl* group, and Z' stands for $C_{1-3}$ alkylene group e.g. methylene, ethylene or propylene], which is exemplified by trimethylsilyl, tert-butyldimethylsilyl or —$Si(CH_3)_2CH_2CH_2Si(CH_3)_2$—.

The $C_{1-10}$ alkoxy-carbonyl group of "2-$C_{1-10}$ alkoxycarbonyl-1-methyl-1-ethenyl group" is preferably one of those mentioned in the foregoing. Hence, the 2-$C_{1-10}$ alkoxycarbonyl-1-methyl-1-ethenyl group is exemplified by 2-methoxycarbonyl-1-methyl-1-ethenyl, 2-ethoxycarbonyl-1-methyl-1-ethenyl, 2-tert-butoxycarbonyl-1-methyl-1-ethenyl, 2-cyclohexyloxycarbonyl-1-methyl-1-ethenyl or 2-norbornyloxycarbonyl-1-methyl-1-ethenyl.

the symbol $R^3$ stands for hydrogen atom or a substituted hydrocarbon residue. The hydrocarbon residue may be exemplified by a $C_{1-6}$ alkyl group, $C_{2-6}$ alkenyl group, $C_{2-6}$ alkynyl group, $C_{3-10}$ cycloalkyl group or $C_{5-6}$ cycloalkenyl group, especially preferably, $C_{1-3}$ alkyl group or a substituted $C_{1-3}$ alkyl group. The $C_{1-6}$ alkyl group is, also here, preferably one of those described in the foregoing and may be exemplified by methyl, ethyl, n-propyl, isopropyl, n-butyl, isobutyl, sec-butyl, tert-butyl, n-pentyl or n-hexyl, especially preferably, methyl, ethyl and n-propyl. The $C_{2-6}$ alkenyl group is, also here, preferably one of those described in the foregoing and may be exemplified by vinyl, allyl, isopropenyl, methallyl, 1,1-dimethylallyl, 2-butenyl or 3-butenyl. The $C_{2-6}$ alkynyl group may be exemplified by ethylnyl, 1-propynyl, 2-propynyl or propargyl. The $C_{3-10}$ cycloalkyl group is, also here, preferably the above-mentioned $C_{3-8}$ cycloalkyl group and may be exemplified by cyclopropyl, cyclobutyl, cyclopentyl, cyclohexyl, cycloheptyl or adamantyl. The $C_{5-6}$ cycloalkenyl group may be exemplified by 2-cyclopentyl, 3-cyclopentenyl, 2-cyclohexenyl, 3-cyclohexenyl, cyclopentadienyl or cyclohexadienyl. Substituents of these hydrocarbon residues may be one to three groups exemplified by a hydroxyl group, $C_{1-6}$ alkyl group, $C_{2-6}$ alkenyl group, $C_{2-6}$ alkynyl group, $C_{3-10}$ cycloalkyl group, $C_{5-6}$ cycloalkenyl group, $C_{6-10}$ aryl group, $C_{7-19}$ aralkyl group, heterocyclic group, $C_{1-6}$ alkoxy group, $C_{3-10}$ cycloalkoxyloxy group, $C_{6-10}$ aryloxy group, $C_{7-19}$ aralkyloxy group, heterocycle-oxy group, mercapto group, $C_{1-6}$ alkythio group, $C_{3-10}$ cycloalkylthio group, $C_{6-10}$ arylthio group, $C_{7-19}$ aralkylthio group, heterocyclethio group, amino group, mono-$C_{1-6}$ alkylamino group, di-$C_{1-6}$ alkylamino group, tri-$C_{1-6}$ alkylammonium group, $C_{3-10}$ cycloalkylamino group, $C_{6-10}$ arylamino group, $C_{7-19}$ aralkylamino group, heterocycle-amino group, cyclic amino group, azido group, nitro group, halogen atom, cyano group, carboxyl group, $C_{1-10}$ alkoxycarbonyl group, $C_{6-10}$ aryloxy-carbonyl group, $C_{7-19}$ aralkyloxy-carbonyl group, $C_{6-10}$ aryl-acyl+ group, $C_{1-6}$ alkanoyl group, $C_{3-5}$ alkenoyl group, $C_{6-10}$ aryl-acyl+oxy group, $C_{2-6}$ alkanoyloxy group, $C_{3-5}$ alkenoyloxy group, carbamoyl* group, thiocarbamoyl* group, carbamoyl*oxy group, phthalimido group, $C_{1-6}$ alkanoylamino group, $C_{6-10}$ aryl-acyl+amino group, carboxyamino group, $C_{1-10}$ alkoxy-carboxamido group, $C_{6-10}$ aryloxy-carboxamido group or $C_{7-19}$ aralkyloxy-carboxamido group, and two or three of them, same or different, may be present. As substituents of the hydrocarbon residues, more specifically stating, the $C_{1-6}$ alkyl group stands for the above-mentioned groups, i.e. methyl, ethyl, n-propyl, isopropyl, n-butyl, isobutyl, sec-butyl, tert-butyl, n-pentyl or n-hexyl, the $C_{2-6}$ alkenyl group stands for the above-mentioned groups, i.e. vinyl, allyl, isopropenyl, methallyl, 1,1-dimethyallyl, 2-butenyl or 3-butenyl, the $C_{2-6}$ alkynyl group stands for the above-mentioned groups, i.e. ethynyl, 1-propynyl, 2-propynyl or propargyl, the $C_{3-10}$ cycloalkyl group stands for the above-mentioned groups, i.e. cyclopropyl, cyclobutyl, cyclopentyl, cyclohexyl, cycloheptyl or adamantyl, the $C_{5-6}$ cycloalkenyl group stands for the above-mentioned groups, i.e. cyclopropenyl, 2-cyclopentenyl, 3-cyclopentenyl, 2-cyclohexenyl, 3-cyclohexenyl, cyclopentadienyl or cyclohexadienyl, the $C_{6-10}$ aryl group stands for the above-mentioned groups, i.e. phenyl, naphthyl or biphenylyl, the $C_{7-19}$ aralkyl group stands for the above-mentioned groups, i.e. benzyl, 1-phenylethyl, 2-phenylethyl, phenylpropyl, naphthylmethyl or benzhydryl, the $C_{1-6}$ alkoxy group stands for the above-mentioned groups, i.e. methoxy, ethoxy, n-propoxy, isopropoxy, n-butoxy, tert-butoxy, n-pentyloxy or n-hexyloxy, the $C_{3-10}$ cycloalkyloxy group stands for the above-mentioned groups, i.e. cyclopropyloxy or cyclohexyloxy, the $C_{6-10}$ aryloxy group stands for the above-mentioned groups, i.e. phenoxy or naphthyloxy, the $C_{7-19}$ aralkyloxy group stands for the above-mentioned groups, i.e. benzyloxy, 1-phenylethyloxy, 2-phenylethyloxy or benzhydryloxy, the $C_{1-6}$ alkylthio group stands for the above-mentioned groups, i.e. methylthio, ethylthio, n-propylthio or n-butylthio, the $C_{3-10}$ cycloalkylthio group stands for the above-mentioned groups, i.e. cyclopropylthio or cyclohexylthio, the $C_{6-10}$ arylthio group stands for the above-mentioned groups, i.e. phenylthio or naphthylthio, the $C_{7-19}$ aralkylthio group stands for the above-mentioned groups, i.e. benzylthio, phenylethylthio or benzhydrylthio, the mono-$C_{1-6}$ alkylamino group stands for the above-mentioned groups, i.e. methylamino, ethylamino, n-propylamino, or n-butylamino, the di-$C_{1-6}$ alkylamino group stands for the above-mentioned groups, i.e. dimethylamino, diethylamino, methylethylamino, di-(n-propyl)amino or di-(n-butyl)amino, the tri-$C_{1-6}$ alkylammonium group stands for the above-mentioned groups, i.e. trimethylammonium or triethylammonium, the $C_{3-10}$ cycloalkylamino group stands for the above-mentioned groups, i.e. cyclopropylamino, cyclopentylamino or cyclohexylamino, the $C_{6-10}$ arylamino group stands for the above-mentioned groups, i.e. anilino or N-methylanilino, the $C_{7-19}$ aralkylamino group stands for the above-mentioned groups, i.e. benzylamino, 1-phenylethylamino, 2-phenylethylamino or benzhydrylamino, the cyclic amino group stands for the above-mentioned groups, i.e. pyrrolidino, piperidino, piperazino, morpholino or 1-pyrrolyl, the halogen atom stands here for fluorine, chlorine, bromine or iodine, the $C_{1-10}$ alkoxy-carbonyl group stands for the above-mentioned groups, i.e. methoxycarbonyl, ethoxycarbonyl, n-propoxycarbonyl, isopropoxycarbonyl, n-butoxycarbonyl, isobutoxycarbonyl, tert-butoxycarbonyl, cyclopentyloxycarbonyl, cyclohexyloxycarbonyl or norbornyloxycarbonyl, the $C_{6-10}$ aryloxy-carbonyl group stands for the above-mentioned groups, i.e. phenoxycarbonyl or naphthyloxycarbonyl, he $C_{7-19}$ aralkyloxy-carbonyl group stands for the above-mentioned groups, i.e. benzyloxycarbonyl or benzyhydryloxycarbonyl, the $C_{6-10}$ aryl-acyl+ group stands for the above-mentioned groups, i.e. benzoyl, naphthoyl, phthaloyl or phenylacetyl, the $C_{1-6}$ alkanoyl group stands for the above-mentioned groups, i.e. formyl acetyl, pripionyl, butyl, valeryl, pivaloyl, succinyl or glutaryl, the $C_{3-5}$ alkenoyl group stands for the above-mentioned groups, i.e. acryloyl, crotonoyl or maleoyl, the $C_{6-10}$ aryl-acyl+oxy group stands for the above-mentioned groups, i.e. benzoyloxy, naphthoyloxy or phenylacetoxy, the $C_{2-6}$ alkanoyloxy group stands for the above-mentioned groups, i.e. acetoxy, propionyloxy, butyryloxy, valeryloxy or pivaloyloxy, the $C_{3-5}$ alkenoyloxy group stands for the above-mentioned groups, i.e. acryloyloxy or crotonoyloxy, the carbamoyl* group stands for the above-mentioned groups, i.e. carbamoyl, N-methylcarbamoyl, N-ethylcarbamoyl, N,N-dimethylcarbamoyl, N-ethylcarbamoyl, N,N-diethylcarbamoyl, N-phenylcarbamoyl, N-acetylcarbamoyl, N-benzoylcarbamoyl, N-(p-methoxyphenyl)carbamoyl and, in addition, pyrrolidinocarbonyl, piperidinocarbonyl, piperazinocarbonyl or morpholinocarbonyl, the thiocarbamoyl* group stands for the above-mentioned groups, i.e. thiocarbamoyl, N-methylthiocarbamoyl or N-phenylthiocarbonyl, the carbamoyl*oxy group stands for the above-mentioned group, i.e. carbamoyloxy, N-methylcarbamoyloxy, N,N-dimethylcarbamoyloxy, N-ethylcarbamoyloxy or N-phenylcarbamoyloxy, "$C_{1-6}$ alkanoylamino group" stands for e.g. acetamido, propionamido, butyramido, valeramido or pivalamido, "$C_{6-10}$ aryl-acryl+amino group" stands for e.g. benzamido, napthoylamido or phthalimido, "$C_{1-10}$ alkoxy-carboxamido group" stands for e.g. methoxycarboxamido ($CH_3OCONH-$), ethoxycarboxamido or tert-butoxycarboxamido, "$C_{6-10}$ aryloxy-carboxamido group" stands for e.g. phenoxycarboxamido ($C_6H_5OCONH-$), and "$C_{7-19}$ aralkyloxy-carboxamido group" stands for e.g. benzyloxycarboxamido ($C_6H_5CH_2OCONH-$) or benzhydroloxycarboxamido. The heterocyclic group, heterocyclic groups of heterocycle-oxy group, heterocycle-thio group and heterocycle-amino group are also here such groups as formed by removing one hydrogen atom bonding to the carbon atom of the heterocyclic ring. Such a heterocyclic ring as above may be exemplified by a 5- to 8-membered ring containing one to several, preferably 1 to 4, hetero atoms such as an oxygen atom or sulfur atom. Such heterocyclic groups may be exemplified also here by those concretely mentioned above, including 2-pyrrolyl. Hence, "heterocycle-oxy group" is exemplified by thiazolyloxy, and "heterocycle-thio group" is exemplified by thiazolylthio, and "heterocycle-amino group" is exemplified by thiazolylamino or thiadiazolylamino. Preferably substituted hydrocarbon residues are $C_{1-3}$ alkyl groups ($C_{1-3}$ alkyl group means methyl, ethyl, n-propyl, isopropyl, etc.) substituted by 1 to 3 groups such as hydroxyl group, cycloalkyl group, alkoxy group, alkylthio group, amino group, trialkylammonium group, halogen atom, carboxyl group, alkoxycarbonyl group, carbamoyl group, cyano group, azido group or heterocyclic group, which may concretely be mentioned, among many others, cyclopropylmethyl, methoxymethyl, ethoxymethyl, 1-methoxyethyl, 2-methoxyethyl, 1-ethoxyethyl, 2-hydroxyethyl, methylthiomethyl, 2-aminoethyl, 2-(trimethylammonium)ethyl, 2-(triethylammonium)ethyl, fluoromethyl, difluoromethyl, trifluoromethyl, 2-fluoroethyl, 2,2-difluoroethyl, chloromethyl, 2-chloroethyl, 2,2-dichloroethyl, 2,2,2-trichloroethyl, 2-bromoethyl, 2-iodethyl, 2,2,2-trifluoroethyl, carboxymethyl, 1-carboxymethyl, 2-carboxyethyl, 2-carboxypropyl, 3-carboxypropyl, 1-carboxybutyl, cyanomethyl, 1-carboxy-1-methylethyl, methoxycarbonylmethyl, ethoxycarbonylmethyl, tert-butoxycarbonylmethyl, 1-methoxycarbonyl-1-methylethyl, 1-ethoxycarbonyl-1-methylethyl, 1-tert-butoxycarbonyl-1-methylethyl, 1-benzyloxycarbonyl-1-methylethyl, 1-pivaloyloxycarbonyl-1-methylethyl, carbamoylmethyl, 2-azidoethyl, 2-(pyrazolyl)ethyl, 2-(imidazolyl)ethyl, 2-(2-oxopyrrolidin-3-yl)ethyl or 2-amino-4-thiazolylmethyl. Most preferable ones among the above-exemplified hydrocarbon residues are straight-chain $C_{1-3}$ alkyl groups, e.g. methyl, ethyl and n-propyl; straight-chain or branched $C_{1-3}$ alkyl groups substituted by 1 to 3 groups such as halogen atom, hydroxy group, alkoxy group, carboxyl group, alkoxycarbonyl group or cyano group, e.g. 2-fluoroethyl, 2-chloroethyl, 2-hydroxyethyl, 2-methoxyethyl, cyanomethyl, carboxymethyl, tert-butoxycarbonylmethyl, 1-carboxy-1-methylethyl or 1-tert-butoxycarbonyl-1-methylethyl; allyl group and propargyl group. Supposing here that the symbol $R^{3'}$ should stand for most preferably hydrocarbon residues exemplified above or a hydrogen atom, the compound [I] of this invention is shown by the following structural formula:

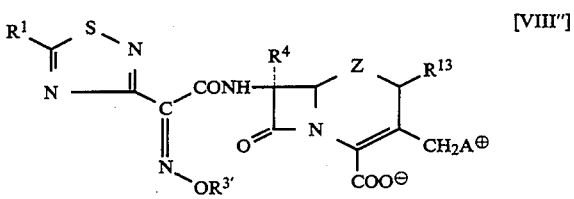

[wherein symbols are of the same meaning as defined above].

Preferable examples of the acyl group shown by the formula:

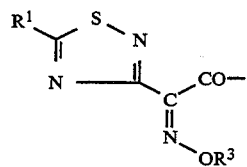

are 2-(5-amino-1,2,4-thiadiazol-3-yl)-2(Z)-Y-(hydroxyimino)acetyl, 2-(5-amino-1,2,4-thiadiazol-3-yl)-2(Z)-(methoxyimino)acetyl, 2-(5-amino-1,2,4-thiadiazol-3-yl)-2(Z)-(ethoxyimino)acetyl, 2-(5-amino-1,2,4-thiadiazol-3-yl)-2(Z)-(ethoxyimino)acetyl, 2-(5-amino-1,2,4-thiadiazol-3-yl)-2(Z)[(2-fluoroethyl)oxyimino]acetyl, 2-(5-amino-1,2,4-thiadiazol-3-yl)-2(Z)-carboxymethyloxyimino)acetyl, 2-(5-amino-1,2,4-thiadiazol-3-yl)-2(Z)-[(1-carboxyl-1-methylethyl)oxyimino]acetyl, 2-(5-amino-1,2,4-thiadiazol-3yl)-2(Z)-[(1-tert-butoxycarbonyl-1-methylethyl)oxyimino]acetyl.

The substituent $R^4$ in the compound [I] of this invention stands for hydrogen atom, methoxy group or formamido group (HCONH—).

The substituent $R^{13}$ in the compound [I] of this invention stands for hydrogen atom, methyl group, hydroxyl group or halogen atom. The halogen atom means here fluorine, chlorine, bromine or iodine.

In the compound [I] of this invention, the substituent $A^\oplus$ stands for imidazolium-1-yl group which forms a condensed ring at 2,3- or 3,4-position. Condensed ring means an imidazole ring having a 5- to 6-membered aromatic heterocyclic ring condensed therewith, and it may optionally be further condensed with another aromatic ring or aromatic heterocyclic ring. The mark ⊕ attached to the right shoulder of the substituent A means that A has a monovalent positive electric charge. The optionally substituted imidazolium-1-yl group ($A^\oplus$) forming the condensed ring at the 2,3- or 3,4-position is shown by the general formula [$A^1$] or [$A^2$];

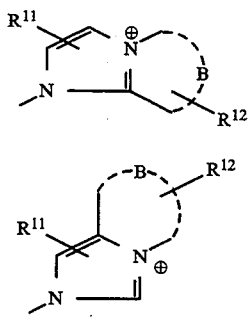

wherein B stands for a group forming an 5- to 6-membered aromatic heterocyclic ring which may be condensed with another aromatic ring or aromatic heterocyclic ring, $R^{11}$ stands for hydrogen atom or a substituent (or substitutents) on the imidazole ring and $R^{12}$ stands for hydrogen atom or a substituent (or substituents) on the ring which is condensed with the imidazole ring. B consists of carbon atom, nitrogen atom, oxygen atom and/or sulfur atom, and, among them, a carbon atom combines with on hydrogen atom or one substituent, or forms another condensed ring together with an adjacent carbon atom. The $A^1$ group may be embodied as follows, for example;

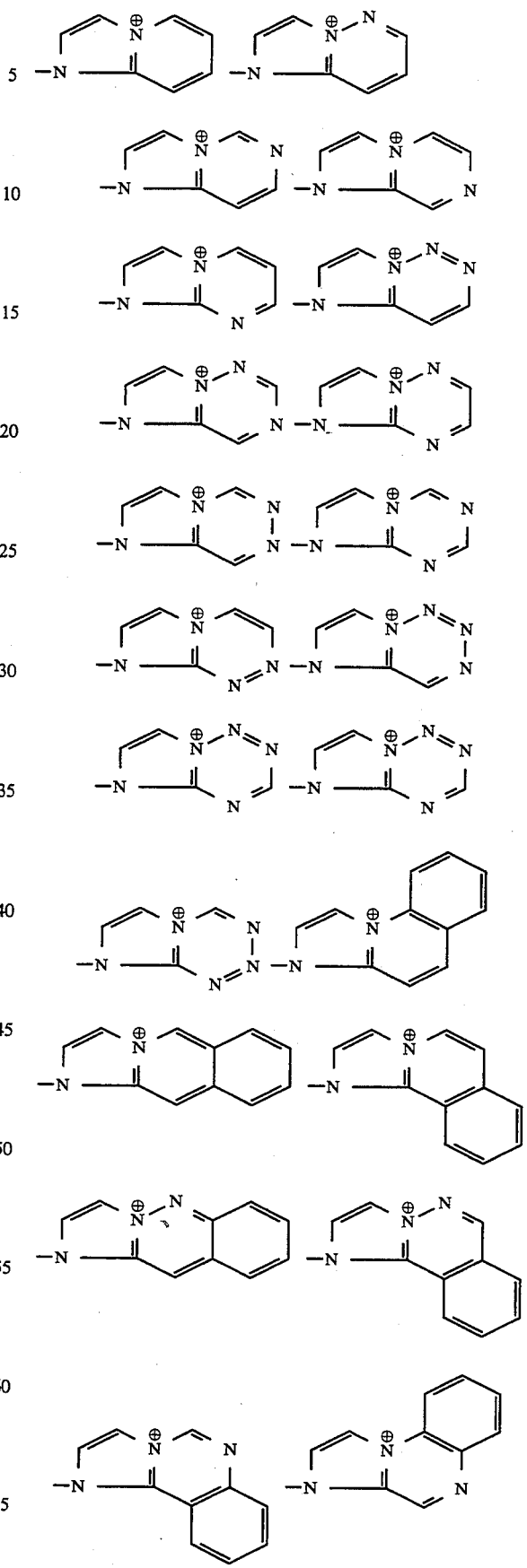

-continued
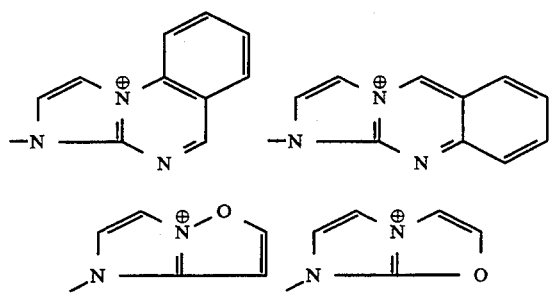
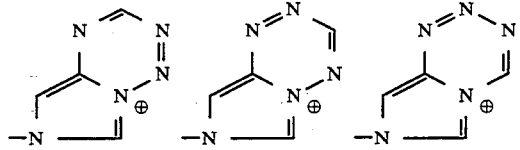
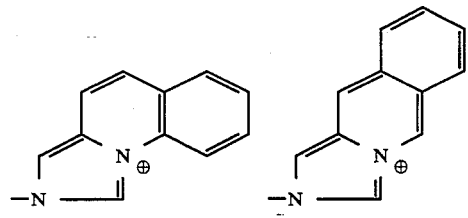
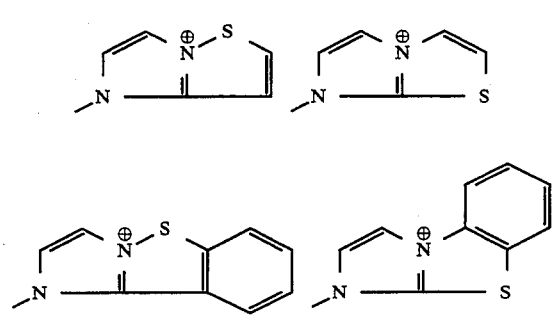
The A² group may be embodied as follows, for example;
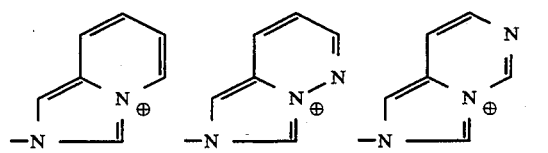
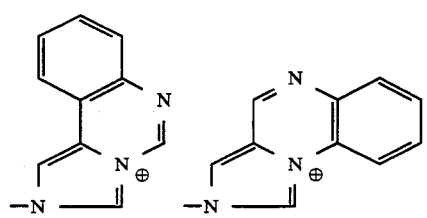
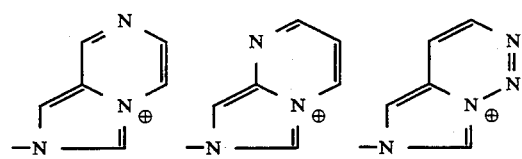
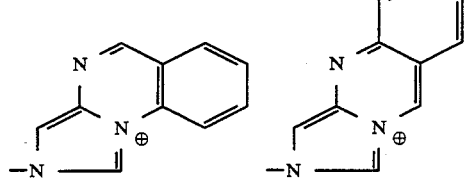
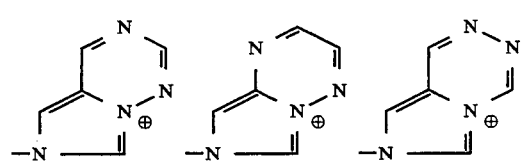
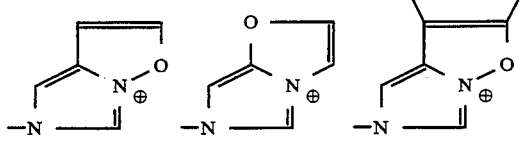
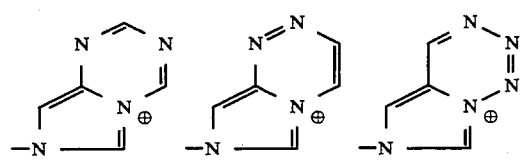
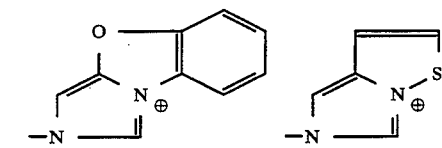

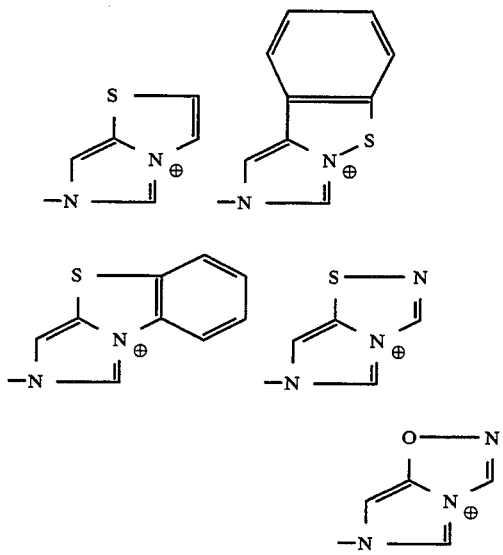

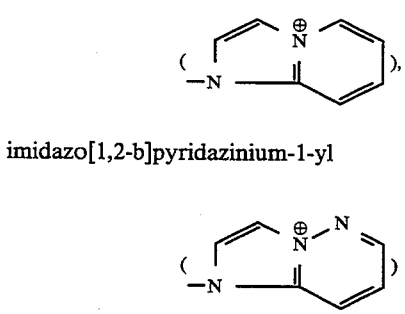

Among these groups, especially preferable are imidazo[1,2-a]pyridinium-1-yl

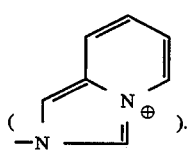

imidazo[1,2-b]pyridazinium-1-yl

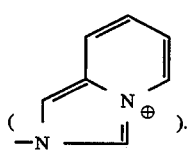

and imidazo[1,5-a]pyridinium-2-yl

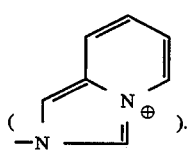

In the above-mentioned formulae [A¹] and [A²] as well as in the A¹ groups and A² groups embodied as above, the positive electric charge A⊕ is applied, for convenience sake, to the nitrogen atom at the 3-position of imidazole, but there may be a case where the said quaternary nitrogen is that of the nitrogen atom at the 1-position. Further, there may be cases where the monovalent positive electric charge is delocalized at the imidazole ring, or even delocalized on the entire condensed ring. Therefore, the above

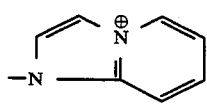

may include

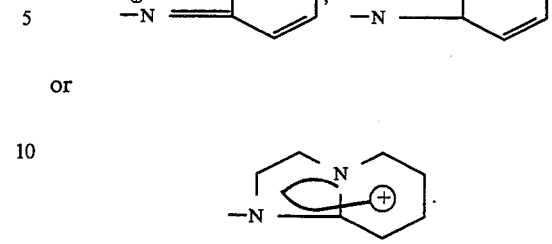

or

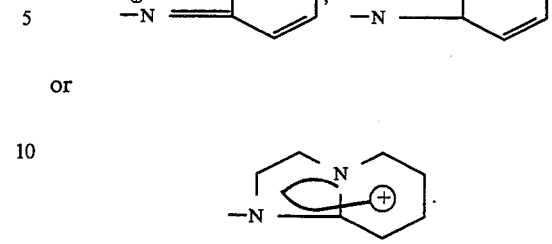

The position in which this positive electric charge takes varies with, among others, the state (solid or in solution) of the compound [I], kinds of solvents, pH, temperature or kinds of substituents. Accordingly, the present invention includes all the cases where the positive electric charge is localized at a nitrogen atom or is delocalized on the entire condensed ring. The number of the substituents $R^{11}$ and $R^{12}$ is preferably one to two.

The substituents $R^{11}$ and $R^{12}$ on the condensed ring A may be exemplified by a hydroxyl group, hydroxy $C_{1-6}$ alkyl group, $C_{1-6}$ alkyl group, $C_{2-6}$ alkenyl group, $C_{2-6}$ alkynyl group, $C_{4-6}$ alkadienyl group, $C_{3-10}$ cycloalkyl group, $C_{5-6}$ cycloalkenyl group, $C_{3-10}$ cycloalkyl $C_{1-6}$ alkyl group, $C_{6-10}$ aryl group, $C_{7-12}$ aralkyl group, di-$C_{6-10}$ arylmethyl group, tri-$C_{6-10}$ arylmethyl group, heterocyclic group, $C_{1-6}$ alkoxy group, $C_{1-6}$ alkoxy $C_{1-6}$ alkyl group, $C_{3-10}$ cycloalkyloxy group, $C_{6-10}$ aryloxy group, $C_{7-19}$ aralkyloxy group, mercapto group, mercapto $C_{1-6}$ alkyl group, sulfo group, sulfo $C_{1-6}$ alkyl group, $C_{1-6}$ alkylthio group, $C_{1-6}$ alkylthio $C_{1-6}$ alkyl group, $C_{3-10}$ cycloalkylthio group, $C_{6-10}$ arylthio group, $C_{7-19}$ aralkylthio group, amino group, amino $C_{1-6}$ alkyl group, mono-$C_{1-6}$ alkylamino group, di-$C_{1-6}$ alkylamino group, mono-$C_{1-6}$ alkylamino $C_{1-6}$ alkyl group, di-$C_{1-6}$ alkylamino $C_{1-6}$ alkyl group, $C_{3-10}$ cycloalkylamio group, $C_{6-10}$ arylamino group, $C_{7-19}$ aralkylamino group, cyclic amino group, cyclic amino $C_{1-6}$ alkyl group, cyclic amino $C_{1-6}$ alkylamino group, azido group, nitro group, halogen atom, halogen $C_{1-6}$ alkyl group, cyano group, cyano $C_{1-6}$ alkyl group, carboxyl group, carboxy $C_{1-6}$ alkyl group $C_{1-10}$ alkoxy-carbonyl group, $C_{1-10}$ alkoxy-carbonyl $C_{1-6}$ alkyl group, $C_{6-10}$ aryloxycarbonyl group, $C_{7-19}$ aralkyloxy-carbonyl group, $C_{6-10}$ aryl-acylt group, $C_{1-6}$ alkanoyl group, $C_{2-6}$ alkanoyl $C_{1-6}$ alkyl group, $C_{3-5}$ alkenoyl group, $C_{6-10}$ arylacyltoxy group, $C_{2-6}$ alkanoyloxy group, $C_{2-6}$ alkanoyloxy $C_{1-6}$ alkyl group, $C_{3-5}$ alkenoyloxy group, carbamoyl $C_{1-6}$ alkyl group, carbamoyl* group, thiocarbamoyl* group, carbamoyl*oxy group, carbamoyloxy $C_{1-6}$ alkyl group, $C_{1-6}$ alkanoylamino group, $C_{6-10}$ arylacyltamino group, sulfonamido group, carboxyamino group, $C_{1-10}$ alkoxy-carboxamido group, $C_{6-10}$ aryloxy-carboxamido group or $C_{7-19}$ aralkyloxy-carboxamido group. Among the above-mentioned substituents, "$C_{4-6}$ alkadienyl group" is exemplified by 1,3-butadienyl, "$C_{3-10}$ cycloalkyl $C_{1-6}$ alkyl group" is exemplified by cyclopentylmethyl or cyclohexylmethyl, and halogen atom means here fluorine, chlorine or bromine. All the groups other than the above may be exemplified as in the foregoing.

These substituents may occur singly or in plurality, being the same or different ones. And, in A¹, the 5,6-position of the imidazole ring may be condensed with an alicyclic ring, aromatic ring or heterocyclic ring. As the examples, the following may be counted:

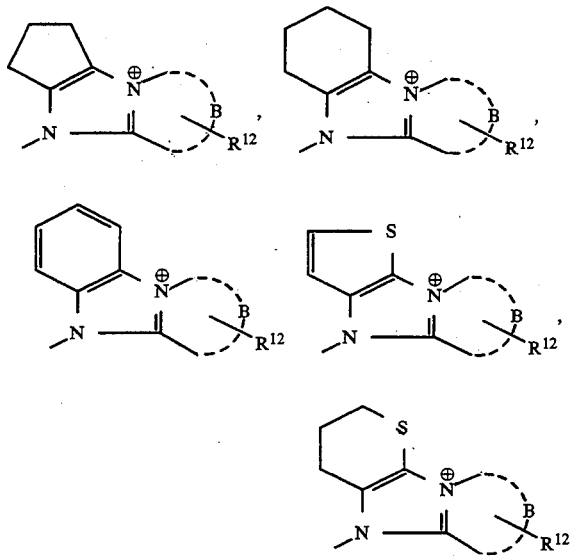

In the above, B and $R^{12}$ are of the same significance as afore-defined. The above-mentioned $R^{11}$ and $R^{12}$ may be further substituted.

In the above compound [I], the mark $\ominus$ attached to the right shoulder of the carboxyl substituent (-COO) means that the said carboxyl group is a carboxylate anion and forms internal salt by making a pair with the positive electric charge on the substituent A. On the other hand, the compound [I] may be its pharmaceutically acceptable salt or ester. As the pharmaceutically acceptable salt, there may be mentioned, among others, inorganic base salts, ammonium salt, organic base salts, inorganic acid addition salts, organic acid addition salts and basic amino acid salts. There may be exemplified an alkali metal (e.g. sodium, potassium, etc.) or an alkaline earth metal (e.g. calcium) as an inorganic base capable of giving the inorganic base salts; procaine, 2-phenylethylbenzylamine, dibenzylethylenediamine, ethanolamine, diethanolamine, tris-hydroxymethylaminomethane, poly-hydroxyalkylamine or N-methylglucosamine as an organic base capable of giving organic base salts; hydrochloric acid, hydrobromic aid, sulfuric acid, nitric acid or phosphoric acid as an inorganic acid capable of giving the inorganic acid addition salts; p-toluenesulfonic acid, methanesulfonic acid, formic acid, trifluoroacetic acid or maleic acid as an organic acid capable of giving organic acid addition salts; and lysine, arginine, ornithine or histamine as a basic amino acid capable of giving basic amino acid salts.

Among these salts, basic salts (i.e. inorganic base salts, ammonium salt, organic base salts and basic amino acid salts) means salts derivable in case there is (are) acidic group(s) e.g. carboxyl group, sulfo group etc. on the substituent $R^1$, $R^3$ or A of the compound [I], and acid addition salts (i.e. inorganic acid addition salts and organic acid addition salts) mean salts derivable in case there is(are) basic group(s) e.g. amino group, monoalkylamino group, dialkylamino group, cycloalkylamino group, arylamino group, aralkylamino group, cyclic amino group, nitrogen-containing heterocyclic group etc. on the substituent $R^1$, $R^3$ or A of the compound [I]. Incidentally, the acid addition salt also includes an intramolecular salt of the compound [I], i.e. a salt having carboxyl (COOH) group at the 4-position and $CH_2A^{\oplus}.M^{\ominus}$ group [wherein $M^{\ominus}$ denotes an anion formed by removal of a proton ($H^{\ominus}$) from inorganic acid or organic acid; such as anion is exemplified by chloride ion, bromide ion, sulfate ion, p-toluenesulfonate ion, methanesulfonate ion, trifluoroacetate ion] at the 3-position, which is formed through addition of one mole of acid to carboxylate ($COO^{\oplus}$) group of the 4-position and $CH_2A^{\ominus}$ group of the 3-position of the compound [I]. The ester derivatives of the compound [I] mean esters derivable by esterifying the carboxyl group contained in the molecule, which include esters usable as synthetic intermediates and bioavailably unstable non-toxic esters. The esters usable as synthetic intermediates are exemplified by $C_{1-6}$ alkyl* ester $C_{2-6}$ alkenyl ester, $C_{3-10}$ cycloalkyl ester, $C_{3-10}$ cycloalkyl $C_{1-6}$ alkyl ester, $C_{6-10}$ aryl* ester, $C_{7-12}$ aralkyl* ester, di-$C_{6-10}$ arylmethyl ester, tri-$C_{6-10}$ aryl-methyl ester or substituted silyl ester. There may be exemplified, as "$C_{1-6}$ alkyl* group" of giving $C_{1-6}$ alkyl* ester, methyl, ethyl, n-propyl, isopropyl, n-butyl, isobutyl, sec-butyl, tert-butyl, n-pentyl, n-hexyl, benzyloxymethyl, 2-methylsulfonylethyl, 2-trimethylsilylethyl, 2,2,2-trichloroethyl, 2-iodoethyl, acetylmethyl, p-nitrobenzoylmethyl, p-mesylbenzoylmethyl, phthalimidomethyl, succinimidomethyl, benzenesulfonylmethyl, phenylthiomethyl, dimethylaminoethyl, pyridine-1-oxide 2-methyl, methylsulfinylmethyl, or 2-cyano-1,1-dimethylethyl; as $C_{2-6}$ alkenyl group capable of giving $C_{2-6}$ alkenyl ester, the afore-mentioned ones, i.e. vinyl, allyl, 1-propenyl, isopropenyl, 1-butenyl, 2-butenyl, 3-butenyl, methallyl, 1,1-dimethylallyl or 3-methyl-3-butenyl; as $C_{3-10}$ cycloalkyl group capable of giving $C_{3-10}$ cycloakyl ester, the afore-mentioned ones, i.e. cyclpropyl, cyclobutyl, cyclopentyl, cyclohexyl, cycloheptyl, norbornyl or adamantyl; as $C_{3-10}$ cycloalkyl $C_{1-6}$ alkyl group capable of giving $C_{3-10}$ cycloalkyl $C_{1-6}$ alkyl ester, the afore-mentioned ones, i.e. cyclopropylmethyl, cyclopentylmethyl or cyclohexylmethyl; as "$C_{6-10}$ aryl* group" capable of giving $C_{6-10}$ aryl* ester, phenyl, α-naphthyl, β-naphthyl, biphenylyl, p-nitrophenyl or p-chlorophenyl; as "$C_{7-12}$ aralkyl* group" capable of giving $C_{7-12}$ aralkyl* ester, benzyl, 1-phenylethyl, 2-phenylethyl, phenylpropyl, naphthylmethyl, p-nitrobenzyl, p-methoxybenzyl, 1-indanyl, phenacyl or 3,5-di-tert-butyl-4-hydroxybenzyl; as di$C_{6-10}$ aryl-methyl group capable of giving di-$C_{6-10}$ aryl-methyl ester, the afore-mentioned ones, i.e. benzhydryl or bis(p-methoxyphenyl) methyl; as tri-$C_{6-10}$ aryl-methyl group capable of giving tri-$C_{6-10}$ aryl-methyl ester, the afore-mentioned ones, i.e. trityl; and as substituted silyl group capable of giving substituted silyl ester, the afore-mentioned ones, i.e. trimethylsilyl, tert-butyldimethylsilyl or -Si(CH$_3$)$_2$CH$_2$CH$_2$Si(CH$_3$)$_2$-. The above esters include esters at the 4-position. Such compound having above ester group at the 4-position forms an intramolecular salt of $CH_2A^{\oplus}.M^{\ominus}$ [wherein $M^{\ominus}$ has the same meaning as defined above] at the 3-position.

As the biovailably unstable and non-toxic esters, those which have been confirmed as employable in the fields of penicillin and cephalosporin can conveniently be employed also in the present invention, which may be exemplified b $C_{2-6}$ alkanoyloxy $C_{1-6}$ alkyl ester, 1-($C_{1-6}$ alkoxy)$C_{1-6}$ alkyl ester, 1-($C_{1-6}$ alkylthio)$C_{1-6}$ alkyl ester or 1-($C_{1-6}$ alkoxycarbonyloxy)$C_{1-6}$ alkyl ester. The $C_{2-6}$ alkanoyloxy $C_{1-6}$ alkyl ester is exemplified by acetoxymethyl ester, 1-acetoxyethyl ester, 1acetoxybutyl ester, 2-acetoxyethyl ester, propionyloxymethyl ester, pivaloyloxymethyl ester. The 1-($C_{1-6}$ alkoxy)$C_{1-6}$ alkyl ester is exemplified by methoxymethyl ester, ethoxymethyl ester, isopropoxymethyl ester, 1-methoxyethyl ester or 1-ethoxyethyl ester. The 1-($C_{1-6}$ alkylthio($C_{1-6}$alkyl ester is exemplified by methylthiomethyl ester or ethylthiomethyl ester. The 1-($C_{1-6}$ alkoxycarbonyloxy)$C_{1-6}$ alkyl ester is exemplified by 1-(ethoxycarbonyloxy)ethyl ester or 1-(tert-butoxycarbonyloxy)ethyl ester. The present invention includes, besides the above-mentioned ester derivatives, pharmaceutically acceptable compounds which are convertible in vivo to the compound [I]. The above-mentioned esters usable as synthetic intermediates and bioavailably unstable non-toxic esters include esters at the 4-position. Such esters at the 4-position usually form an intramolecular salt of $CH_2A^{\oplus}.M^{\ominus}$ [wherein $M^{\ominus}$ has the same meaning as defined above] at the 3-position.

When the compound [I] has a hydroxyl group, the hydroxyl group may be protected. Groups usable for protecting the hydroxyl group include those which are usually employed for protecting the hydroxyl group in the field of β-lactam and organic chemistry, which may be exemplified by, besides the afore-mentioned $C_{2-6}$ alkanoyl groups, a substituted oxycarbonyl group, tert-butyl group, $C_{7-12}$ aralkyl* group, di-$C_{6-10}$ aryl-methyl group, tri-$C_{6-10}$ aryl-methyl group, 1-($C_{1-6}$ alkoxy)$C_{1-6}$ alkyl group, 1-($C_{1-6}$ alkylthio)$C_{1-6}$ alkyl group and substituted silyl group, acetal residues e.g. 2-tetrahydropyranyl or 4-methoxy-4-tetrahydropyranyl.

When the compound [I] additionally has an amino group other than those mentioned above, the amino group may also be protected. Groups employable for protecting those amino groups are exemplified also here by those referred to in the protection of the afore-mentioned amino groups.

The compound [I] of this invention has a broad antibacterial spectrum and can be used for prophylaxis and therapy of various diseases of men and animals caused by pathogenic bacteria, for example, infections of respiratory tract or of urinary passages. Characteristic features of the antibacterial spectrum of the antibacterial compound [I] are mentioned as follows:

(1) remarkably strong activity against a variety of gram-negative bacteria;

(2) strong activity against gram-positive bacteria (e.g. *Staphylococcus aurteus* or *Cornyebacterium diphteriae*);

(3) remarkably effective against *Pseudomonas aeruginosa* which are not sensitive to therapy with conventional cephalosporin-type antibiotics; and (4) Strong activity against a variety of β-lactamase-producing gram-negative bacteria (e.g. the genera Escherichia, Enterobacter, Serratia or Proteus).

Especially against bacteria belonging to the genus Pseudomonas, to which aminoglycoside antibiotics such as Amikacin or Gentamicin have been used, the antibacterial compound [I] shows antibacterial activity comparable to these aminoglycosides with remarkably lower toxicity to men and animals, which is counted as one of the great advantages.

Besides, the antibacterial compound [I] of the present invention has the following characteristic features, i.e. excellent stability, high concentration in blood, long duration of effect and remarkably high concentration in tissue.

Among the compounds [I] of this invention, the compound having a following structure is preferable:

(1) $A^{\oplus}$ is unsubstituted imidazine [1,2-b]pyridazinium-1-yl group;

(2) $A^{\oplus}$ is imidazo[1,5-a]pyridinium-2-yl group which is substituted by a $C_{1-6}$ alkyl group, halogen atom, or cyano group; or (3) $R^1$ is an amino group, $R^3$ is an optionally substituted $C_{1-3}$ alkyl group; and $A^{\oplus}$ is an imidazo[1,2-a]pyridinium-1-yl group which is substituted by a fluorine or cyano group.

How to make the compound [I] of this invention, its salt or ester will be described in detail as follows. The processes described hereafter are all conventional as reactions per se, and analogous ones thereto can also be applied.

The compound [I] of the present invention can be produced by conventional methods, which are mentioned below.

Production method (1)

The compound [I] can be synthesized by reacting the 7-amino compound of the formula:

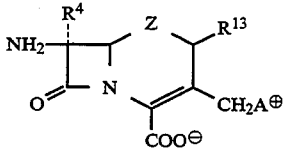

wherein the symbols Z, $R^4$, $R^{13}$ and $A^{\oplus}$ are of the same meaning as defined above or a salt or ester thereof with carboxylic acid of the formula:

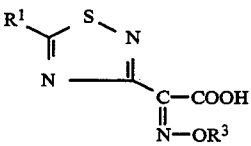

(this compound may be referred to as "$R^bOH$" hereinafter)

wherein the symbols $R^1$ and $R^3$ are of the same meaning as defined above, or a salt or reactive derivative thereof.

This is a method of subjecting a 7-amino compound [II] or a salt or ester thereof (the 7-amino compound [II], and salt and ester thereof may simply be abbreviated hereinafter as the 7-amino compound [II]) to acylation with carboxylic acid $R^bOH$ or a salt or reactive derivative thereof. In this method, the carboxylic acid $R^bOH$ in the free form, a salt or reactive derivative thereof is used as the acylating agent of the 7-amino group of the 7-amino compound [II]. More concretely, the free acid $R^bOH$, or a salt or reactive derivative of the free acid $R^bOH$, such as an inorganic base salt, organic base salt, acid halide, acid azide, acid anhydride, mixed acid anhydride, active amide, active ester or active thioester is used for the acylation. There may be mentioned, among others, as inorganic base salts, alkali metal salts (e.g. sodium salt, potassium salt, etc.) or alkaline earth metal salts (e.g. calcium salts, etc.); as organic base salts, trimethylamine salt, triethylamine salt, tert-butydimethylamine salt, dibenzylmethylamine salt, benzyldimethylamine salt, N,N-dimethylaniline salt, pyridine salt or quinoline salt; as acid halide, acid chloride or acid bromide; as mixed acid anhydride, mono-$C_{1-6}$ alkyl carbonic acid mixed anhydride (e.g. mixed acid anhydride of the free acid $R^bOH$ with, for example, monomethyl carbonic acid, monoethyl carbonic acid, monoisopropyl carbonic acid, monoisobutyl carbonic acid, mono-tert-butyl carbonic acid, monobenzyl carbonic acid, mono(p-nitrobenzyl)carbonic acid, or monoallyl carbonic acid), $C_{1-6}$ aliphatic carboxylic acid mixed anhydride (e.g. mixed acid anhydride of the free acid $R^bOH$ with, for example, acetic acid, trichloroacetic acid, cyanoacetic acid, propionic acid, butyric acid, isobutyric acid, valeric acid, isovaleric acid, pivalic acid, trifluoroacetic acid, trichloroacetic acid or acetoacetic acid), $C_{7-12}$ aromatic carboxylic acid mixed anhydride (e.g. mixed acid anhydride of the free acid $R^bOH$ with, for example, benzoic acid, p-toluic acid or p-chlorobenzoic acid), organic sulfonic acid mixed anhydride (e.g. mixed acid anhydride of the free acid $R^bOH$ with, for example, methanesulfonic acid, ethanesulfonic acid, benzenesulfonic acid or p-toluenesulfonic acid); as active amide, an amide with a nitrogen-containing heterocyclic compound (e.g. acid amide of the free acid $R^bOH$ with, for example, pyrazole, imidazole or benzotriazole, these nitrogen-containing heterocyclic compounds being optionally substituted with aforementioned $C_{1-6}$ alkyl group, $C_{1-6}$ alkoxy group, halogen atom, oxo group, thioxo group or $C_{1-6}$ alkylthio group). As the active ester, those which can be used for the same purpose in the fields of β-lactam and peptide synthesis can all be used, which are exemplified by, —besides organic phosphoric acid ester (e.g. diethoxy phosphoric acid ester or diphenoxy phosphoric acid)—, p-nitrophenyl ester, 2,4-dinitrophenyl ester, cyanomethyl ester, pentachlorophenyl ester, N-hydroxysuccinimide ester, N-hydroxyphthalimide ester, 1-hydroxybenzotriazole ester, 6-chloro-1-hydroxybenzotriazole ester, 1-hydroxy-1-H-2-pyridone ester. The active thioester can be exemplified by esters with aromatic heterocyclic thiol compounds (e.g. 2-pyridylthiol ester, 2-benzothiazolylthiol ester, these heterocyclic rings being substituted with afore-mentioned $C_{1-6}$ alkyl group, $C_{1-6}$ alkoxy group, halogen atom or $C_{1-6}$ alkylthio group). On the other hand, the 7-amino compound [II] can be used as free base, a salt or ester thereof. Salts of the 7-amino compound [II] are exemplified by inorganic base salts, ammonium salt, organic base salts, inorganic acid addition salts or organic acid addition salts. There may be mentioned, as inorganic base salts, alkali metal salts (e.g. sodium salts or potassium salts) and alkaline earth metal salts (e.g. calcium salts); as organic base salts, for example trimethylamine salts, triethylamine salts, tert-butyldimethylamine salts, dibenzylmethylamine salts, benzyldimethylamine salts, N,N-dimethylaniline salts, pyridine salts or quinoline salts; as inorganic acid addition salts, for example hydrochlorides, hydrobromides, sulfates, nitrates or phosphates; and as organic acid addition salts, formates, acetates, trifluoroacetates, methanesulfonates, or p-toluenesulfonates. As the esters of the 7-amino compound [II], esters already referred to as ester derivatives of the compound [I] can also be counted, more concretely, $C_{1-6}$ alkyl* ester, $C_{2-6}$ alkenyl ester, $C_{3-10}$ cycloalkyl ester, $C_{3-6}$ cycloalkyl $C_{1-6}$ alkyl ester, $C_{6-10}$ aryl* ester, $C_{7-12}$ aralkyl* ester, di-$C_{6-10}$ aryl-methyl ester, tri-$C_{6-10}$ aryl-methyl ester or $C_{2-6}$ alkanoyloxy $C_{1-6}$ alkyl ester. The starting material $R^bOH$ as well as salts and reactive derivatives thereof can be easily prepared by known methods or analogous methods thereto. A reactive derivative of the compound $R^bOH$, after isolation from the reaction mixture, can be allowed to react with a 7-amino compound [II], or as the reaction mixture containing the reactive derivative of the compound $R^bOH$ before the isolation, it can be allowed to react with a 7-amino compound [II]. When the carboxylic acid $R^bOH$ is used in the state of its free acid or salt, a suitable condensing agent is employed. As the condensing agents, there may be counted N,N'-di-substituted carbodiimides e.g. N,N'-di-cyclohexylcarbodiimide; azolides e.g. N,N'-carbonyldiimidazole or N,N'-thiocarbonyldiimidazole; dehydrating agents e.g. N-ethoxycarbonyl-2-ethoxy-1,2-dihydroquinoline, phosphorus oxychloride or alkoxyacetylene; 2-halogenopyridinium salts e.g. 2-chloropyridinium methyl iodide or 2-fluoropyridinium methyl iodide. The reactions where these condensing agents are employed are considered to prove via reactive derivatives of the carboxylic acid $R^bOH$. These reactions are generally conducted in a solvent which does not hamper the reaction. These solvents may be exemplified by ethers such as dioxane, tetrahydrofuran, diethyl ether, tert-butyl methyl ether, diisopropyl ether or ethylene glycol dimethyl ether; esters such as ethyl formate, ethyl acetate or n-butyl acetate; halogenated hydrocarbons such as dichloromethane, chloroform, carbon tetrachloride, trichlene or 1,2-dichloroethane; hydrocarbons such as n-hexane, benzene or toluene; amides such as formamide, N,N-dimethylformamide or N,N-dimethylacetamide; ketones such as acetone, methyl ethyl ketone or methyl isobutyl ketone; or nitriles such as acetonitrile or propionitrile, and, besides, dimethyl sulfoxide, sulfolane, hexamethylphosphoramide or water, singly or in combination. The amount of acylating agent ($R^bOH$ or a salt or reactive derivative thereof) is usually about 1 to 5 mol., preferably about 1 to 2 mol., relative to 1 mol. of the 7-amino compound [II]. The reaction is conducted within the temperature range of about −80° to 80° C., preferably about −40° to 50° C., most preferably about −30° to 30° C. The reaction time varies with kinds of the 7-amino compound [II] and carboxylic acid $R^bOH$ or a salt or reactive derivative thereof of the solvent (mixture ratio as well when mixture solvents are used) and reaction temperatures, but it is usually within the range from one minute to 72 hours, preferably from 15 minutes to three hours. When an acid halide is employed as the acylating agent, the reaction can be conducted in the presence of a deacidifying agent for the purpose of eliminating from the reaction system the hydrogen halogenide to be liberated. The deacidifying agent may be exemplified by inorganic bases such as sodium carbonate, potassium carbonate, calcium carbonate or sodium hydrogen carbonate; tertiary amines such as triethylamine, tri(n-propyl)amine, tri(n-butyl)amine, diisopropylethylamine, cyclohexyldimethylamine, pyridine, lutidine, γ-collidine, N,N-dimethylaniline, N-methylpiperidine, N-methylpyrrolidine or N-methylmorpholine; or alkylene oxides such as propylene oxide or epichlorohydrin.

The 7-amino compound [II] can be synthesized by reacting a compound of the formula:

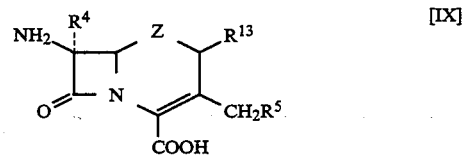

[wherein the symbol $R^5$ stands for hydroxyl group, acyloxy group, carbamoyloxy group, substituted carbamoyloxy or halogen atom, and other symbols are of respectively the same meanings as defined above] or a salt or ester thereof with an imidazole compound of the formula A' [A' means an optionally substituted imidazole forming a condensed ring at 2,3- or 3,4-position] or a salt thereof.

The starting compound [IX] or a salt or ester thereof is a compound which can be easily produced by a conventional method or an analogous one thereto. As salts and esters of the compound [IX] can be also mentioned here the same ones as those of the compound [II].

As the acyloxy group represented by the symbol $R^5$, the above-mentioned acyloxy group can be employed also here, especially preferable being acetoxy, chloroacetoxy, propionyloxy, butyryloxy, pivaloyloxy, 3-oxobutyryloxy, 4-chloro-3-oxobutyryloxy, 3-carboxypropionyloxy, 4-carboxybutyryloxy, 3-ethoxycarbamoylpropionyloxy, benzoyloxy, o-carboxybenzoyloxy, o-(ethoxycarbonylcarbamoyl)benzoyloxy and o-(ethoxycarbonylsulfamoyl)benzoyloxy. As the substituted carbamoyloxy group represented by the symbol $R^5$, the above-mentioned ones can be employed also here, especially preferable being methylcarbamoyloxy and N,N-dimethylcarbamoyloxy. Halogen atoms represented by the symbol $R^5$ are preferably chlorine, bromine and iodine. As to the imidazole compound A' and its salt, detailed description will be given hereafter.

Even in case where the amino group at the 7-position is protected, the above reaction proceeds likewise. When desired, the protecting group may be removed after the reaction to thereby give a 7-amino compound [II].

The carboxylic acid [$R^b$OH] or a salt or reactive derivative thereof can be easily prepared by a known process or a process analogous thereto.

Production method (2)

Furthermore, the compound [I] can be synthesized by reacting a compound of the formula;

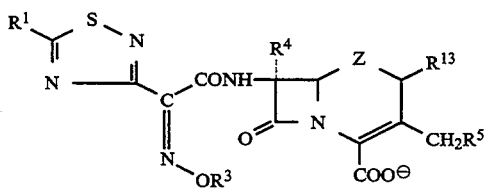 [X]

wherein $R^5$ is hydroxyl group, acyloxy group, carbamoyloxy group, substituted carbamoyloxy group of halogen atom and other symbols are of the same meaning as defined above or a salt or ester thereof with an imidazole compound of the formula A' [A' means an optionally substituted imidazole forming a condensed ring at the 2,3- or 3,4-position] or a salt thereof.

In this reaction, imidazole compound A' or a salt thereof is reacted with a compound [X] or a salt or ester thereof (the compound [X], and salt and ester thereof may simply be abbreviated hereinafter as the compound [X]) to cause nucleophilic substitution, thereby to give the compound [I]. In the compound [X], $R^5$ stands for, also here, hydroxyl group, acyloxy group, carbamoyloxy group, substituted carbamoyloxy group or halogen atom. The compound [X] can be used in the free state, or as salts or esters thereof. The salts and esters of the compounds [X] are those mentioned as salts and esters of the 7-amino compound [II] in the above Production Method (1). The compound [X], or a salt and ester thereof can be easily prepared by known methods or analogous ones thereto. On the other hand, the imidazole compound A' stands for a optionally substituted imidazole forming a condensed ring at the 2,3-position or the 3,4-position. The condensed ring means a form of condensation between the imidazole ring and the 5- to 6-membered aromatic heterocyclic ring. Such condensed ring may be further condensed with another aromatic ring or automatic heterocyclic ring. The optionally substituted imidazole (A') forming a condensed ring at the 2,3-position or the 3,4-position may be represented by the general formula [$A^{1'}$] or [$A^{2'}$];

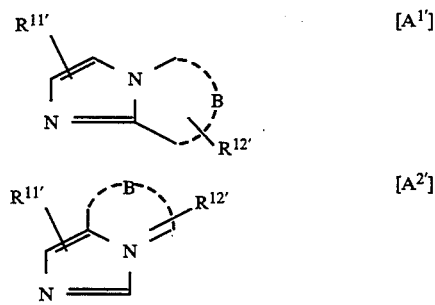

and the A⊕ of the compound [I] to be synthesized by allowing the compound [X] to react with the compound [$A^{1'}$] or a salt thereof stands for the afore-mentioned $A^1$ group, and the A⊕ group of the compound [I] to be synthesized by allowing the compound [X] to react with the compound [$A^{2'}$] or a salt thereof stands for the afore-mentioned $A^2$ group. The symbol B in the formulae of condensed imidazole [$A^{1'}$] and [$A^{2'}$] is of the same meaning as that of symbol B in the [$A^1$] and [$A^2$] groups defined in the above. Hence, the compound [$A^{1'}$] is exemplified by

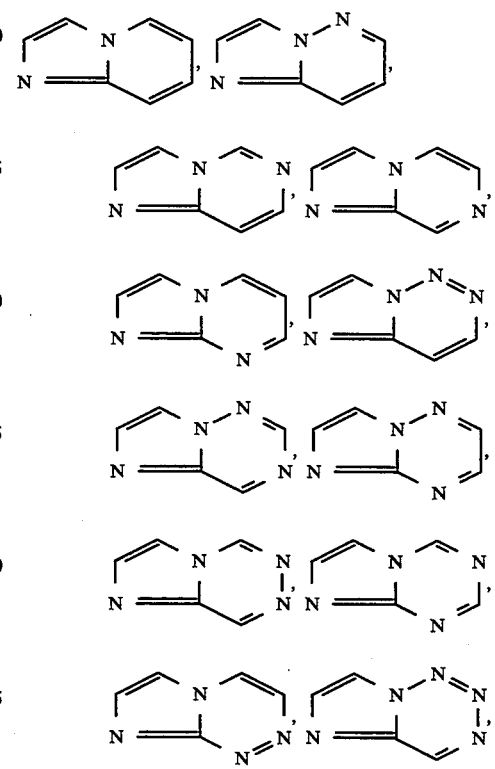

-continued
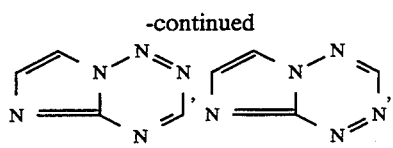
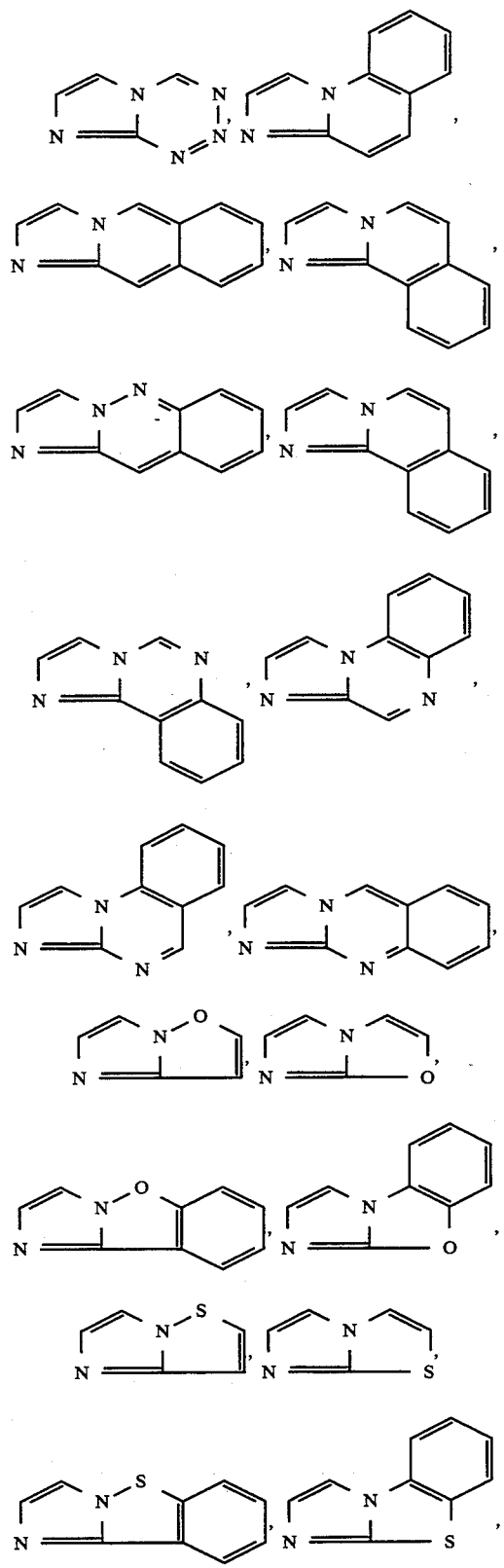
-continued
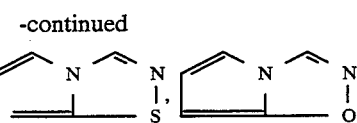
and the compound [A²] is exemplified by
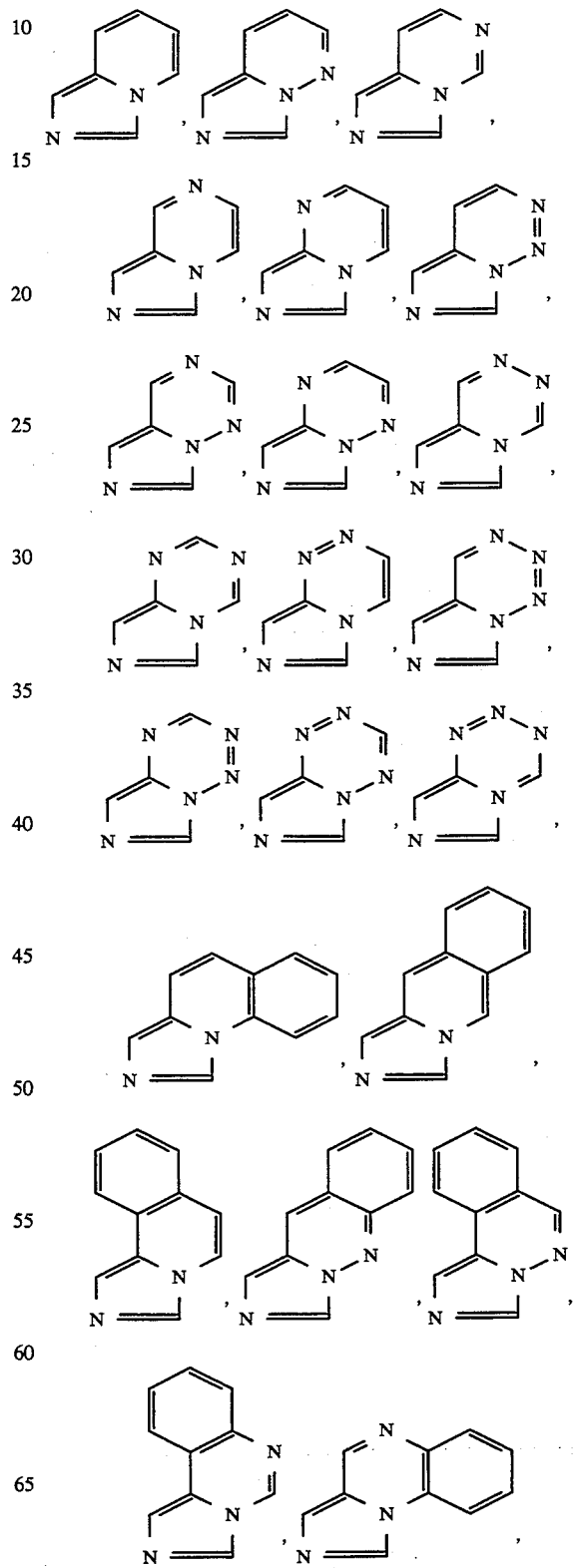

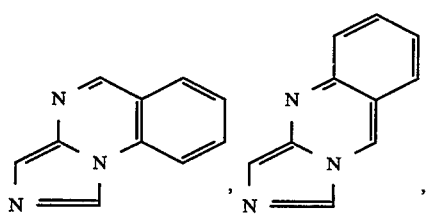

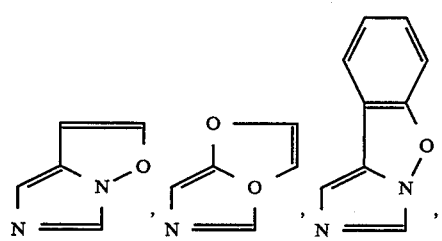

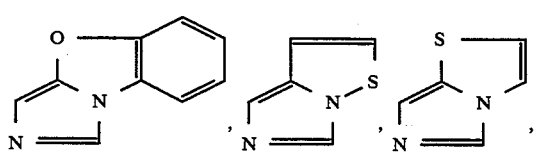

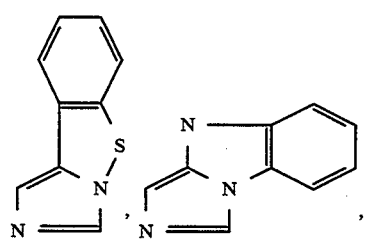

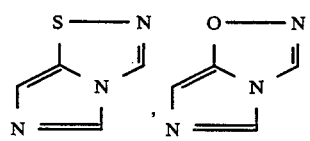

The substituents $R^{11'}$ and $R^{12'}$ on the imidazole compound A' are those mentioned as the substituents $R^{11}$ and $R^{12}$ of the group A. And, in the compound [A1'], the 5,6-position of the imidazole ring may be condensed with an alicyclic ring, aromatic ring or heterocyclic ring, which may be exemplified by

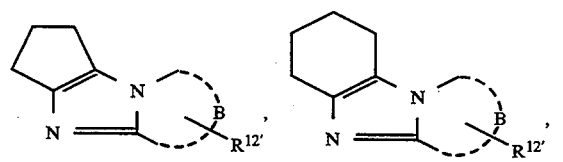

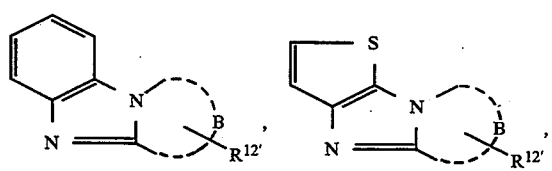

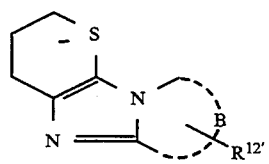

In the above, B and $R^{12'}$ are of the same meaning as defined in the foregoing. The above-mentioned substituents $R^{11'}$ and $R^{12'}$ may be further substituted. The imidazole compound A' may be used as salts thereof, which may be exemplified by inorganic acid addition salts e.g. hydrochloride, hydrobromide, sulfate, nitrate or phosphate, or organic acid addition salts e.g. formate, acetate, trifluoroacetate, methanesulfonate or p-toluenesulfonate. The imidazole compound A' and its salt may be synthesized, in general, by known methods described in literature references or by analogous methods thereto.

The nucleophilic substitution to the compound [X] with the imidazole compound A' or a salt thereof is a per se known reaction, which is usually conducted in a solvent, for example, ethers, esters, halogenated hydrocarbons, hydrocarbons, amides, ketones, nitriles or water, which are used in the Production Method (1). Besides, alcohols such as methanol, ethanol, n-propanol, isopropanol, ethylene glycol or 2-methoxyethanol may be used as well. When the imidazole compound A' or a salt thereof is in liquid state, it may be sometimes used in a large excess amount (e.g. 10 to 200 mol.) relative to the compound [X] to allow it to act also as the solvent. In this case, use of the above-mentioned solvents is unnecessary, or the imidazole A' or a salt thereof may be used as a mixture solvent with any of the above-mentioned solvents.

The case where $R^5$ stands for acyloxy group, carbamoyloxy group or a substituted carbamoyloxy group:

Preferable solvents are water and mixture solvents of water-miscible organic solvents and water. Among the water-miscible organic solvents, preferably ones are exemplified by acetone, methyl ethyl ketone and acetonitrile. The amount of the nucleophilic reagent A' or a salt thereof is usually about 1 to 5 moles, preferably about 1 to 3 moles, relative to 1 mole of the compound [X]. The reaction is conducted within a temperature ranging from about 10° C. to 100° C., preferably from about 30° C. to 80° C. The reaction time depends on the kinds of the compound [X] and the compound A' or a salt thereof, kinds of solvents (mixture ratios when mixture solvents are used), or reaction temperature, and ranges usually from 30 minutes to five days, preferably from one hour to five hours. The reaction is advantageously conducted at pH 2 to 8, preferably near neutral pH, i.e., pH 5 to 8. The reaction readily proceeds usually in the presence of 2 to 30 equivalents of an iodide or thiocyanate. These salts are exemplified by sodium iodide, potassium iodide, sodium thiocyanate and potassium thiocyanate. In addition to the above exemplified salts, a surface-active quaternary ammonium salt such as trimethylbenzylammonium bromide, triethylbenzylammonium bromide or triethylbenzylammonium hydroxide may be sometimes used for allowing the reaction to proceed smoothly.

The case where $R^5$ stands for hydroxyl group:

The reaction may be conducted in the presence of an organic phosphorus compound according to the manner described in, for example, Publication of Unexamined patent application (Kokai) in Japan, No. SHO 58-43979. The organic phosphorus compound is exemplified by o-phenylene phosphorochloridate, o-phenylene phosphorofluoridate, methyl o-phenylene phosphate, ethyl o-phenylene phosphate, propyl o-phenylene phosphate, isopropyl o-phenylene phosphate, butyl o-phenylene phosphate, isobutyl o-phenylene phosphate, sec.-butyl o-phenylene phosphate, cyclohexyl o-phenylene phosphate, phenyl o-phenylene phosphate, p-chlorophenyl o-phenylene phosphate, p-acetylphenyl o-phenylene phosphate, 2-chloroethyl o-phenylene phosphate, 2,2,2-trichloroethyl o-phenylene phosphate, ethoxycarbonylmethyl o-phenylene phosphate, carbamoylmethyl o-phenylene phosphate, 2-cyanoethyl o-phenylene phosphate, 2-methylsulfonylethyl o-phenylene phosphate, benzyl o-phenylene phosphate, 1,1-dimethyl-2-propenyl o-phenylene phosphate, 2-propenyl o-phenylene phosphate, 3-methyl-2-butenyl o-phenylene phosphate, 2-thienylmethyl o-phenylene phosphate, 2-furfurylmethyl o-phenylene phosphate, bis-o-phenylene pyrophosphate, 2-phenyl-1,3,2-benzodioxaphosphole-2-oxide, 2-(p-chlorophenyl)-1,3,2-benzodioxaphosphole-2-oxide, 2-butyl-1,3,2-benzodioxaphosphole-2-oxide, 2-anilino-1,3,2-benzodioxaphosphole-2-oxide, 2-phenylthio-1,3,2-benzodioxaphosphole-2-oxide, 2-methoxy-5-methyl-1,3,2-benzodioxaphosphole-2-oxide, 2-chloro-5-ethoxycarbonyl-1,3,2-benzodioxaphosphole-2-oxide, 2-methoxy-5-ethoxycarbonyl-1,3,2-benzodioxaphosphole-2-oxide, 5-ethoxycarbonyl-2-phenyl-1,3,2-benzodioxaphosphole-2-oxide, 2,5-dichloro-1,3,2-benzodioxaphosphole-2-oxide, 4-chloro-2methoxy-1,3,2-benzodioxaphosphole-2oxide, 2-methoxy-4-methyl-1,3,2-benzodioxaphosphole-2-oxide, 2,3-naphthalene methyl phosphate, 5,6-dimethyl-2-methoxy-1,3,2-benzodioxaphosphole-2-oxide, 2,2-dihydro-4,5,6,7-tetrachloro-2,2,2,-trimethoxy-1,3,2-benzodioxaphosphole, 2,2-dihydro-4,5,6,7-tetrachloro-2,2,2-triphenoxy-1,3,2-benzodioxaphosphole, 2,2-dihydro-2,2-ethylenedioxy-2-methoxy-1,3,2-benzodioxaphosphole, 2,2-dihydro-benzyl-2,2-dimethoxy-1,3,2-benzodioxaphosphole, 2,2-dihydro-4,5-benzo-2,2,2-trimethoxy-1,3,2-benzodioxaphosphole, 2,2-dihydro-2,2,2-triphenoxy-1,3,2,-benzodioxaphosphole, 2,2-dihydro-2,2-(o-phenylenedioxy)-2-phenoxy-1,3,2-benzodioxaphosphole, 2-chrolo-2,2,-dihydro-2,2-(o-phenylenedioxy)-1,3,2,-benzodioxaphosphole 2,2-dihydro-2-methoxy-2,2-(o-phenylenedioxy)-1,3,2-benzodioxaphosphole, 2,2-dihydro-2,2,2-trichloro-1,3,2-benzodioxaphosphole, 9,10-phenanthrenedioxytrimethoxyphosphorus, o-phenylen phosphorochloridite, o-phenylene phosphorobromidite, o-phenylene phosphorofluoridite, methyl o-phenylene phoshite, butyl o-phenylene phosphite methoxycarbonylmethyl o-phenylene phosphite, phenyl o-phenylene phosphite, p-chloro (or p-nitro)phenyl o-phenylene phosphite, 2-phenyl-1,3,2-benzodioxaphosphole, bis-o-phenylene pyrophosphite, 2-methoxy-5-methyl-1,3,2-benzodioxaphosphole, 5-acetyl-2-phenoxy-1,3,2-benzodioxaphosphole, 9,10-phenanthrene phosphorochloridite, 2-chloro-4-methyl-1,3,2-benzodioxaphosphole, 5-ethoxycarbonyl-2-phenyl-1,3,2-benzodioxaphosphole, 2-chloro-2-thioxo-1,3,2-benzodioxaphosphole, 2-phenoxy-2-oxo-1,3,2-benzodiazaphosphole, 2-phenoxy-1,3,2-benzodioxaazaphosphole, 2,2-dihydro-2-oxo-2-methoxy-4,5-dimethyl-1,3,2-dioxaphosphole, 2,2-dihydro-2-oxo-2-chloro-4,5-dimethyl-1,3,2-dioxaphosphole, 2,2-dihydro-2-oxo-2-(1-imidazolyl)-4,5-dimethyl-1,3,2-dioxaphosphole, 2,2-dihydro-2,2-ethylenedioxy-2-methoxy-4,5-dimethyl-1,3,2-dioxaphosphole, 2,2-dihydro-2,2-dimethoxy-2-phenoxy-4,5-dimethyl-1,3,2-dioxaphosphole, 2,2-dihydro-b 2,2,2-trimethoxy-4,5-dimethyl-1,3,2-dioxaphosphole, 2,2-dihydro-2,2,2-triphenoxy-4,5-dimethyl-1,3,2-dioxaphosphole, 2,2-dihydro-2,2,2-tirethoxy-4,5-diphenyl-1,3,2-dioxaphosphole, 2,2-dihydro-2,2,2-trimethoxy-4,5-diphenyl-1,3,2-dioxaphosphole, 2,2-dihydro-2-oxo-2-methoxy-4,5-diphenyl-1,3,2-dioxaphosphole, 2,2-dihydro-2,2,2-trimethoxy-1,3,2-dioxaphosphole, 2,2-dihydro-2,2,2-trimethoxy-4-phenyl-1,3,2-dioxaphosphole, 2,2-dihydro-2,2,2-trimethoxy-4-methyl-1,3,2-dioxaphosphole, 2,2-dihydro-2,2,2-trimethoxy-4-methyl-5-phenylcarbamoyl-1,3,2-dioxaphosphole, 2,2,4,5,6,7-hexahydro-2,2,2-trimethoxy-1,3,2-benzodioxaphosphole, 2,2'-oxybis(4,5-dimethyl-2,2-dihydro-1,3,2-dioxaphosphole) and 2,2'-oxybis(4,5-dimethyl-2,2-dihydro-1,3,2-dioxaphosphole-2-oxide). For the reaction, any solvent can be employed if only it does not hamper the reaction, and, preferably, the aforementioned ethers, esters, halogenated hydrocarbons, hydrocarbons, amides, ketones and nitriles may be used singly or in a mixture thereof. Especially, use of dichloromethane, acetonitrile, formamide, a mixture of formamide and acetonitrile, or a dichloromethane and acetonitrile brings about a preferable result. The amounts of the nucleophilic reagent A' or a salt thereof and the organic phosphorus compound are respectively, relative to 1 mole of the compound [X], about 1 to 5 moles and about 1 to 10 moles, more preferably about 1 to 3 moles and about 1 to 6 moles. The reaction is conducted within the temperature range from about $-80°$ C. to $50°$ C., preferably from about $-40°$ C. to $40°$ C. The reaction time is usually within the range of one minute to 15 hours, preferably five minutes to two hours. To the reaction system may be added an organic base. The organic base may be exemplified by amines such as triethylamine, tri-(n-butyl)amine, di-(n-butyl)amine, diisobutylamine, dicyclohexylamine or 2,6-lutidine. The amount of the base to be added is preferably about 1 to 5 moles relative to 1 mole of the compound [X].

The case where $R^5$ stands for halogen atom:

Preferable solvents are the afore-mentioned ethers, esters, halogenated hydrocarbons, hydrocarbons, amides, ketones, nitriles, alcohols and water. The amount of the nucleophilic reagent A' or a salt thereof to be used is usually, relative to one mole of the compound [X], about 1 to 5 moles, preferably about 1 to 3 moles. The reaction is conducted within a temperature range of about $0°$ to $80°$ C., preferably about $20°$ to $60°$ C. The reaction time is usually 30 minutes to 15 hours, preferably 1 to 5 hours. For accelerating the reaction, the reaction may be conducted in the presence of a dehalogenating agent. As such dehalogenating agents, there may be counted deacidifying agents such as inorganic bases, tertiary amines and alkylene oxides mentioned in the Production Method (1), while the nucleophilic reagent A' or a salt thereof itself may be allowed to act as the dehalogenating agent also. In this case, the compound A' or a salt thereof is used in an amount of two moles or more relative to one mole of the compound [X]. The halogen atom shown by $R^5$ is exemplified by chlorine, bromine, and iodine, and preferably iodine. The compound [X] wherein $R^5$ stands for iodine can be easily produced in accordance with the method described in, for example, Publication of Unexamined patent application (Kokai) in Japan, No. Sho 58-57390 or a method analogous thereto.

The compound [X] can be easily prepared by a known method or a method analogous thereto.

Production method (3)

The compound [I] (wherein $R^3$ stands for an optionally substituted hydrocarbon residue) (this compound is referred to as the compound [I'] or a salt or ester thereof) can also be prepared by, besides the abovementioned Production Method (1) or (2), the Production Method (3) to be described below.

The reaction scheme is as follows:

pound [V]), which is a per se known etherifying reaction.

$R^{3''}$ stands for an optionally substituted hydrocarbon residue which is the same as that referred to in $R^3$. $R^{3''}OH$ may be employed as it is or as a reactive derivative thereof. Reactive derivatives of $R^{3''}OH$ are represented by the formula $R^{3''}Y$, having a group to be liberated together with the hydrogen atom of the hydroxyimino compound [V]. The group Y to be liberated together with a hydrogen atom may be exemplified by halogen atom, sulfo group or mono-substituted sulfonyloxy group. The halogen atom may be exemplified by chlorine, bromine, or iodine. The mono-substituted sulfonyloxy group may be exemplified by $C_{1-6}$ alkylsulfonyloxy and $C_{6-10}$ arylsulfonyloxy groups, e.g. methanesulfonyloxy, ethanesulfonyloxy, benzenesulfonyloxy or p-toluenesulfonyloxy. When a $C_{1-4}$ al-

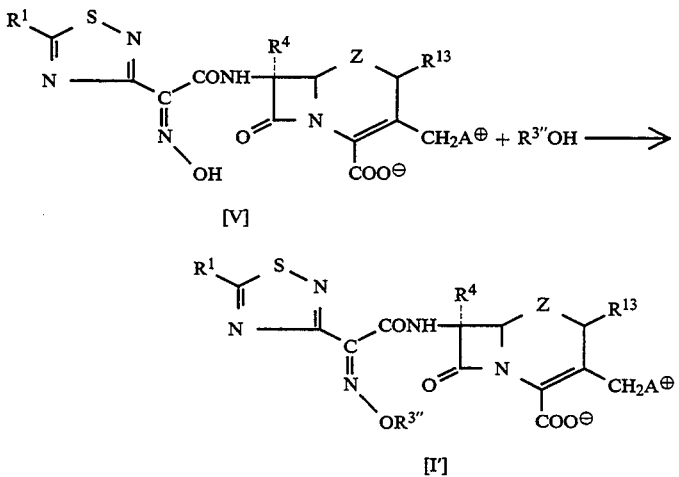

wherein the symbol $R^{3''}$ stands for an optionally substituted hydrocarbon residue, and the symbols Z, $R^1$, $R^4$, $R^{13}$ and $A^\oplus$ are of the same meaning as defined above.

This is a method of synthesizing the compound [I'] or a salt or ester thereof (the compound [I'], and salt and ester thereof may simply be abbreviated hereinafter as the compound [I']) by reacting a compound of the formula: $R^{3''}OH$ or a reactive derivative thereof with a hydroxyimino compound [V] or a salt or ester thereof (the compound [V], and salt and ester thereof may simply be abbreviated hereinafter as the hydroximino comkylether derivatives of the compound [V] is intended, there may be used, besides the abovementioned reaction derivatives, $C_{1-4}$ diazoalkane such as diazomethane or diazoethane, and di-$C_{1-4}$ alkyl sulfate such as dimethyl sulfate or diethyl sulfate.

The compound [V] can be prepared by the acylation as mentioned above in The Production Method (1) or the nucleophilic substitution as mentioned above in the Production Method (2). The reaction schema are as follows, respectively:

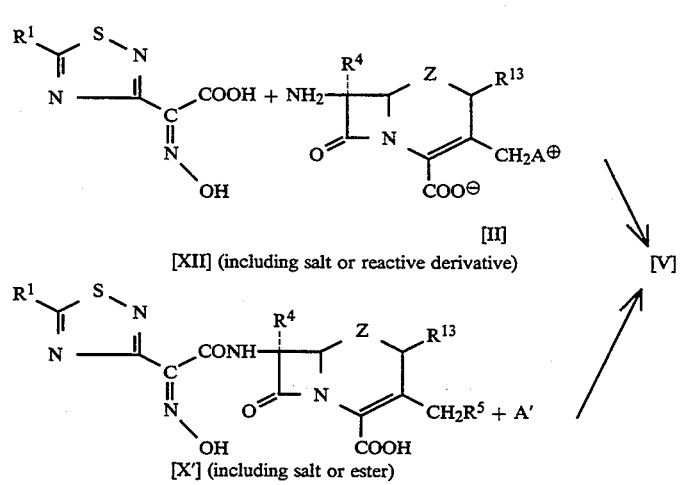

The starting materials [XII] and [X'] can be easily prepared by a known method or an analogous one thereto. The compound R$^{3''}$ and the reactive derivative thereof can also be easily prepared by a known method or an analogous one thereto.

The detailed condition of the reaction of the Method (3) is as follows.

(3-1) The case where R$^{3''}$OH is used:

By using a suitable dehydrating agent the hydroxyimino compound [V] is reacted with the compound R$^{3''}$OH to synthesize the compound [I']. The dehydrating agent may be exemplified by phosphorous oxychloride, thionyl chloride, dialkyl azodicarboxylate (usually used in the presence of phosphine) or N,N-dicyclohexylcarbodiimide, and preferably diethyl azodicarboxylate in the presence of triphenyl phosphine. The reaction in which diethyl azodicarboxylate is used in the presence of triphenyl phosphine is usually conducted in an anhydrous solvent such as ethers or hydrocarbons mentioned above. Relative to 1 mole of the compound [V], about 1 to 1.5 moles each of the compound R$^{3''}$OH, ethyl azodicarboxylate and triphenyl phosphine is employed. The reaction requires 1 to 4 days at a temperature range of about 0° to 50° C.

(3-2) The case where R$^{3''}$Y is used:

The reaction between R$^{3''}$Y and the hydroxyimino compound [V] is a conventional etherification reaction, which is conducted in a solvent. The solvent is exemplified also here by those as mentioned in the Production Method (1) above, i.e., ethers, esters, hydrogenated hydrocarbons, hydrocarbons, amides, ketones, nitriles, alcohols, water or a mixture of any of them, preferably a mixture solvent of a water-miscible solvent and water (e.g. aqueous methanol, aqueous ethanol, aqueous acetone and aqueous dimethyl sulfoxide). The reaction may also be allowed to proceed smoothly in the presence of a suitable base. The base may be exemplified by inorganic bases such as alkali metal salts, e.g. sodium carbonate, sodium hydrogencarbonate or potassium carbonate, or alkali metal hydroxides e.g. sodium hydroxide or potassium hydroxide. This reaction may be conducted in a buffer solution of pH 7.5 to 8.5. The mole numbers of a reagent R$^{3''}$Y and the base relative to 1 mole of the starting compound [V] are respectively about 1 to 5 and about 1 to 10, preferably about 1 to 3 and about 1 to 5, respectively. The reaction temperature is in the range from about −30° C. to 100° C., preferably, about 0° C. to 80° C. The reaction time ranges from 10 minutes to 15 hours, preferably from 30 minutes to 5 hours.

(3-3) The case where C$_{1-4}$ diazoalkane is used:

The reaction is usually conducted in a solvent. As the solvent are employed, for example, the afore-mentioned ethers and hydrocarbons. The hydroxyamino compound [V] is dissolved in a solvent, to which is then added a solution of a diazoalkane compound, whereupon the reaction proceeds. The reagent is used, relative to 1 mole of the compound [V], in an amount of about 1 to 10 moles, preferably about 1 to 5 moles. The reaction is conducted at a relatively low temperature range of from about −50° C. to 20° C., preferably from about −30° C. to 0° C. The reaction time ranges from 1 minute to 5 hours, preferably 10 minutes to one hour.

(3-4) The case where di-C$_{1-4}$ alkylsulfate is used:

The reaction is conducted usually in water or a mixture solvent of a water-miscible solvent and water. As the mixture solvent are mentioned those mentioned in the Production Method (3-2). This reaction is usually conducted in the presence of an inorganic base, for example, an alkali metal hydroxide such as sodium hydroxide and potassium hydroxide. The reagent is used in an amount of about 0.5 to 10 moles, preferably about 1 to 2 moles, relative to 1 mole of the compound [V]. The reaction temperature ranges from about 20° C. to 100° C., preferably about 50° C. to 100° C. The reaction time ranges from 10 minutes to 5 hours, preferably from 30 minutes to 3 hours.

After the above-mentioned Production Method (1)–(3), when required, removal of protecting groups and purification are conducted to obtain the compound [I] of this invention. Methods of removing protecting groups and purification are described as follows:

Process of removing protecting group: As afore-mentioned, in the fields of β-lactam and peptide syntheses, amino-protecting groups have been sufficiently studied, and the method of protecting and deprotecting amino groups has been established. The method of removing the amino-protecting group has also been established, and, in the present invention as well, for removing protecting groups, conventional technique can be used as such. For example, monohalogenoacetyl group (chloroacetyl, bromoacetyl, etc.) can be removed by using thiourea; alkoxycarbonyl group (methoxycarbonyl, ethoxycarbonyl, tert-butoxycarbonyl, etc.) can be removed by using an acid (e.g. hydrochloric acid); aralkyloxycarbonyl group (e.g. benzyloxycarbonyl, p-methylbenzyloxycarbonyl or p-nitrobenzyloxycarbonyl) can be removed by means catalytic reduction; and 2,2,2-trichloroethoxycarbonyl can be removed by using zinc and an acid (e.g. acetic acid). On the other hand, in the case when the compound [I] as the intermediate has been esterified, the ester residue can be removed by a per se known process or an analogous one thereto. For example, 2-methylsulfonylethyl ester can be removed by using an alkali; aralkyl ester (benzyl ester, p-methyoxybenzyl ester, p-nitrobenzyl ester, etc.) can be removed by using an acid (e.g. trifluoroacetic acid) or by means of catalytic reduction; 2,2,2-trichloroethyl ester can be removed by using zinc and an acid (e.g. acetic acid); and silyl ester (e.g. trimethylsilyl ester or tert-butyldimethylsilyl ester) can be removed by using only water.

Process of purifying the compound [I]: The Compound [I] produced in the reaction mixture by any of the processes described in detail in the foregoing Production Methods (1)–(3) and, upon necessity, followed by removal of protecting groups by conducting the above-mentioned process, can be isolated and purified by a known process such as extraction, column-chromatography, precipitation and recrystallization. On the other hand, the compound [I] thus isolated can be converted into then desired physiologically acceptable salts or bioavailably unstable non-toxic esters.

The sulfoxide([I], Z=S→O) of the cephem compound ([I], Z=S) can be prepared by subjecting the compound ([I], Z=S) to a conventional oxidation. Oxidizing agents suitable for oxidation of the sulfur atom of the cephem ring are exemplified by oxygen, peracid, hydroperoxide, or hydrogen peroxide, and the peracid may be made by mixing an acid with a peroxide in the reaction system of the oxidation. As such peracids, use is often made of peracetic acid, perbenzoic acid or p-chloroperbenzoic acid. The reaction is usually conducted in a solvent which is exemplified by ethers such as dioxane or tetrahydrofuran; halogenated hydrocarbons such as dichloromethane, chloroform or chlorobenzene; organic acids such as formic acid, acetic acid, trifluoroacetic acid; or amides such as dimethylformamide or dimethylacetamide. The reaction temperature ranges from about $-20°$ C. to $80°$ C., and preferably a temperature as low as possible, i.e. ranging from about $-20°$ C. to $20°$ C. It is generally known that, when the cephem compound ([I], Z=S) is subjected to oxidation, sulfoxide having an S-configuration is produced. The R- and S-sulfoxide can be separated by utilizing the difference in solubility between them or the difference in travelling rate in chromatography. The above-mentioned oxidation to give sulfoxide can be conducted before or after the afore-mentioned Production Methods (1)–(3).

The compound [I] of this invention can be administered orally or non-orally as injections, capsules, tablets or granules, like known penicillin and cephalosporin preparations. The dosage is 0.5 to 80 mg/day, preferably 1 to 20 mg/day in 3 to 4 doses relative to one kilogram of the body weight of men and animals infected with pathogenic bacteria as set forth above. Carriers of injectable preparations are exemplified by distilled water or physiological saline solution. When used as capsule, powder, granule or tablet, the compound [I] is mixed with conventional pharmaceutically acceptable excipients (e.g. starch, maltose, sucrose, calcium carbonate or calcium phosphate), binders (e.g. starch, gum-arabica, carboxymethylcellulose, hydroxypropylcellulose or crystalline cellulose), lubricants (e.g. magnesium stearate or talc) and disintegrators (e.g. carboxymethyl calcium or talc).

The present invention will be further explained by the following Reference Examples and Examples, but those Examples are mere examples and do not restrict the present invention in any manner.

Elution in column-chromatography in the Reference Examples and Examples was conducted under observation by means of TLC (Thin-Layer Chromatography), wherein were employed 60F$_{254}$ ® manufactured by E. Merck (West Germany) as TLC plate, the solvent for elution in the column-chromatography as developing solvent, and a UV detector as detecting means. As silica-gel for the column, Kieselgel 60 ® (70–230 mesh) manufactured by E. Merck (West Germany) was employed. Cephadex ® is a product of Pharmacia Fine Chemicals(Sweden). XAD-2 ® resin is a product of Rohm & Haas Co. (U.S.A.) NMR spectrum was determined by XL-100A (100 MHz)-, EM390 (90 MHz)-, EM360 (60 MHz)- or T$_{60}$(60 MHz)-type spectrometer using tetramethylsilane as internal or external standard, and all the δ values were shown by ppm. The numeral values parenthesized for mixture solvents mean the ratios by volume of each solvent mixed. "%" for solvents means number of grams in 100 ml of each solution. Symbols in the Reference Examples and Examples have respectively the meanings as follows:

s: singlet
d: doublet
t: triplet
q: quartet
Abq: AB type quartet
d.d: double doublet
m: multiplet
br.: broad
J: coupling constant
Hz: Herz
mg: milligram
g: gram
ml: milliliter
l or l.: liter
%: percent
DMSO: dimethylsulfoxide
D$_2$O: deuterium oxide
CDCl$_3$: deuterochloroform

REFERENCE EXAMPLE 1

7β-[2-(5-tert-Butoxycarbonylamino-1,2,4-thiadiazol-3-yl)-2(Z)-methoxyiminoacetamido]-3-(3-oxobutyryloxymethyl)-3-cephem-4-carboxylic acid To 4 ml of dichloromethane is added 302 mg of 2-(5-tert-butoxycarbonylamino-1,2,4-thiadiazol-3-yl)-2(Z)-methoxyiminoacetic acid, followed by addition of 208 mg of phosphorus pentachloride. The mixture is stirred with ice-cooling for 15 minutes. The solvent is then evaporated off under reduced pressure and hexane is added to the residue. The mixture is evaporated to dryness under reduced pressure and the residue is dissolved in dichloromethane. The resulting solution is added to a solution of 300 mg of 7β-amino-3-(3-oxobutyloxymethyl)-3-cephem-4-carboxylic acid and 0.6 ml of triethylamine in 5 ml of dimethylacetamide, and the mixture is stirred with ice-cooling for 30 minutes. To the reaction mixture is added a solution of 1 g of phosphoric acid in 10 ml of water and the resulting mixture is extracted with methyl ethyl ketone (10 ml). The extract is washed with water and dried over magnesium sulfate. The solvent is then evaporated off under reduced pressure. Ethyl acetate is added to the residue and the solvent is evaporated again to give 390 mg of the above-identified compound.

IR spectrum $\nu_{max}^{KBr}$cm$^{-1}$: 2980, 2940, 1780, 1715, 1540, 1370, 1245, 1150, 1040, 855.

NMR spectrum (d$_6$-DMSO) δ: 1.56(9H, s), 2.20(3H,s), 3.43 and 3.70(2H,ABq, J=18 Hz), 3.65(2H,s), 4.00(3H,s), 4.80 and 5.12 (2H,ABq,J=12 Hz), 5.18(1H,d,J=4.5 Hz), 5.88(1H,d,d,J=9 Hz and 4.5 Hz), 9.63(1H,d,J=9 Hz).

REFERENCE EXAMPLE 2

7β-[2-(5-Amino-1,2,4-thiadiazol-3-yl)-2(Z)-ethoxyiminoacetamido]-3(3-oxobutyryloxymethyl)-3-cephem-4-carboxylic acid In 200 ml of dichloromethane is suspended 11 g of 7β-amino-3-(3-oxobutyryloxymethyl)-3-cephem-4-carboxylic acid. To the suspension is added 14 g of bis-trimethylsilylacetamide and the mixture is stirred at room temperature until complete dissolution and cooled in an ice-water bath. To this solution, 14 g of 2-(5-amino-1,2,4-thiadiazol-3-yl)-2(Z)-ethoxyiminoacetyl chloride is added and the mixture is stirred for a while, to which 6 g of dimethylacetamide is added. The whole mixture is stirred with ice-cooling for 60 minutes. The dichloromethane is evaporated off the residue is dissolved in methyl ethyl ketone. The solution is washed with water and dried. The solvent is then evaporated off and diethyl ether is added to the residue to give a fine precipitate, which is collected by filtration, giving 12.5 of the above-identified compound.

IR spectrum $\nu_{max}^{KBr}$cm$^{-1}$: 3300, 3000, 1780, 1720, 1620, 1520, 1410, 1260, 1150, 1040.

NMR spectrum (d$_6$-DMSO)δ: 1.25(3H,t,J=7 Hz), 2.18(3H,s), 3.41 and 3.63(2H,ABq,J=18 Hz), 3.62(2H,s), 4.18(2H,q,J=7 Hz), 4.76 and 5.06 (2H,ABq,J=13 Hz), 5.14(1H,d,J=4.8 Hz), 5.82(1H,d,d, J=8 Hz and 4.8 Hz), 8.00(2H,br.), 9.48(1H,d,J=8 Hz).

REFERENCE EXAMPLE 3

7β-[2-(5-Amino-1,2,4-thiadiazol-3-yl)-2(Z)-(cyanomethoxyimino)acetamido]-3-(3-oxobutyryloxymethyl)-3-cephem-4-carboxylic acid A mixture of 13 g of 2-(5-amino-1,2,4-thiadiazol-3-yl)acetic acid, 10.7 g of selenium dioxide and 200 ml of dioxane is heated in an oil bath kept at 90° C. for 40 minutes with stirring. After cooling, dioxane is evaporated off. To the residue is added 150 ml of ethyl acetate and, after filtration, ethyl acetate is evaporated off under reduced pressure. To the residue are added 100 ml of ethanol and then, with stirring, 3.6 g of O-cyanomethylhydroxylamine. The mixture is then stirred at room temperature for 40 minutes and ethanol is evaporated off under reduced pressure. The residue is dissolved in 150 ml of ethyl acetate. The ethyl acetate solution is washed once with water and then shaken with 100 ml of 5% aqueous sodium bicarbonate solution. The aqueous phase is separated, covered with 150 ml of ethyl acetate and acidified with phosphoric acid with efficient stirring. The ethyl acetate layer is separated and dried over anhydrous magnesium sulfate. Ethyl acetate is evaporated off under reduced pressure and the residue is dissolved in 30 ml of dichloromethane. To the resulting solution, is added 2.2 g of phosphorous pentachloride under ice-cooling. After 20 minutes' stirring at the same temperature, dichloromethane is evaporated off. The residue is redissolved in 5 ml of dichloromethane and the solution is added all at once to a solution composite of 3.1 g of 7β-amino-3-oxobutyryloxymethyl)-3-cephem-4-carboxylic acid, 6 ml of bistrimethylsilylacetamide and 60 ml of dichloromethane and the mixture is stirred under ice-cooling for 30 minutes. Dichloromethane is then evaporated off and the residue is dissolved in 100 ml of ethyl acetate. The resulting solution is washed with water and dried over anhydrous magnesium sulfate and ethyl acetate is then evaporated off under reduced pressure. To the residue is added 10 ml of ice-cooled trifluoroacetic acid and the mixture is stirred at room temperature for 30 minutes. To the reaction mixture is added 50 ml of ethyl acetate and the solvent is then evaporated under reduced pressure. The residue is triturated with ethyl acetate and the insoluble substance is collected by filtration giving 2 g of crude above-identified compound. The filtrate is then concentrated, the residue treated with diethyl ether and insoluble substance is collected by filtration to give 1.4 g of the above-identified compound.

IR spectrum $\nu_{max}^{KBr}$cm$^{-1}$: 1780, 1700, 1620, 1520, 1400, 1360, 1310, 1140, 1040.

NMR spectrum (d$_6$-DMSO)δ: 2.21(3H,s), 3.44 and 3.68(2H, ABq, J=18Hz), 3.65(2H,s), 4.79 and 5.10(2H, ABq, J=14 Hz), 5.11(2H,s), 5.17(1H, d, J=4.8 Hz), 5.85 (1H, d. d, J=4.8 and 8 Hz), 8.16(2H, br.), 9.74(1H, d, J=8 Hz).

REFERENCE EXAMPLE 4

Imidazo[1,2-a]pyridine derivatives, imidazo[1,5-a]pyridine derivatives and imidazo[1,2-b]pyridazine derivatives are prepared according to the known methods described in e.g. J. Org. Chem. 30, 4081 (1965), J. Org. Chem., 30, 4085 (1965), J. Heterocyclic Chem., 2, 53 (1965), Tetrahedron, 23, 387 (1967), Tetrahedron, 24, 239 (1968), J. Org. Chem., 30, 2403 (1965), J. Med. Chem., 12, 122 (1969) and the similar methods Synthesis of novel imidazo[1,2-a]pyridine derivatives is described below.

(4-1) 6-Cyanoimidazo[1,2-a]pyridine

A mixture of 2.6 g of 6-carbamoylimidazo[1,2-a]pyridine and 25 ml of phosphorus oxychloride is heated under reflux for 16 hours. The excess phosphorus oxychloride is removed under reduced pressure and the residue is poured onto ice. The mixture is neutralized with sodium carbonate and extracted with ethyl acetate. The organic layer is washed with saturated aqueous sodium chloride solution and dried over anhydrous magnesium sulfate. The solvent is then evaporated off under reduced pressure to give 2.0 g of the above-identified compound as colorless crystals.

M.p.: 166°-167° C.

Elemental analysis for C$_8$H$_5$N$_3$: Calcd. (%): C, 67.13; H, 3.52; N, 29.35. Found (%): C, 67.37; H, 3.62; N, 28.99.

(4-2) 8-Hydroxyimidazo[1,2-a]pyridine hydrochloride

In 80 ml of concentrated hydrochloric acid is dissolved 5 g of 8-benzyloxyimidazo[1,2-a]pyridine, and the solution is stirred at room temperature for 24 hours and then concentrated. After addition of 1-butanol, water is azeotropically removed by distillation, and the residue is crystallized from diethyl ether to give 3.8 g of the above-identified compound.

M.p.: 153°-156° C.

IR spectrum $\nu_{max}^{KBr}$ cm$^{-1}$: 1670, 1580, 1520, 1410,1320,1300.

NMR spectrum (d$_6$-DMSO)δ: 7.2-7.4(2H, m), 8.25(1H, d), 8.3-8.5(2H, m).

Novel imidazo[1,2-b]pyridazine derivatives are prepared as follows.

(4-3) 6-Ethoxyimidazo[1,2-b]pyridazine

Sodium metal (0.55 g) is dissolved in 30 ml of ethanol and, to the solution, is added 3 g of 6-chloroimidazo[1,2-b]pyridazine and the mixture is heated under reflux for 3 hours. The solvent is then evaporated off under reduced pressure and the residue is dissolved in water and the mixture is extracted with methylene chloride. The extracts are combined, washed with saturated solution of sodium chloride and dried over MgSO$_4$. The solvent is then evaporated to give 3.3 g of the title compound as colorless crystals.

M.p.: 102°-103° C.

NMR spectrum (CDCl$_3$)δ: 1.45 (3H, T, J=7Hz), 4.53 (2H, q, J=7 Hz), 6.63 (1H, d, J=10 Hz), 7.56 (1H, br.s) 7.68 (1H, br.s), 7.74 (1H, d, J=10 Hz).

(4-4) 6-Methylthioimidazo[1,2-b]pyridazine

To a solution of 3.1 g of 6-chloroimidazo[1,2-b]pyridazine in 5 ml of dimethylformamide, 13 ml of 15% aqueous solution of sodium methylmercaptide are added and the mixture is heated for 3 hours at 100°-105° C. with stirring. After cooling, the reaction mixture is diluted with water and extracted with ether. The extract is washed with water, saturated aqueous solution of sodium chloride and dried over MgSO$_4$. Evaporation of the solvent under reduced pressure gives 2.81 g of the title compound as colorless crystals.

M.p.: 66°-68° C.

NMR spectrum (CDCl$_3$)δ: 2.59 (3H, s), 6.83 (1H, d, J=10 Hz), 7.63 (1H, s), 7.70 (1H, d, J=10 Hz), 1H, br.s).

(4-5) 6-Dimethylamino[1,2-b]pyridazine

6-Chloroimidazo[1,2-b]pyridazine (2.8 g) and 50 ml of dimethylamine solution are placed in a sealed tube and heated for 5 hours at 180° C. After cooling, the solvent is evaporated off and the residue is dissolved in water. The mixture is made alkaline with 10% aqueous sodium hydroxide solution and extracted with ether. The organic phase is separated, washed with water and then with saturated sodium chloride solution and dried over MgSO$_4$. Evaporation of the solvent gives 2.61 g of the title compound as pale yellow crystals.

M.p.: 83°–85° C.

NMR spectrum (CDCl$_3$)$\delta$: 3.10 (6H, s), 6.72 (1H, d, J=10 Hz), 7.53 (1H, br. s), 7.68 (1H, br. s), 7.69 (1H, d, J=10 Hz).

(4-6) 6-(2-Dimethylaminoethoxy)imidazo[1,2-b]pyridazine

Sodium metal (0.25 g) and 6-chloroimidazo[1,2-b]pyridazine are added to 25 ml of 2-dimethylaminoethanol and the mixture is heated in a sealed tube for 3 hours at 130°0 C. After cooling, the solvent is evaporated and the residue is treated with water and extracted with methylene chloride. The organic layer is separated, washed with saturated sodium chloride solution and dried over MgSO$_4$. Evaporation of the solvent gives the title compound as a viscous oil which solidified on standing. The yield is 2.5 g.

NMR spectrum (CDCl$_3$)$\delta$: 2.37 (6H, s), 2.78 (2H, t, J=6 Hz), 4.43 (2H, t, J=6 Hz), 6.75 (1H, d, J=10 Hz), 7.60 (1H, d, J=2 Hz), 7.75 (1H, d, J=2 Hz), 7.80 (1H, d, J=10 Hz).

(4-7) 6-(2-Dimethylaminoethylthio)imidazo[1,2-b]pyridazine

To 20 ml of methanol is dissolved 2.8 g of 2-dimethylaminoethanethiol. To this, 20 ml of 2M solution of sodium methoxide in methanol and 3 g of 6-chloroimidazo-[1,2-b]pyridazine are added successively and the mixture is heated in a sealed tube for 4 hours at 150° C. After cooling, the solvent is evaporated and the residue is treated with water. The mixture is then extracted with methylene chloride. The organic layer is separated, washed with saturated aqueous solution of sodium chloride and dried over MgSO$_4$. Evaporation of the solvent gives 2.5 g of the title compound as pale yellow crystals.

M.p.: 52°–54° C.

NMR spectrum (CDCl$_3$)$\delta$: 2.34 (6H, s), 2.70 (2H, t J=7 Hz), 3.37 (2H, t, J=7 Hz), 6.83 (1H, d, J=10 Hz), 7.68 (1H, br. s), 7.74 (1H, d, J=10 Hz), 7.81 (1H, br. s).

(4-8) 6-Fluoroimidazo[1,2-b]pyridazine (1) A mixture of 3,6-difluoropyridazine (7.8 g) and 25 ml of concentrated ammonium hydroxide solution is heated in a sealed tube for 2 hours at 70° C. After cooling, the crystals separated are filtered and washed with water to give 4 g of 3-amino-6-fluoropyridazine.

NMR spectrum (d$_6$-DMSO)$\delta$: 6.23 (2H, br. s), 7–7.2 (2H, m).

(2) A mixture of 16.6 g of bromoacetaldehyde diethylacetal, 7 ml of concentrated HBr solution and 7 ml of water is heated one hour at 100° C. After cooling, the mixture is diluted with 100 ml of ethanol and neutralized with NaHCO$_3$. Insoluble material is removed by filtration and to the filtrate is added 5 g of 3-amino-6-fluoropyridazine and the mixture is stirred overnight at room temperature. Crystals separated are filtered, washed with ether and dissolved in water. The solution is made alkaline by addition of sodium carbonate and extracted with methylene chloride. The organic layer is washed with water saturated with sodium chloride and dried over MgSO$_4$. Evaporation of the solvent gives 1.7 g of the title compound as pale yellow crystals.

NMR spectrum (CDCl$_3$)$\delta$: 6.90 (1H, d, J=10 Hz), 7.83 (1H, s), 7.88 (1H, s), 7.95 (1H, d, J=10 Hz).

REFERENCE EXAMPLE 5

7$\beta$-(t-Butoxycarbonylamino)-3-(3-oxobutyryloxymethyl)-3-cephem-4-carboxylic acid.

To a mixture of 200 g of 7$\beta$-amino-3-(3-oxobutyloxymethyl)-3-cephem-4-carboxylic acid in 500 ml of dimethylsulfoxide is added 129 g of triethylamine with stirring, followed by stirring at room temperature for 20 minutes. Then to the mixture is added 200 g of di-t-butyl dicarbonate at room temperature, followed by stirring at room temperature for 16 hours.

To the mixture are added 200 g of ice, 2 l. of water, and 1 l. ethyl acetate and the aqueous layer is separated. To the aqueous solution, are added 1 l. of ethyl acetate and 129 g of phosphoric acid.

After vigorous stirring, the ethyl acetate layer is separated and the aqueous layer is extracted with 1 l. of ethyl acetate. The extracts are combined, washed with 2 l. of ice water (twice) and saturated aqueous sodium chloride solution in that order and dried over magnesium sulfate.

The ethyl acetate solution is concentrated under reduced pressure, followed by adding 100 ml of methylene chloride (this procedure is repeated three times).

Resulting residue is dried over phosphorus pentoxide under reduced pressure to give 194 g of the title compound.

Yield: 74%.

Elemental analysis for C$_{17}$H$_{22}$N$_2$O$_8$S.0.5H$_2$O calcd. (%): C, 48.22; H, 5.47; N, 6.62. Found (%): C, 48.16; H, 5.30; N, 6.32.

IR $\nu_{max}^{KBr}$ cm$^{-1}$: 1780, 1720, 1520, 1370, 1320

NMR (DMSO-d$_6$)$\delta$: 1.42(9H, s), 2.18(3H, s), 3.41 & 3.62(2H, AB$_q$, J=18 Hz), 3.62(2H, s), 4.78 & 5.06 (2H, AB$_q$, J=14 Hz), 5.03(1H, d, J=5 Hz), 5.45(1H, dd, J=5 & 8 Hz), 7.83(1H, d, J=8 Hz).

REFERENCE EXAMPLE 6

7$\beta$-Amino-3-[(imidazo[1,2-b]pyridazinium-1-yl)methyl]-3-cephem-4-carboxylate hydrochloride.

(1) 7$\beta$-[D-5-Carboxy-5-phenoxycarbonylaminovaleramido]-3-hydroxy methyl-3-cephem-4-carboxylic acid di-(tri-butylamine) salt (25.9 g) and imidazo[1,2-b]pyridazine (7.15 g) are dissolved in 150 ml of mlethylene chloride. The solution is cooled to −50° C. and to this, 30 ml of 2M solution of ethyl O-phenylenephosphate in methylene chloride is added. The mixture is maintained at −50° to −40° C. for two minutes and then warmed up gradually up to 5° C. over 2 hours. A precipitate separates. Ethyl acetate (450 ml) is added to the reaction mixture and is filtered and washed twice with each 100 ml of methylene chloride and then three times with ethyl acetate to give 17.8 g of 7$\beta$-[D-5-carboxy-5-phenoxycarbonylaminovaleramido]-3-[(imidazo]1,2-b]pyridazinium-1-yl)methyl]-3-cephem-4-carboxylate.

Yield: 100%.

TLC (Silica gel, Merck, Art 5715; Solvent: acetonitrile: water=4:1): Rf=0.19.

IR spectrum $\nu_{max}^{KBr}$ cm$^{-1}$: 1780, 1720, 1625, 1520, 1485, 1380, 1200.

(2) The compound (5.95 g) obtained above is pulverized and added to 150 ml of methylene chloride. To this, under ice-cooling, 5.94 ml of tributylamine and 12.7 ml of dimethylaniline are added. Then, the resulting solution is cooled to −30° C. and to this is added 8.7 ml of proionyl chloride. After being stirred for 15 minutes at −20° C. to −10° C., the mixture is cooled to −60° C. To this, 7.29 g of phosphorus pentachloride is added all at once and the mixture is stirred for 50 minutes at −55° C. to −50° C. Then, 30 ml of isobutanol is added to the reaction mixture maintaining the inner temperature at −55° C. to −45° C. After completion of the addition, the reaction mixture is warmed up from −50° C. to 20° C. over about one hour and then stirred for half an hour at 20° C. and for one hour at 0° C. The precipitate separated is collected by filtration and washed three times with each 10 ml of methylene chloride and dried giving 2.87 g of the title compound.

Yield: 81%.

TLC (Silica gel, Merck, Art 5715; Solvent: acetonitrile: water=4:1): Rf=0.14

IR spectrum $\nu_{max}^{KBr}$ cm$^{-1}$: 1780, 1720, 1625, 1485, 1380, 1200.

REFERENCE EXAMPLE 7

7β-Amino-3-[(imidazo[1,2-b]pyridazinium-1-yl)methyl]-3-cephem-4-carboxylate hydrochloride.

7β-[D-5-Carboxy-5-phenoxycarbonylaminovaleramido]-3-hydroxymethyl-3-cephem-4-carboxylic acid di-(tributylamine) salt (51.8 g) and imidazo[1,2-b]pyridazine (14.3 g) are dissolved in 300 ml of melthylene chloride and the resulting solution is cooled to −50°C. To this, is added 24.0 g of ethyl O-phenylenephosphate and the mixture is stirred for two minutes at −50° to −40° C. Then, the mixture is warmed up from −40° C. to 10° C. over 2 hours. A precipitate separates. To the reaction mixture, 600 mll of methylene chloride and 28.6 ml of tributylamine are added at 0° C. to redissolve the precipitate and then, after addition of 76 ml of dimethylaniline, cooled to −30° C. To this is added 52.1 ml of propionyl chloride and the mixture is stirred for 15 minutes at −20° C. to −10° C. and then cooled to −55° C. To this, 43.7 g of phosphorus pentachloride is added all at once and the mixture is stirred for 50 minutes at −55° C. to −509° C. Then, 180 ml of isobutanol is added, maintaining the inner temperature between −55° to −45° C. After completion of the addition, the mixture is warmeld up from −50° C. to 20° C. over about one hour and then stirred for 30 minutes at 20° C. and for one hour at 0° C. The precipitate separated is collected by filtration and washed three times with each 50 ml of methylene chloride and dried to give 20.0 g of the title compound.

Yield: 94. 2%.

TCL (Silica gel, Merck, Art 5715; Solvent: acetonitrile: water=4:1): Rf=0.14.

REFERENCE EXAMPLE 8

7β-[2-(5-Amino-1,2,4-thiadiazol-3-yl)-2(Z)-methoxyiminoacetamido]-3-(3-oxobutyryloxymethyl)-3-cephem-4-carboxylic acid In 240 ml of dichloromethane is suspended 9.06 g of 7β-amino-3-(3-oxobutyryloxymethyl)-3-cephem-4-carboxylic acid. To the suspension is added 28.9 g of bis-trimethylsilylacetamide and the mixture is stirred at room temperature until complete dissolution and cooled in an ice-water bath. To this solution, 2-(5-amino-1,2,4-thiadiazol-3-yl)-2(Z)-methoxyiminoacetyl chloride hydrochloride prepared from 5.83 g of 2-(5-amino-1,2,4-thiadiazol-3yl)-2(Z)-methoximinoacetic acid and 6.02 g of phosphorus pentachloride in 90 ml of dischloromelthane is added and the mixture is stirred for a while. The whole mixture is stirred with ice-cooling for 60 minutes. The dichloromethane is evaporated off and the residue is dissolved in melthyl ethyl ketone. The solution is washed with water and dried. The solvent is then evaporated off and diethyl ether is added to the residue to give a fine precipiate, which is collected by filtration, giving 11.8 (82% yield) g of the title compound.

IR spectrum $\nu_{max}^{KBr}$ cm$^{-1}$: 3300, 3000, 1770, 1710, 1620, 1520, 1400, 1260, 1150, 1040.

NMR spectrum (d$_6$-DMSO) δ: 2.19(3H,s), 3.40 and 3.65 (2H,ABq,J=18 HZ), 3.63(2H,s), 3.95(3H,s), 4.78 and 5.09(2H,ABq,J=14 Hz), 5.14(1H,d,J=4.8 Hz), 5.84(1H,d,d,J=8 Hz and 4.89 Hz), 8.11(2H,br.), 9.59(1H,d,J=8 Hz).

EXAMPLE 1

7β-2-(5-Amino-1,2,4-thiadiazol-3-yl)-2(Z)-ethoxyiminoacetamido]-3-[(6-cyanoimidazo[1,2-a]pyridinium-1-yl)methyl]-3-cephem-4-carboxylate

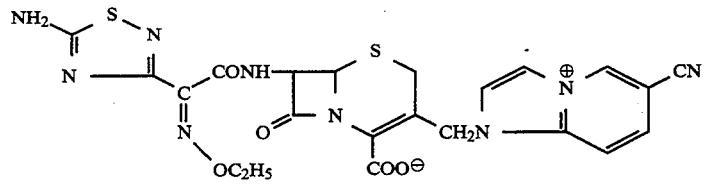

In 30 ml of a 1.1 mixture of acetonitrile and water are dissolved 2.3 g of 7β-[2- (5-amino-1,2,4-thiadiazol-3-yl)-2(Z)-ethoxyiminoacetamido]-3-(3-oxobutyryloxymethyl)-3-cephem-4-carboxylic acid, 179 g of 6-cyanoimidazo[1,2-a]pyridine and 2.2 g of potassium iodide, and the mixture is stirred at 60°–70° C. for 1.5 hours. The solvent is then evaporated off under reduced pressure and the residue is solidified by addition of 100 ml of acetonitrile. The resulting powder is collected by filtration and then subjected to silica gel column chromatography. The acetonitrilel-water (7:3)-eluted fraction is concentrated under reduced pressure and the residue is lyophilized. A solid obtained is dissolved in 5 ml of water and chromatographed on a column of MCI GEL CHP20P ® (150–300 meshes; Mitsubishi Chemical Industries, Ltd., Japan) with water-ethanol.

The water-ethanol (85:15)-eluted fraction is concentrated under reduced pressure and the residue lyophilized to give 0.27 g of the above-identified compound.

Elemental analysis for C$_{22}$H$_{19}$N$_9$O$_5$S$_2$.4H$_2$O: Calcd. (%): C, 42.24; H, 4.35; N, 20.15. Found (%): C, 42.12; H, 3.99; N, 19.97.

IR spectrum $\nu_{max}^{KBr}$ cm$^{-1}$;2250, 1760, 1620, 1525.

NMR spectrum (d$_6$-DMSO)δ: 1.19(3H,t,J=7 Hz), 2.98 and 3.44(2H,ABq,J=18 Hz), 4.12(2H, q,J=7 Hz), 5.00(1H,d,J=5 Hz), 5.1–5.6(2H,m), 5.66(1H,d,d,J=5 Hz & 8Hz), 8.10(2H,br,s), 8.2–9.0(4H.m), 9.42(1H,d,J=8 Hz), 9.76(1H,br,s).

EXAMPLE 2

7β-[2-(5-Amino-1,2,4-thiadiazol-3-yl)-2(Z)-methoxyiminoacetamido]-3-[(imidazo[1,2-a]pyridinium-1-yl)methyl]-3-cephem-4-carboxylate

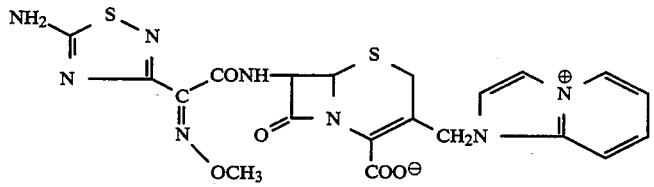

(i) Three grams of 7β-[2-(5-tert-butoxycarbonylamino-1,2,4-thiadiazoll-3-yl)-2(Z)-methoxyiminoacetamido]-3-(3-oxobutyryloxymethyl)-3-cephem-4-carboxylic acid, 3 g of postassium iodide and 3 g of imidazo[1,2-a]pyridine, are reacted as in Example 1.

The reaction mixture is then washed with ethyl acetate, and the aqueous layer is separated and subjected to XAD-2 ® column chromatography using water as eluent. The reaction product eluted is subjected to silica gel column chromatography [silica gel: 40 g; eluent: acetone-water (6:4)] to give 290 mg of the above-identified compound.

Elemental analysis for $C_{20}H_{18}N_8O_5S_2.4H_2O$: calcd. (%): C, 4.95; H, 4.47; N, 19.10. Found (%): C, 41.15; H, 4.23; N, 18.54.

IR spectrum $\nu_{max}$KBr cm$^{-1}$: 1770, 1620, 1530, 1390, 1045, 770.

NMR spectrum (D$_6$-DMSO)δ: 2.96 & 3.42(2H,ABq,J=18 Hz), 3.86(3H,s), 4.98(1H,d,J=4.8 Hz), 5.26 & 5.48(2H,ABq,J=14 Hz), 5.62(1H,d,d,J=8 Hz & 4.8 Hz), 7.40-7.60(1H,t), 7.896-8.20(3H,m). 8.34-8.76(3H,m), 8.86-9.00(1H,d), 9.43(1H,d,JK=8 Hz).

Further, another reaction product eluted from the XAD-2 ® column chromatography using 50% ethanol as eluent is again subjected to silica gel column chromatography [silica gel: 40 g; eluent: acetone-water (67:4)] to give 240 mg of 7β-[2-(5-tert-butoxycarbonylamino-1,2,4-thiadiazol-3-yl)-2(Z)-methoxyiminoacetamido]-3-[(imidazo[1,2-a]-pyridinium-1-yl)methyl]-3-cephem-4-carboxylate.

IR spectrum $\nu_{max}^{KBr}$ cm$^{-1}$: 1775, 1620, 1530, 1380, 1160, 1045, 770

NMR spectrum (D$_2$O)δ: 1.50(9H,s), 3.15 & 3.55 (2H,ABq,J=18 Hz), 4.08(3H.s), 523(1H,d,J=4.8 Hz), 5.32(2H, s), 5.86(1H,d,J=4.8 Hz), 7.09-8.20(7H,m), 866(1H,d,J=8 Hz).

(ii) 7β-[2-(5-tert-Butoxycarbonylamino-1,2,4-thiadiazol-3-yl)-2(Z)-methoxyiminoacetamido]-3-[(imidazo[1,2-a]pyridinium-1yl)methyl]-3-cephem-4-carboxylate (240 mg) obtained in the above procedure (i) is treated with 2 ml of trifluoroacetic acid under ice-cooling. Then, the cooling bath is removed and the reaction mixture is stirred at room temperature for 40 minutes, followed by the addition of ethyl acetate. The mixture is evaporated to dryness under reduced pressure. The residue is dissolved in water, and the solution is neutralized with sodium hydrogen carbonate under ice-cooling and then subjected to XAD-2 column chromatography using 20% $C_2H_5OH$ as the eluent. The eluted fraction is further subjected to silica gel column chromatography [silica gel: 40 g; eluent: acetone-water (6:4)]. Fractions containing the desired product is concentrated and lyophilized to give 310 mg of the above-identified compound.

EXAMPLE 3

7β-[2-(5-Amino-1,2,4-thiadiazol-3yl)-2(Z)-ehoxyiminoacetamido]-3-[(imidazo[1,2-a]pyridinium-1yl)-methyl]-3-cephem-4-carboxylate

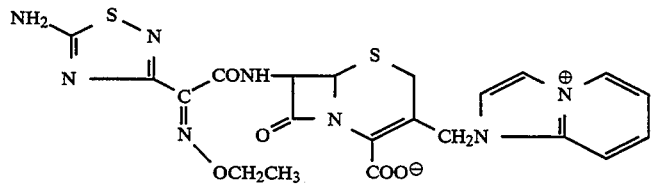

7β-[2-(5-Amino-1,2,4-thiadiazol-3-yl)-2(Z)-ethoxyiminoacetamido]-3-(3-oxobutyryloxymethyl)-3-cephem-4-carboxylic acid and imidazo[1,2-a]pyridine, are reacted in a manner as in Example 1 to give the above-identified compound.

Elemental analysis for $C_{21}H_{20}N_8O_5S_2.4\ H_2O$: Calcd. (%): C, 42.00; H, 470; N, 18.66. Found (%): C, 42.25; H, 4.25; N, 1844.

IR spectrum $\nu_{max}^{KBr}$ cm$^{-1}$: 1770, 1610, 1530, 1390, 1360, 1040, 765.

NMR spectrum (d$_6$-DMSO) δ: 1.20(3H, t. J=7 Hz), 3.02 and 3.44(2H,ABq,J=18 Hz), 4.12(2H.q, J=7 Hz), 5.01(1H,d,J=4.8 Hz), 5.43(2H,br.s), 5.66(1H,d.d,J=8 Hz & 4.8Hz), 7.50(t,J=7 Hz), 8.00(t.J=7 Hz), 8.40-7.00(m) and 8.99(d,J=7 Hz) (total 6H), 9.42(1H,d,J=8 Hz), 8.16(2H,s).

EXAMPLE 4

7β-[2-(5-Amino-1,2,4-thiadiazol-3-yl)-2(Z)-ethoxyiminoacetamido]-3-[(6-chloroimidazo[1,2-a]pyridinium-1-yl)methyl]-3-cephem-4-carboxylate

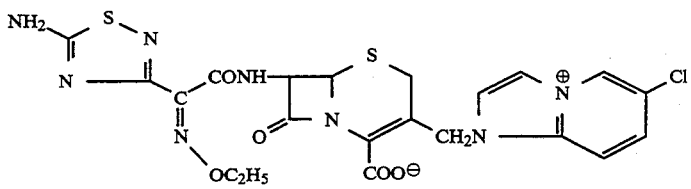

7β-[2-(5-Amino-1,2,4-thiadiazol-3-yl)-2(Z)-ethoxyiminoacetamido]-3-(3-oxobutyryloxymethyl)-3-cephem-4-carboxylic acid and 6-chloroimidazo[1,2-a]-pyridine are reacted in a manner as in Example 1 to give the above-identified compound.

Elemental analysis for $C_{21}H_{19}ClN_8O_5S_2 \cdot 3H_2O$: calcd. (%): C, 40.88; H, 4.08; N,18.16. Found (%): C, 40.85; H, 3.97; N, 18.01.

IR spectrum $\nu_{max}^{KBr}$ cm$^{-1}$: 3300, 3150, 1780, 1630, 1620, 1520, 1390, 1040

NMR spectrum (d$_6$-DMSO) δ: 1.11(3E.t,J=7 Hz), 2.99 and 3.44(2H,ABq,J=18 Hz), 4.13(2H,q,J=7 Hz), 5.00(1H,d,J=4,8 Hz), 5.27& 5.49(2H,ABq,J=14 Hz), 5.66(1H,d.d,J=8 Hz & 4.8 Hz), 8.00–8.86(m) and 9.30(s)(total 5E), 9.42(1H,d,J=8 Hz).

EXAMPLE 5

7β-[2-(5-Amino-1,2,4-thiadiazol-3-yl)-2(Z)-ethoxyiminoacetamido]-3-[3-(dimethylaminomethyl)imidazo[1,2-a]-pyridinium-1-yl)methyl]-3-cephem-4-carboxylate

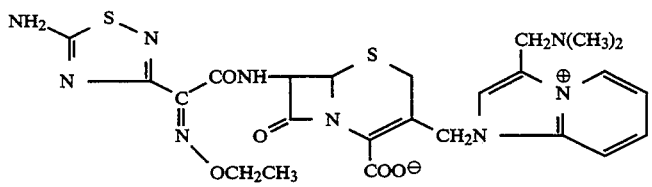

7β-[2-(5-Amino-1,2,4-thiadiazol-3-yl)2(Z)-ethoxyiminoacetamido]-3-(3-oxobutyryloxymethyl)-3-cephem-4-carboxylic acid and 3-(dimethylaminomethyl)imidazo]1,3-a]pyridine are reacted in a manner as in Example 1 to give the above-identified compound.

Elemental analysis for $C_{21}H_{27}N_9O_5S_2 \cdot 3H_2O$: calcd. (%): C, 45.06; H, 520; N, 19.71. Found (%): C, 45.18; H, 4.68; N, 19.57.

IR spectrum $\nu_{max}^{KBr}$ cm$^{-1}$: 1770, 1660, 1615, 1530.

NMR spectrum (d$_6$-DMSO) δ: 1.26(3H,t,J=7 Hz), 2.90(3H, s), 2.98(3H,s), 4,17(2E,q,J=7 Hz), 5.06(2H,br,s), 5.19(1E,d, J=4.5 Hz), 5.68(1H,d.d,J=4.5 Hz & 8 Hz), 6.96–7.56(2H.m), 7.54–7.76(1H,m), 7.84–8.00(1H,m), 8.10(2H,br.s), 8.76–9.00 (1H,m), 9.48(1H,d,j=8 Hz).

EXAMPLE 6

7β-[2-(5-Amino-1,2,4-thiadiazol-3-yl)-2(Z)-methoxyiminoacetamido]-3-[(imidazo[1,2-b]pyridazinium-1-yl)methyl]-3-cephem-4-carboxylate hydrochloride.

To a solution of 7β-[2-(5-amino-1,2,4-thiadiazol-3-yl)-2(Z)-methoxyiminoacetamido]-3-](imidazo]1,2-b]pyridazinium-1-yl-methyl]-3-cephem-4-carboxylate (130 mg) in 0.4 ml of water, 200 μl of 1N hydrochloric acid is added. To this, 20 ml of acetone is added and the mixture is stirred for 5 minutes. The precipitate separated is collected by filtration, washed with small amount of acetone and dried to give the title compound.

IR spectrum $\nu_{max}^{KBr}$ cm$^{-1}$: 1780, 1675, 1620, 1520, 1450, 1380, 1220.

EXAMPLE 7

7β-[2-(5-Amino-1,2,4-thiadiazol-3-yl)-2(Z)-cyanomethyloxyiminoacetamido]-3-[(imidazo[1,2-a]pyridinium-1-yl)methyl]-3-cephem-4-carboxylate

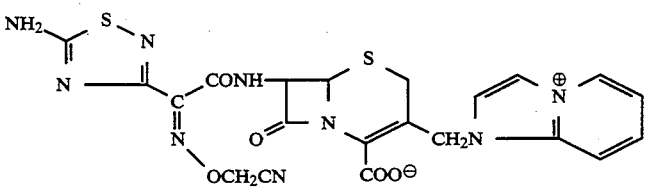

Two grams of the 7β-[2-(5-amino-1,2,4-thiadiazol-3-yl)-2(Z)-cyanomethoxyiminoacetamido]-3-(3-oxobutyryloxymethyl)-3-cephem-4-carboxylic acid obtained in Reference Example 3, 2 g of imidazo[1,2-a]pyridine and 2 g of sodium iodide are mixed in a mixture of 20 ml each of acetonitrile and water and the mixture is heated in an oil bath kept at 75° C. for 60 minutes with stirring and then allowed to cool. To the reaction mixture, 50 ml of ethyl acetate is added and, after shaking, the aqueous layer is separated and concentrated. The residue is then placed on a XAD-2 column and eluted first with water, then with 20% ethanol in water. Fractions containing the objective compound are concentrated and filtered to remove some insoluble materials. The filtrate is lyophilized and the product obtained is dissolved in small amount of water and subjected to chromatography on a column of silica gel. The column is washed with acetone and then the desired product is eluted with acetone:water=7:3. Fractions containing the objective compound are concentrated and the residue is lyophilized to give the above-identified compound.

IR spectrum $\nu_{max}^{KBr}$ cm$^{-1}$: 3100, 1760, 1605, 1520, 1380, 1040, 1010, 760.

NMR spectrum (D$_2$O) δ: 3.16 and 3.53(2H, ABq, J=18 Hz), 5.15 (1H, d, J=4.8 Hz), 5.31(2H, br.s), 5.82(1H, d, J=4.8 Hz), 7.40–7.80, 7.90–8.30 and 8.60–8.80(6H, m).

EXAMPLE 8

7β-[2-(5-Amino-1,2,4-thiadiazol-3-yl)-2(Z)-ethoxyiminoacetamido]-3-[(3-cyancimidazo[1,2-a]pyridinium-1-yl)methyl]-3-cephem-4-carboxylate

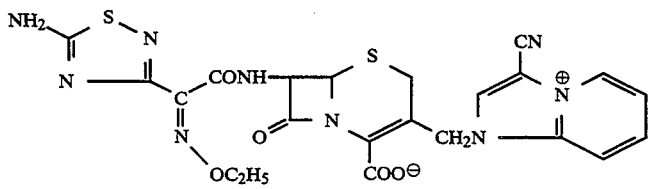

7β-[2-(5-Amino-1,2,4-thiadiazol-3-yl)-2(Z)-ethoxyiminoacetamido]-3-(3-oxobutyryloxymethyl)-3-cephem-4-carboxylic acid and 3-cyanoimidazo[1,2-a]pyridine are reacted in a manner as in Example 1 to give the above-identified compound.

Elemental analysis for C$_{22}$H$_{19}$N$_9$O$_5$S$_2$.3H$_2$O: Calcd.(%): C, 43.49; H, 4.15; N, 20.45. Found (%): C, 43.58; H, 3.59; N, 20.38.

IR spectrum $\nu_{max}^{KBr}$ cm$^{-1}$: 2245, 1770, 1680, 1640, 1610, 1510.

NMR spectrum (d$_6$-DMSO) δ: 1.20(3H, t, J=7 Hz), 3.01(1H, ABqx½, J=18 Hz), 4.12(2H, d, J=7 Hz), 4.98(1H, d, J=4.5 Hz), 5.33 and 5.58(2H, ABq, J=14 Hz), 5.65(1H, d.d, J=4.5 Hz and 8 Hz), 7.64–7.88(1H, m), 8.04(2H, br.s), 8.00–8.48(1H, m), 8.92–9.12(2H, m), 9.42(1H, d, J=8 Hz), 9.47(1H, s).

EXAMPLE 9

7β-[2-(5-Amino-1,2,4-thiadiazol-3yl)-2(Z)-cyanomethoxyiminoacetamido]-3-[(6-cyanoimidazo[1,2-a]pyridinium-1-yl)methyl]-3-cephem-4-carboxylate The compound obtained in Reference Example 3 and 6-cyanoimidazo[1,2-a]pyridine are reacted in a manner as in Example 1 to give the above-identified compound.

Elemental analysis for C$_{23}$H$_{17}$N$_9$O$_5$S$_2$.4.5H$_2$O: Calcd.(%): C, 42.85; H, 4.07; N, 19.56. Found (%): C, 42,68; H, 4.01; N, 19.51.

IR spectrum $\nu_{max}^{KBr}$ cm$^{-1}$: 3400, 2250, 1760, 1670, 1650, 1610, 1530.

NMR spectrum (d$_6$-DMSO) δ: 2.96 and 3.46(2H, ABq, J=16 Hz), 5.01(1H, d, J=5 Hz), 5.02(2H, s), 5.27 and 5.53(2H, ABq, J=15 Hz), 5.64(1H, d.d, J=5 Hz and 8 Hz), 8.2–9.0 (4H, m), 8.22(2H, br.s), 9.66(1H, d, J=8 Hz), 9.77(1H, br.s).

EXAMPLE 10

7β-[2-(5-Amino-1,2,4-thiadiazol-3-yl)-2(Z)-methoxyiminoacetamido]-3-[(6-cyanoimidazo[1,2-a]pyridinium-1-yl)methyl]-3-cephem-4-carboxylate

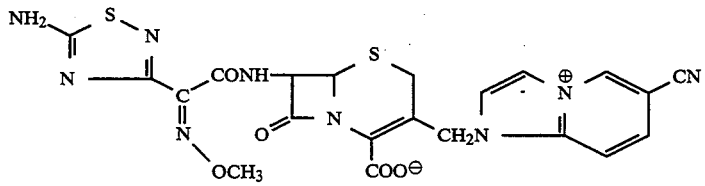

The compound obtained in Reference Example 1 and 6-cyanoimidazo[1,2-a]pyridine are reacted in a manner as in Example 2 to give the above-identified compound.

Elemental anaylsis for C$_{21}$H$_{17}$N$_9$O$_5$S$_2$.3H$_2$O: Calcd.(%): C, 42,49; H, 3.91; N, 21,24. Found (%): C, 42.56; H, 3.67; N, 21.01.

IR spectrum $\nu_{max}^{KBr}$ cm$^{-1}$: 3450, 2250, 1760, 1600, 1520.

NMR (d$_6$-DMSO) δ: 2.98 and 3.46(2H, ABq, J=16 Hz), 3.86(3H, s), 5.00(1H, d, J=5 Hz), 5.28 and 5.54(2H, ABq, J=15 Hz), 5.64(1H, d.d, J=5 Hz and 8 Hz), 8.11(2H, br.s), 8.2–9.0 (5H, m), 9.44(1H, d, J=8 Hz), 9.78(1H, br.s).

EXAMPLE 11

7β-[2-(5-Amino-1,2,4-thiadiazol-3-yl)-2(Z)-carboxymethoxyiminoacetamido]-3-[(6-cyanoimidazo[1,2-a]pyridinium-1-yl)methyl]-3-cephem-4-carboxylate monosodium salt

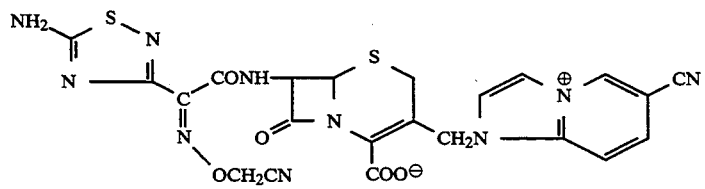

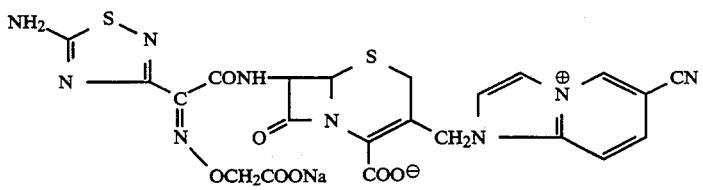

One gram of 7β-[2-(5-amino-1,2,4-thiadiazol-3-yl)-2(Z)-carboxymethoxyiminoacetamido]-3-(3-oxobutyryloxymethyl-3-cephem-4-carboxylic acid obtained as in Example 12 (iii), 1 g of 6-cyanoimidazo[1,2-a]-pyridine and 1 g of sodium iodide are added in a mixture of 15 ml of acetonitrile and 15 ml of water and the mixture is heated in an oil bath kept at 70°–75° C. for 1.5 hours with stirring. The reaction mixture is shaken with ethyl acetate and the aqueous layer is separated, concentrated under reduced pressure and chromatographed on a silica gel column with acetone and then acetone:water=7:3. Fractions containing the objective compound are concentrated and the residue is lyophilized to give the above-identified compound.

Elemental analysis for $C_{22}H_{16}N_9O_7S_2NA.5H_2O$
Calcd.(%): C, 37.99; H, 3.77; N, 18.12. Found (%): C, 38.18; H, 3.33; N, 17.15.

IR spectrum $\nu_{max}^{KBr}$ cm$^{-1}$: 2240, 1760, 1600, 1520, 1400, 1360, 1045.

NMR spectrum (D$_2$O) δ: 3.16 and 3.59(2H, ABq, J=18 Hz), 5.24 (1H, d, J=4.8 Hz), 5.38(2H, br.s), 5.86(1H, d, J=4.8 Hz), 8.2–9.0(4H, m), 9.8(1H, br.s).

EXAMPLE 12
7β-[2-(5-Amino-1,2,4-thiadiazol-3-yl)-2(Z)-carboxymethoxyiminoacetamido]-3-[(imidazo[1,2-]pyridinium-1yl)methyl]-3-cephem-4-carboxylate

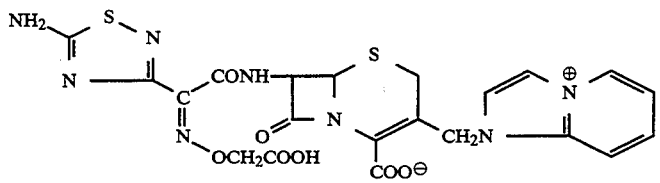

(i) To a solution of 2-(5-tert-butoxycarbonylamino-1,2,4-thiadiazol-3-yl)-2-oxoacetic acid in ethanol (100 ml), prepared from 13 g of 2-(5-amino-1,2,4-thiadiazol-3-yl)acetic acid and 10.7 g of selenium dioxide in a manner as in Reference Example 3, is added, under ice-cooling, 6.2 g of O-tert-butoxycarbonylmethylhydroxylamine(prepared from 14 g of N-tert-butoxycarbonylmethoxyphthalimide and 2.3 g of methylhydrazine) and the mixture is stirred at room temperature for 4 hours. Ethanol is then evaporated off and the residue is shaken with ethyl acetate and water. The organic layer is separated and extracted with an aqueous sodium bicarbonate solution. The aqueous extract is made acid with 1N-HCl and extracted with ethyl acetate. The extract is dried over anhydrous magnesium sulfate. The solvent is then evaporated off and the residue is crystallized from hexane to give, after filtration and drying, 11 g of 2-(5-tert-butoxycarbonylamino-1,2,4-thiadiazol-3-yl)-2(Z)-(tert-butoxycarbonylmethoxyimino)acetic acid.

mp 128° C. (decomposition)

NMR spectrum (CDCl$_3$) δ: 1.43(9H, s), 1.55(9H, s),4.73(2H,s).

(ii) To a solution of 13 g of 2-(tert-butoxycarbonylamino-1,2,4-thiadiazol-3-yl)-2(Z)-(tert-butoxycarbonylmethoxyimino)acetic acid in 100 ml of dichloromethane, 7 g of phosphorus pentachloride is added and the mixture is stirred for 20 minutes under ice-cooling. The reaction mixture is evaporated to dryness and to the residue is added hexane and the solvent is evaporated off again. The residue is dissolved in 5 ml of dichloromethane and the solution is added under ice-cooling to a solution prepared by allowing 10 g of 7β-amino-3-(3-oxobutyryloxymethyl)-3-cephem-4-carboxylic acid and 16 g of N,O-bistrimethylsilylacetamide to react in 200 ml of dichloromethane at room temperature for one hour. The mixture is stirred at the same temperature for one hour and the solvent is then evaporated under reduced pressure. The residue is dissolved in 300 ml of ethyl acetate and the solution is washed with water and then dried over anhydrous magnesium sulfate. Then, the solvent is evaporated off and the residue is triturated with hexane. Insoluble substance is collected by filtration to give 23 g of 7β-[2-(5-tert-butoxycarbonylamino-1,2,4-thiadiazol-3-yl)-2(Z)-(tert-butoxycarbonylmethoxyimino)acetamido]-3-(3-oxobutyryloxymethyl)-3-cephem-4-carboxylic acid.

IR spectrum $\nu_{max}^{KBr}$cm$^{-1}$: 3250, 2960, 1780, 1715, 1540, 1370, 1205, 1150, 1060.

NMR spectrum(d$_6$-DMSO) δ: 1.43(9H, s), 1.50(9H, s), 2.18 (3H, s), 3.41 and 3.65(2H, ABq, J=18 Hz), 3.62(2H, s), 4.66(2H, s), 4.78 and 5.06(2H, ABq, J=12 Hz), 5.15 (1H, d, J=4.8 Hz), 5.86l(1H, d.d, J=4.8 Hz and 8 Hz), 9.56(1H, d, J=8 Hz).

(iii) The whole amount of the compound obtained in (ii) is added to 50 ml of trifluoroacetic acid under ice-cooling. Then, the cooling-bath is removed and the reaction mixture is stirred at room temperature for 1.5 hours. After being diluted with ethyl acetate, the reaction mixture is evaporated off to dryness and the residue is triturated with ethyl acetate. insoluble substance is collected by filtration to give 12 g of 7β-[2-(5-amino-1,2,4-thiadiazol-3-yl)-2(Z)-carboxymethoxyiminoacetamido]-3-(3-oxobutyryloxymethyl)-3-cephem-4-carboxylic acid. From the filtrate, after evaporation to dryness, addition of diethyl ether to the residue and filtration of insoluble material, 5 g of the same objective compound is recovered.

IR spectrum $\nu_{max}^{KBr}$ cm$^{-1}$: 1760, 1720, 1630, 1520, 1400, 1310, 1180, 1145.

NMR spectrum(D$_6$-DMSO) δ: 2.20(3H, s), 3.41 and 3.65(2H, ABq, J=18 Hz), 3.63(2H, s), 4.65(2H, s), 4.78 and 5.07(2H, ABq, J=12 Hz), 5.15L(1H, d, J=4.8 Hz), 5.85(1H, d.d, J=4.8 Hz and 8 Hz), 8.10l(2H, br.), 9.48(1H, d, J=8 Hz).

(iv) One gram of 7β-[2-(5-amino-1,2,4-thiadiazol-3-yl-2(Z)-carboxymethoxyiminoacetamido]-3-(3-oxobutyryloxymethyl)-3-cephem-4-carboxylic acid, 1 g of imidazo[1,2-a]pyridine and 1 g of sodium iodide are added to a mixture of 10 ml of acetonitrile and 10 ml of water and heated in an oil bath kept at 70°–75° C. for 1.5 hours. The reaction mixture is worked up as in Example 1 to give the above-identified compound.

Elemental analysis for $C_{21}H_{17}N_8O_7S_2Na.5H_2O$: Calcd.(%): C, 42.79; H, 3.08; N, 19.01 Found (%): C, 42.88; H, 3.64; N, 1755

IR spectrum $\nu_{max}^{KBr}$ cm$^{-1}$: 1760, 1600, 1520, 1400, 1305, 1050.

NMR spectrum(D$_2$O) δ: 3.16 and 3.53(2H, ABq, J=18 Hz), 5.22(1H, d, J=4.8 Hz), 5.32(2H, br.s), 5.86(1H, d, J=4.8 Hz), 7.40–8.80(6H, m).

EXAMPLE 13

7β-[2-(5-Amino-1,2,4-thiadiazol-3yl)-2(Z)-methoxyiminoacetamido]-3-[(imidazo[1,2-pyridazinium-1-yl)methyl]-3-cephem-4-carboxylate

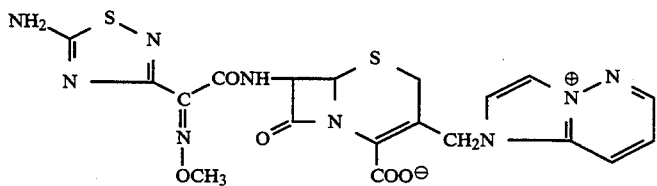

7β-[2-(5-Amino-1,2,4-thiadiazol-3-yl)-2(Z)-methoxyiminoacetamido]-3-(3-oxobutyryloxymethyl)-3-cephem-4-carboxylic acid (1.1 g), imidazo[1,2-b]pyradazine (1.0 g) and potassium iodide (1.1 g) are dissolved in 30 ml of 50% aqueous acetonitrile and the mixture is heated for 2 hours at 60°–70° C. After cooling, the reaction mixture is chromatographed on a column of silica gel with acetone and then with aqueous acetone, successively. Fractions containing the objective compound are combined and concentrated under reduced pressure. The residue is then chromatographed on a column of MCI gel CHP2OP® resin (Mitsubishi Kasei, Japan) with water and then with aqueous alcohol. Fractions containing the object compound are combined and concentrated and the residue is lyophilized to give the title compound.

Elemental analysis for: $C_{19}H_{17}N_9O_5S_2.3 H_2O$ Calcd. (%):C,40.07; H,4.07; N,22.13. Found (%):C,39.75; H,3.51; N,21.89.

IR spectrum $\nu_{max}^{KBr}$ cm$^{-1}$: 1765, 1660, 1610, 1520.

NMR spectrum (d$_6$-DMSO) δ: 3.03 & 3.44(2H, ABq,J=18 Hz), 3.86(3H,s), 4.99(1H,d,J=4.5 Hz), 5.27 & 5.51(2H,ABq,J=14 Hz), 5.63(1H,d.d,J=4.5 Hz & 8 Hz), 7.8–8.32(1H,m), 8.12(2H,br.s), 8.76(2H.s), 9.04 (1H,d,J=4 Hz), 9.31(1H,d,J=9 Hz), 9.44(1H. d,J=8 Hz).

EXAMPLE 14

7β-[2-(5-Amino-1,2,4-thiadiazol-3-yl)-2(Z)-ethoxyiminoacetamido[-3-[(imidazo[1,2-b]pyridazinium-1-yl)methyl]-3-cephem-4-carboxylate

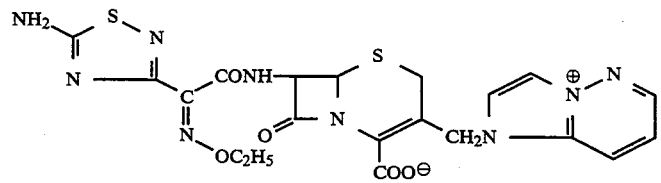

7β-[2-(5-Amino-1,2,4-thiadiazol-3-yl)-2(Z)-ethoxyiminoacetamido]-3-(oxobutyryloxymethyl)-3-cephem-4-carboxylic acid is made to react with imidazo[1,2-b]pyridazine by the procedure of Example 1 to give the title compound.

Elemental analysis for: $C_{20}H_{19}N_9O_5S_2.4H_2O$ Calcd. (%): C,39.93; H,4.52; N,20.95. Found (%): C,40.35; H,4.68; N,20.68.

IR spectrum $\nu_{max}^{KBr}$ cm$^{-1}$: 1770, 1670, 1610, 1520.

NMR spectrum (d$_6$-DMSO) δ: 1.20(3H,t,J=7 Hz), 3.03 & 3.44(2H,ABq,J=18 Hz), 4.13(2H,q,J=7 Hz), 4.99(1H,d,J=4.5 Hz), 5.28 & 5.52(2H,ABq,J=14 Hz), 5.65(1H,d.d,J=4.5 Hz & 8 Hz), 7.8–8.2(1H,m), 8.75(2H,s), 9.05(1H,d,J=4 Hz), 9.28(1H,s), 9.43 (1H,d,J=8 Hz).

EXAMPLE 15

7β-[2-(5-Amino-1,2,4-thiadiazol-3-yl)-2(Z)-methoxyiminoacetamido]-3-[(8-methylimidazo[1,2-b]pyridazinium-1-yl)methyl]-3-cephem-4-carboxylate

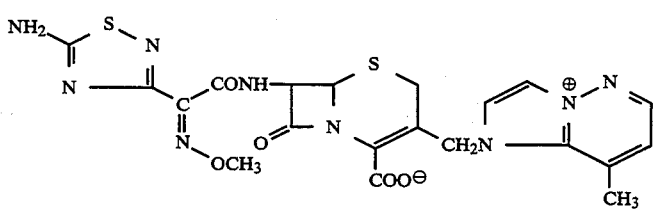

By the procedure of Example 1, 7β-[2-(5-amino-1,2,4-thiadiazol-3-yl)-2(Z)-methoxyiminoacetamido]-3-(3-b]pyridazinium-1-yl)methyl]-3-cephem-4-carboxylate

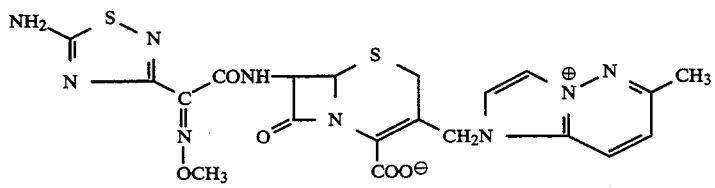

oxobutyryloxymethyl)-3-cephem-4-carboxylic acid is reacted with 8-methylimidazo[1,2-b]pyridazine to give the title compound.

Elemental analysis for: $C_{20}H_{19}N_9O_5S_2.4H_2O$ Calcd. (%): C,39.34; H,4.62; N,20.64. Found (%): C,39.48; H,4.92; N,20.74.

IR spectrum $\nu_{max}^{KBr}$ cm$^{-1}$: 1765, 1670, 1610, 1520.

NMR spectrum (d$_6$-DMSO) δ: 2.17(3H,s), 3.90(3H,s), 3.06 & 3.39(2H,ABq,J=18 Hz), 5.09(1H, d,J=4.5 Hz), 5.50(2H,br.s), 5.70(1H,d.d,J=4.5 Hz & 8 Hz), 7.68(1H,d,J=5 Hz), 7.97(2H,br.s), 8.32–8.52(1H,m), 8.56–8.66(1H,m), 8.84(1H,d,J=5 Hz), 9.47(1H,d,J=8 Hz).

EXAMPLE 16

7β-[2-(5-Amino-1,2,4-thiadiazol-3-yl)-2(Z)-ethoxyiminoacetamido]-3-[(5-methylimidazo[1,5-a]pyridinium-2-yl)methyl]-3-cephem-4-carboxylate

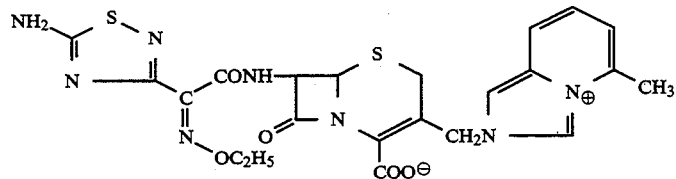

By the procedure of Example 1, 7β-[2-(5-amino-1,2,4-thiadiazol-3-yl)-2(Z)-ethoxyiminoacetamido]-3-(3-oxobutyryloxymethyl)-3-cephem-4-carboxylic acid is reacted with 5-methylimidazo[1,5-a]pyridine to give the title compound.

Elemental analysis for: $C_{22}H_{22}N_8O_5S_2.2H_2O$ Calcd. (%): C,45.67; H,4.53; N,19.37. Found (%): C,45.31; H,5.00; N,19.21.

IR spectrum $\nu_{max}^{KBr}$ cm$^{-}$: 1760, 1660, 1610, 1510, 1390, 1350.

NMR spectrum (d$_6$-DMSO) δ: 1.20(3H,t,J=7 Hz), 2.66(3H,s), 3.17(2H×½,ABq,J=18 Hz), 4.12(2H,q,J=17 Hz), 5.03(1H,d,J=5 Hz), 5.06 & 5.54(2H,ABq,J=14 Hz), 5.67(1H,d.d,J=5 Hz & 8 Hz), 6.9–7.4(2H,m), 7.79(1H,d,J=8 Hz), 8.09(1H,br.s), 8.63(1H,s), 9.39(1H,d,J=8 Hz), 9.93(1H,s).

EXAMPLE 17

7β-[2-(5-Amino-1,2,4-thiadiazol-3-yl)-2(Z)-methoxyiminoacetamido]-3-[(6-methylimidazo[1,2-b]pyridazinium-1-yl)methyl]-3-cephem-4-carboxylate By the procedure of Example 1, 7β-[2-(5-amino-1,2,4-thiadiazol-3-yl)-2(Z)-methoxyiminoacetamido]-3-(3-oxobutyryloxymethyl)-3-cephem-4-carboxylic acid is reacted with 6-methylimidazo[1,2-b]pyridazine to give the title compound.

Elemental analysis for $C_{20}H_{19}N_9O_5S_2.5H_2O$ Calcd. (%): C, 38.77; H, 4.72; N, 20.34 Found (%): C, 38.94; H, 4.69; N, 20.32

IR spectrum $\nu_{max}^{KBr}$ cm$^{-1}$: 1765, 1660, 1605, 1520

NMR spectrum (d$_6$-DMSO) δ: 2.99 & 3.43(2H,ABq,J=18 Hz), 2.67(3H,s), 3.86(3H,s), 4.97(1H,d,J=4.5 Hz), 5.24 & 5.40 (2H,ABq,J=14 Hz), 5.61(1H,d.d,J=4.5 Hz & 8 Hz), 7.86(1H,d, J=9 Hz), 8.10(2H,br.s), 8.58–8.76(2H,m), 9.20(1H,d,J=9 Hz), 9.43(1H,d,J=8 Hz).

By the procedure of Example 1, compounds of the following Examples 18–24 can be prepared by reacting 7β-[2-(5-amino-1,2,4-thiadiazol-3-yl)-2(Z)-methoxyiminoacetamino]-3-(3-oxobutyryloxymethyl)-3-cephem-4-carboxylic acid with various imidazo[1,2-b]pyridazines.

EXAMPLE 18

7β-[2-(5-Amino-1,2,4-thiadiazol-3-yl)-2(Z)-methoxyiminoacetamido]-3-[(6-ethoxyimidazo[1,2-b]pyridazinium-1-yl)methyl]-3-cephem-4-carboxylate

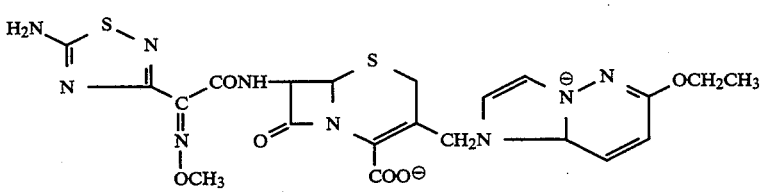

Elemental analysis for $C_{21}H_{21}N_9O_6S_2.3H_2O$ Calcd. (%): C, 41.11; H, 4.43; N, 20.54 Found (%): C, 40.95; H, 4.56; N, 20.32.

IR spectrum $\nu_{max}^{KBr}$ cm$^{-1}$: 1770, 1670, 1600, 1500.

NMR spectrum (d$_6$-DMSO) δ: 1.44 (3H, t, J=7 Hz), 2.98 & 3.42 (2H, ABq, J=18 Hz), 3.87 (3H, s), 4.46 (2H, q, J=7 Hz), 4.98 (1H, d, J=4.5 Hz), 5.20 & 5.50 (2H, ABq, J=14 Hz), 5.60 (1H, d.d, J=4.5 Hz & 8 Hz), 7.57 (2H, d, J=14 Hz), 8.04 (2H, br. s), 8.46 (1H, d, J=2 Hz), 8.64 (1H, d, J=2 Hz), 9.24 (1H, d, J=10 Hz), 9.40 (1H, d, J=8 Hz).

EXAMPLE 19

7β-[2-(5-Amino-1,2,4-thiadiazol-3-yl)2(Z)-methoxyiminoacetamido]-3-[(6-methylthioimidazo[1,2-b]pyridazinium-1-yl)methyl]-3-cephem-4-carboxylate

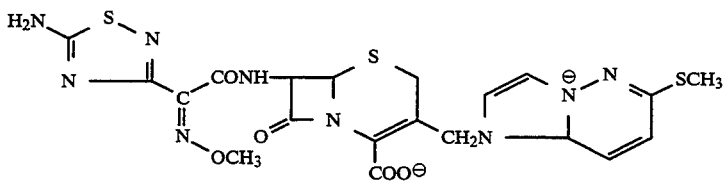

Elemental analysis for $C_{20}H_{19}N_9O_5S_3.7/2\ H_2O$: Calcd. (%): C, 38.45; H, 4.20; N, 20.18. Found (%): C, 38.40; H, 4.25; N, 20.11.

IR spectrum $\nu_{max}^{KBr}$ cm$^{-1}$: 1770, 1670, 1600, 1520.
NMR spectrum (d$_6$-DMSO) δ: 2.66 (3H, s), 3.01 (2H×½, ABq×½, J=18 Hz), 3.86 (3H, s), 4.98 (1H, d, J=4.5 Hz), 5.22 & 5.50 (2H, d, J=14 Hz), 5.63 (1H, d.d, J=4.5 Hz & 8 Hz), 7.91 (1H, d, J=10 Hz), 8.10 (2H, br. s), 8.54–8.74 (2H, m), 9.22 (1H, d, J=10 Hz), 9.44 (1H, d, J=8 Hz).

EXAMPLE 20

7β-[2-(5-Amino-1,2,4-thiadiazol-3-yl)-2(Z)-methoxyiminoacetamido]-3-[(6-chlorimidazo[1,2-b]pyridazinium-1-yl)methyl]-3-cephem-4-carboxylate

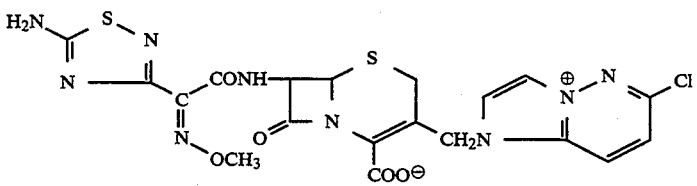

Elemental analysis for $C_{19}H_{16}ClN_9O_5S_2.4H_2O$: Calcd. (%): C, 36.69; H, 3.89; N, 20.27. Found (%): C, 36.80; H, 3.12; N, 20.09.

IR spectrum $\nu_{max}^{KBr}$ cm$^{-1}$: 1775, 1670, 1610, 1520.
NMR spectrum (d$_6$-DMSO) δ: 2.98 & 3.42 (2H, ABq, J=18 Hz), 3.86 (3H, s), 4.98 (1H, d, J=4.5 Hz), 5.24 & 5.55 (2H, ABq, J=14 Hz), 5.59 (1H, d.d, J=4.5 Hz & 8 Hz), 8.09 (2H, br. s), 8.17 (1H, d, J=9 Hz), 8.73–8.90 (2H, m), 9.42 (1H, d, J=8 Hz), 9.48 (1H, d, J=9 Hz).

EXAMPLE 21

7β-[2-(5-Amino-1,2,4-thiadiazol-3-yl)-2(Z)-methoxyiminoacetamido]-3-[(6-methoxyimidazo[1,2-b]pyridazinium-1-yl]-3-cephem-4-carboxylate

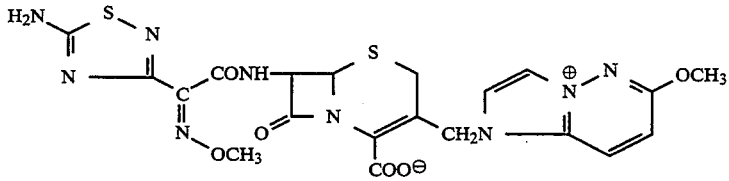

Elemental analysis for $C_{20}H_{19}N_9O_6S_2.9/2\ H_2O$: Calcd. (%): C, 38.34; H, 4.50; N, 20.12. Found (%): C, 38.39; H, 4.54; N, 20.02.

IR spectrum $\nu_{max}^{KBr}$ cm$^{-1}$: 1770, 1670, 1610, 1510.
NMR spectrum (d$_6$-DMSO) δ: 2.98 & 3.43 (2H, ABq, J=18 Hz), 3.86 (3H, s), 4.06 (3H, s), 4.97 (1H, d, J=4.5 Hz), 5.20 & 5.50 (2H, ABq, J=14 Hz), 5.62 (1H, d.d, J=4.5 Hz & 8 Hz), 7.62 (1H, d, J=9 Hz), 8.04 (2H, br. s), 8.38–8.68 (2H, m), 9.22 (1H, d, J=9 Hz), 9.42 (1H, d, J=8 Hz).

EXAMPLE 22

7β-2(5-Amino-1,2,4-thiadiazol-3-yl)-2(Z)-methoxyiminoacetamido]-3-[(6-methylimidazo[1,2-b]pyridazinium-1-yl)methyl]-3-cephem-4-carboxylate

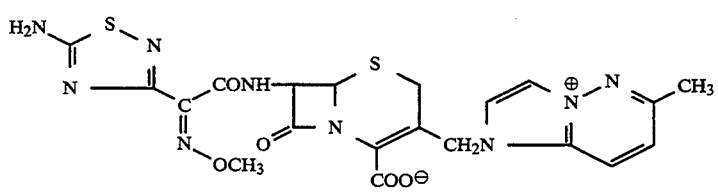

Elemental analysis for $C_{20}H_{19}N_9O_5S_2.5H_2O$: Calcd. (%): C, 38.77; H, 4.72; N, 20.34. Found (%): C, 38.94; H, 4.69; N, 20.32.

IR spectrum $\nu_{max}^{KBr}$ cm$^{-1}$: 1765, 1660, 1605, 1520.
NMR spectrum (d$_6$-DMSO) δ: 2.99 & 3.43 (2H, ABq, J=18 Hz), 2.67 (3H, s), 3.86 (3H, s), 4.97 (1H, d, J=4.5 Hz), 5.24 & 5.40 (2H, ABq, J=14 Hz), 5.61 (1H, d.d, J=4.5 Hz & 8 Hz), 7.86 (1H, d, J=9 Hz), 8.10 (2H, br.

s), 8.58–8.76 (2H, m), 9.20 (1H, d, J=9 Hz), 9.43 (1H, d, J=8 Hz).

EXAMPLE 23

7β-[2-(5-Amino-1,2,4-thiadiazol-3-yl)-2(Z)-methoxyiminoacetamido]-3-[(6-dimethylaminoimidazo[1,2-b]pyridazinium-1-yl)methyl]-3-cephem-4-carboxylate

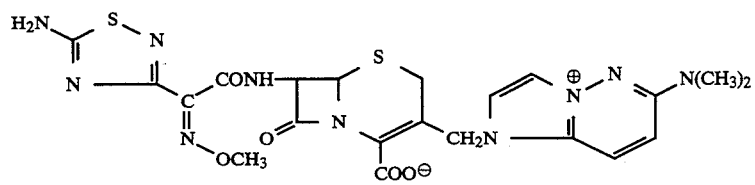

Elemental analysis for $C_{21}H_{22}N_{10}O_5S_2 \cdot 4H_2O$: Calcd. (%): C, 39.99; H, 4.79; N, 22.21. Found (%): C, 40.26; H, 3.90; N, 22.07.

IR spectrum (KBr) $cm^{-1}$: 1775, 1670, 1610, 1590, 1510.

NMR spectrum ($d_6$-DMSO) δ: 3.04 (2H, br. s), 3.14 (6H, s), 3.86 (3H, s), 4.96 (1H, d, J=4.5 Hz), 5.15 & 5.43 (2H, ABq, J=14 Hz), 5.57 (1H, d.d, J=4.5 Hz & 8 Hz), 7.68 (1H, d, J=10 Hz), 8.07 (2H, br. s), 8.24 (1H, br. s), 8.39 (1H, br. s), 8.96 (1H, d, J=10 Hz), 9.40 (1H, d, J=9 Hz).

EXAMPLE 24

7β-2-(5-Amino-1,2,4-thiadiazol-3-yl)-2(Z)-methoxyiminoacetamido]-3-[(6-fluoroimidazo[1,2-b]pyridazinium-1-yl)methyl]-3-cephem-4-carboxylate

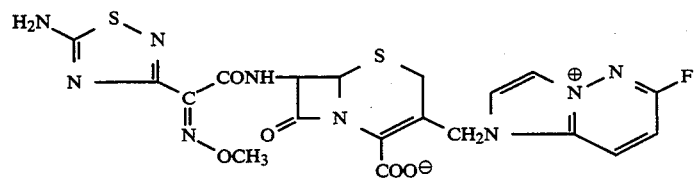

Elemental analysis for $C_{19}H_{16}N_9O_5S_2F \cdot 4H_2O$: Calcd. (%): C, 37.69; H, 3.99; N, 20.82. Found (%): C, 38.03; H, 3.89; N, 20.55.

IR spectrum $\nu_{max}^{KBr}$ $cm^{-1}$: 1770, 1670, 1610, 1520.
NMR spectrum ($d_6$-DMSO) δ: 3.00 (2H×½, Abq×½, J=18 Hz), 3.86 (3H, s), 4.98 (1H, d, J=4.5 Hz), 5.26 & 5.59 (2H, Abq, J=14 Hz), 5.62 (1H, d.d, J=4.5 Hz & 8 Hz), 7.9–8.24 (3H, m), 8.62–8.86 (2H, m), 9.41 (1H, d, J=8 Hz), 9.48–9.74 (1H, m).

EXAMPLE 25

7β-[2-(5-Amino-1,2,4-thiadiazol-3-yl-2(Z)-carboxymethoxyiminoacetamido]-3-[(imidazo[1,2-b]pyridazinium-1-yl)methyl]-3-cephem-4-carboxylate.monosodium salt

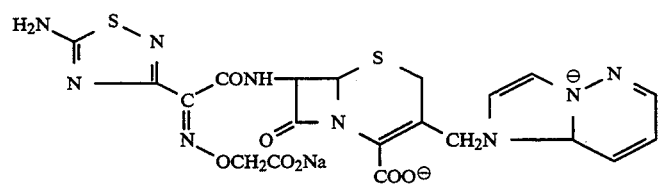

By the procedure of Example 1, 7β-[2-(5-amino-1,2,4-thiadiazol-3-yl)-2(Z)-carboxymethoxyiminoacetamido]-3-(3-oxobutyryloxymethyl)-3-cephem-4-carboxylic acid is made to react with imidazo[1,2-b]pyridazine to give the title compound.

Elemental analysis for $C_{20}H_{16}N_9O_7S_2N_9 \cdot 3/2H_3O$: Calcd. (%): C, 34.38; H, 4.18; N, 18.04. Found (%): C, 34.48; H, 3.64; N, 17.54.

IR spectrum $\nu_{max}^{KBr}$ $cm^{-1}$: 1770, 1600, 1520.

NMR spectrum ($d_6$-DMSO-$D_2O$) δ: 3.52 & 3.72 (1H, ABq, J=18 Hz), 4.34 (2H, s), 4.98 (1H, d, J=4.5 Hz), 5.34 & 5.50 (2H, ABq, J=14 Hz), 5.68 (1H, d, J=4.5 Hz), 7.90 (1H, d.d, J=5 Hz & 10 Hz), 8.17 (1H, d, J=10 Hz).

EXAMPLE 26

7β-[2-(5-Amino-1,2,4-thiadiazol-3-yl)-2(Z)-methoxyiminoacetamido]-3-[[6-(2-dimethylaminoethylthio)imidazo-[1,2-b]pyridazinium-1-yl]methyl]-3-cephem-4-carboxylate.dihydrochloride

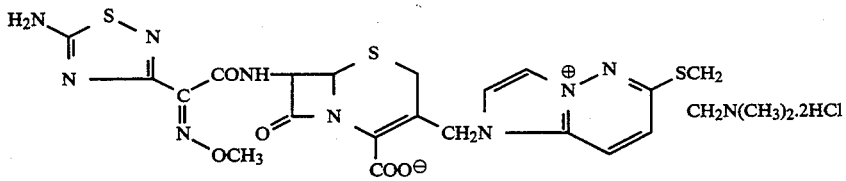

7β-[2-(5-amino-1,2,4-thiadiazol-3-yl)-2(Z)-methoxyiminoacetamido]-3-(3-oxobutyryloxymethyl)-3-cephem-4-carboxylic acid (1.5 g), 6-(2-dimethylaminoethylthio)imidazo[1,2-b]pyridazine (1.5 g) and potassium iodide (1.5 g) are dissolved in a mixture of 5 ml of 1N hydrochloric acid, 5 ml of water and 10 ml of acetonitrile and the solution is heated for 2 hours at 60°–70° C. with stirring. The acetonitrile is evaporated under reduced pressure and the residue is chromatographed on a column of high porous polymer MCI gel CHP20P ® (Mitsubishi Kasei, Japan) with 0.01N hydrochloric acid. Fractions containing the object compound are combined and concentrated under reduced pressure and the residue is lyophilized to give 0.13 g of the title compound.

Elemental analysis for $C_{23}H_{24}N_{10}O_5S_3 \cdot 2H_2O \cdot 1 1/2 H_2O$: Calcd. (%): C, 35.03; H, 4.73; N, 17.76. Found (%): C, 35.13, H, 4.46; N, 17.66.

IR spectrum $\nu_{max}^{KBr}$ cm$^{-1}$: 1770, 1675, 1625, 1510.

NMR spectrum (d$_6$-DMSO-D$_2$O) δ: 2.90 (6H, s), 3.3–3.85 (6H, m), 4.08 (3H, s), 5.18 (1H, d, J=4.5 Hz), 5.46 (2H, br. s), 5.82 (1H, d, J=4.5 Hz), 7.97 (1H, d, J=10 Hz), 8.27 (1H, br. s), 8.73 (1H, d, J=10 Hz), 8.79 (1H, br. s).

EXAMPLE 27

7β-[2-(5-Amino-1,2,4-thiadiazol-3-yl)-2(Z)-methoxyiminoacetamido]-3-[(7-methylimidazo[1,2-b]pyridazinium-1-yl)methyl]-3-cephem-4-carboxylate

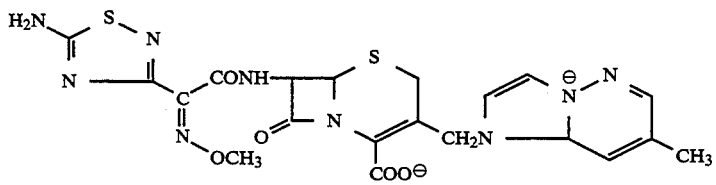

By the procedure of Example 1, 7β-2-(5-amino-1,2,4-thiadiazol-3-yl)-2(Z)-methoxyiminoacetamido]-3-(3-oxobutyryloxymethyl)-3-cephem-4-carboxylic acid is made to react with 7-methylimidazo[1,2-b]pyridazine to give the title compound.

Elemental analysis for $C_{20}H_{19}N_9O_5S_2 \cdot 5H_2O$: Calcd. (%): C, 38.77; H, 4.72; N, 20.34. Found (%): C, 38.82; H, 4.75; N, 20.32.

IR spectrum $\nu_{max}^{KBr}$ cm$^{-1}$: 1760, 1665, 1610, 1520.

NMR spectrum (d$_6$-DMSO) δ: 2.56 (3H, s), 3.00 (2H×½, ABq×½, J=18 Hz), 3.86 (3H, s), 4.99 (1H, d, J=4.5 Hz), 5.20 & 5.43 (2H, ABq, J=14 Hz), 5.62 (1H, d.d, J=4.5 Hz & 8 Hz), 8.09 (2H, br. s), 8.58–8.75 (2H, m), 8.97 (1H, br. s), 9.08 (1H, br. s), 9.42 (1H, d, J=8 Hz).

EXAMPLE 28

7β-[2-(5-Amino-1,2,4-thiadiazol-3-yl)-2(Z)-methoxyiminoacetamido]-3-[(imidazo[1,2-b]pyridazinium-1-yl)methyl]-3-cephem-4-carboxylate (1) 7β-tert-Butoxycarbonylamino-3-(3-oxobutyryloxymethyl)-3-cephem-4-carboxylic acid (4.14 g), imidazo[1,2-b]pyridazine (4.14 g) and sodium iodide (8.28 g) are added to a mixture of 20 ml of water and 20 ml of acetonitrile and the mixture is heated for 2 hours at 70° C. with stirring. After being allowed to cool to room temperature, the reaction mixture is subjected to silica gel (100 g) column chromatography. The column is washed with acetone and 95% acetone-water. Fractions containing the object compound are combined and concentrated and the residue is lyophilized to give 1.14 g of 7β-tert-butoxycarbonylamino-3-[(imidazo[1,2-b]pyridazinium-1-yl)methyl]-3-cephem-4-carboxylate as a powder.

IR spectrum $\nu_{max}^{KBr}$ cm$^{-1}$: 1760, 1710, 1610, 1520, 1385, 1370.

NMR spectrum (d$_6$-DMSO) δ: 1.39 (9H, s), 3.08 & 3.48 (2H, ABq, J=18 Hz), 4.91 (1H, d, J=6 Hz), 5.1–5.6 (3H, m), 7.6–8.2 (2H, m), 8.78 (2H, br. s), 9.07 (1H, d, J=4 Hz), 9.31 (1H,d, J=10 Hz).

TLC (Merck, Art 5715; solvent:acetonitrile:water=4:1), Rf=0.4.

(2) 7β-(tert-Butoxycarbonylamino)-3-[(imidazo[1,2-b]pyridazinium-1-yl)methyl]-3-cephem-4-carboxylate (1.45 g) is dissolved in 20 ml of trifluoroacetic acid and the solution is stirred at room temperature for 30 minutes. The reaction mixture is concentrated under reduced pressure and the residue is treated with 100 ml of ether with stirring. Precipitate separated is collected by filtration and washed with ether to give 1.42 g of 7β-amino-3-[(imidazo[1,2-b]pyridazinium-1-yl)methyl-3-cephem-4-carboxylate trifluoroacetate The yield: 95%.

IR spectrum $\nu_{max}^{KBr}$ cm$^{-1}$: 1780, 1680, 1525, 1410, 1380.

NMR spectrum (CF$_3$COOD) δ: 3.50 & 3.80 (2H, ABq, J=18 Hz), 5.51 (2H, br. s), 5.58 & 6.09 (2H, ABq, J=14 Hz), 7.96 (1H, d.d, J=5 Hz & 10 Hz), 8.26 (1H, d, J=2 Hz), 8.40 (1H, d, J=2 Hz), 8.71 (1H, d, J=10 Hz), 9.00 (1H, d, J=5 Hz).

TLC (Merck, Art 5715; solvent:acetonitrile:formic acid:water=3:1:1), Rf=0.5.

(3) To 20 ml of dichloromethane, are added 2-(5-amino-1,2,4-thiadiazol-3-yl)-2(Z)-2-methoxyiminoacetic acid (202 mg), N-hydroxybenztriazole (153 mg) and dicyclohexylcarbodiimide (206 mg) and the suspension obtained is stirred for 60 minutes at room temperature. Insoluble material is filtered off and the filtrate is added to a solution of 445 mg of 7β-amino-3-[(imidazo[1,2-b]pyridazinium-1-yl)methyl]-3-cephem-4-carboxylate trifluoroacetate in 8 ml of dimethylacetamide and the mixture is stirred for 16 hours at room temperature. To the reaction mixture is added 30 ml of ether. After the ether layer is removed by decantation, the residue is dissolved in water and subjected to chromatography on a column of XAD-2 ®. The column is developed with ether and then with 20% ethanol-water. The eluate containing the object compound is concentrated and the residue is lyophilized to give 0.2 g of the title compound.

I.R. spectrum of the compound is the same as that in Example 13.

EXAMPLE 29

7β-[2-(5-Amino-1,2,4-thiadiazol-3-yl)-2(Z)methoxyiminoacetamido]-3-[(imidazo[1,2-b]pyridazinium-1-yl)methyl]-3-cephem-4-carboxylate.

(1) To a solution of 218 mg of phosphorus pentachloride in 3 ml of methylene chloride, 202 mg of 2-(5- amino-1,2,4-thiadiazol-3-yl)-2(Z)-methoxyiminoacetic acid is added under cooling at −20° C. with stirring and the mixture is stirred for half an hour at −20° C. and for two hours at −5° C. The reaction mixture in concentrated under reduced pressure and the residue is triturated with 10 ml of hexane. The precipitate is collected by filtration to give 2-(5-amino-1,2,4-thiadiazol-3-yl)-2(Z)-methoxyiminoacetyl chloride hydrochloride.

(2) 7β-Amino-3-[(imidazo[1,2-b]pyridazinoum-1-yl)methyl-3-cephem-4-carboxylate hydrochloride (354 mg) is dissolved in a mixture of 10 ml each of acetone and water under ice-cooling. After addition of 504 mg of sodium bicarbonate and one minute's stirring, the whole amount of 2-(5-amino-1,2,4-thiadiazol-3-yl)-2(Z)-methoxyiminoacetyl chloride hydrochloride obtained above is added and the mixture is stirred energetically for 20 minutes under ice-cooling.

To the reaction mixture is added 20 ml of ethyl acetate and the upper layer is removed and the lower layer is washed twice with each 20 ml of ethyl acetate. The aqueous layer is separated and acidified with concentrated hydrochloric acid to pH 1 and washed with a mixture of 20 ml of methyl ethyl ketone and 10 ml of ethyl acetate and then with a mixture of each 10 ml of methyl ethyl ketone and ethyl acetate. Then, the aqueous layer is adjusted to pH 3 and chromatographed on a column of MCI gel, CHP 20P ® (Mitsubishi Kasei, Japan), first, with water and then with aqueous acetonitrile. Fractions containing the object compound are combined and concentrated and the residue is lyophilized to give the little compound.

TLC (Silica gel, Merck, Art 5715; Solvent: acetonitrile:water=4:1): Rf=0.26

IR spectrum $v_{max}^{KBr}$ cm$^{-1}$: 1765, 1660, 1610, 1520

EXAMPLE 30

7β-[2-(5-Amino-1,2,4-thiadiazol-3-yl)-2(Z)-methoxyiminoacetamido]-3-[(imidazo[1,2-b]pyridazinium-1-yl(methyl]-3-cephem-4-carboxylate.

(30-1) By the procedure of Example 29 but using 606 mg of triethylamine instead of the 504 mg of sodium bicarbonate, the title compound is obtained and identified as such by comparing its IR-, NMR-spectra, Rf-value in TLC and retention time in HPLC with those of the product obtained in Example 29.

(30-2) By the procedure of Example 29 but using tetrahydrofuran instead of the acetone, the title compound is obtained.

(30-3) By the procedure of Example 29 but using acetonitrile instead of the acetone, the title compound is obtained.

EXAMPLE 31

7β-[2-(5-Amino-1,2,4-thiadiazol-3-yl)-2(Z)-methoxyiminoacetamido]-3-[(imidazo[1,2-b]pyridazinium-1-yl)methyl]-3-cephem-4-carboxylate 7β-Amino-3-[(imidazo[1,2-b]pyridazinium-1-yl)methyl]-3-cephem-4-carboxylate hydrochloride (354 mg) is dissolved in a mixture of 4 ml of dimethylformamide and 1.11 g of tributylamine and the solution is cooled to −20° C. To this, 2-(5-amino-1,2,4-thiadiazol-3-yl)-2(Z)-methoxyiminoacetyl chloride hydrochloride (the whole amount of it prepared as in Example 29 using the same amounts of the starting material and reagents) is added and the mixture is stirred for ten minutes at −20° to −10° C. and then for another ten minutes at −10° to −0° C. The reaction mixture is diluted with 60 ml of ethyl acetate and then treated with 2 ml of 4N solution of hydrogen chloride in ether. The precipitate separated is collected by filtration, washed with 10 ml of ethyl acetate and 20 ml of methylene chloride and then suspended in 5 ml of water. The mixture is adjusted to pH 3 and chromatographed on a column of MCI gel, CHP-20P ®(Mitsubishi-Kasei, Japan). The column is developed first with water and then with aqueous acetonitrile and fractions containing the object compound are combined and concentrated and the residue is lyophilized to give the title compound.

The product obtained showed identical IR-, NMR-spectar, RF-value in TLC and retention time in HPLC with those of the product obtained in Example 29.

EXAMPLE 32

7β-[2-(5-Amino-1,2,4-thiadiazol-3-yl)-2(Z)-methoxyiminoacetamido]-3-[(imidazo[1,2-b]pyridazinium-1-yl)methyl]-3-cephem-4-carboxylate.

(32-1) By the procedure of Example 31 but using dimethylacetamide instead of the dimethylformamide, the title compound is obtained and identified with it by means of physico-chemical measurements.

(32-2) By the procedure of Example 31 but using triethylamine instead of the tributylamine, the title compound is obtained.

What is claimed is:

1. A pharmaceutically acceptable salt of 7β-[2-(5-amino-1,2,4-thiadiazol-3-yl)-2(Z)-methoxyiminoacetamido]-3-[(imidazo[1,2-b]pyridazinium-1yl)-methyl-3-cephem-4-carboxylate.

2. Thy hydrochloride salt of 7β-[2-(5-amino-1,2,4-thiadiazol-3-yl)-2(Z)-methoxyiminoacetamido]-3-[(imidazo[1,2-b]pyridazinium-1yl)methyl-3-cephem-4-carboxylate and a pharmaeutically acceptable carrier.

3. A pharmaceutical composition comprising a pharmacologically effective amount of the compount according to claim 1.

4. A pharmaceutical composition comprising a pharmacologically effective amount of the compound according to claim 2 and a pharmaeutically acceptable carrier.

* * * * *

UNITED STATES PATENT AND TRADEMARK OFFICE
CERTIFICATE OF CORRECTION

PATENT NO. : 5,409,919
DATED : April 25, 1995
INVENTOR(S) : Akio MIYAKE et al.

It is certified that error appears in the above-indentified patent and that said Letters Patent is hereby corrected as shown below:

In Column 70, lines 46-47, Claim 1, contains a typographical error wherein "-1yl)-methyl-3-" should read ---1-yl)-methyl]-3---.

Column 70, line 50, claim 2, "-1yl)methyl-3-" should read --1-yl)-methyl]-3---.

Column 70, line 51, claim 2, delete "and a pharmaceutically acceptable carrier".

Column 70, line 54, claim 3, after "claim 1" insert --and a pharmaceutically acceptable carrier--.

Signed and Sealed this

Twelfth Day of December, 1995

Attest:

BRUCE LEHMAN

*Attesting Officer*  *Commissioner of Patents and Trademarks*